US 8,180,650 B2

(12) United States Patent
Graves et al.

(10) Patent No.: US 8,180,650 B2
(45) Date of Patent: May 15, 2012

(54) USE OF LOCATION AWARENESS TO REQUEST ASSISTANCE FOR A MEDICAL EVENT OCCURRING IN A HEALTHCARE ENVIRONMENT

(75) Inventors: Alan F. Graves, Ottawa (CA); Jeff Fitchett, Ottawa (CA)

(73) Assignee: Avaya Inc., Basking Ridge, NJ (US)

( * ) Notice: Subject to any disclaimer, the term of this patent is extended or adjusted under 35 U.S.C. 154(b) by 1381 days.

(21) Appl. No.: 11/065,420

(22) Filed: Feb. 25, 2005

(65) Prior Publication Data

US 2006/0181424 A1 Aug. 17, 2006

Related U.S. Application Data

(60) Provisional application No. 60/651,623, filed on Feb. 11, 2005.

(51) Int. Cl.
G06Q 50/00 (2006.01)
(52) U.S. Cl. .................................. 705/2; 705/3
(58) Field of Classification Search ............... 705/2–3; 600/300
See application file for complete search history.

(56) References Cited

U.S. PATENT DOCUMENTS

| 4,601,064 | A |   | 7/1986  | Shipley |
|-----------|---|---|---------|---------|
| 5,291,399 | A |   | 3/1994  | Chaco |
| 5,434,775 | A |   | 7/1995  | Sims et al. |
| 5,465,082 | A |   | 11/1995 | Chaco |
| 5,534,851 | A | * | 7/1996  | Russek .............. 340/573.4 |
| 5,544,661 | A |   | 8/1996  | Davis et al. |
| 5,594,786 | A |   | 1/1997  | Chaco et al. |
| 5,610,596 | A |   | 3/1997  | Petitclerc |
| 5,689,229 | A |   | 11/1997 | Chaco et al. |
| 5,822,544 | A |   | 10/1998 | Chaco et al. |
| 5,877,675 | A |   | 3/1999  | Rebstock et al. |
| 5,901,172 | A |   | 5/1999  | Fontana et al. |
| 5,910,776 | A |   | 6/1999  | Black |
| 5,911,687 | A |   | 6/1999  | Sato et al. |

(Continued)

FOREIGN PATENT DOCUMENTS

CA 2263428 2/1998

(Continued)

OTHER PUBLICATIONS

Chronaki et al, "WebOnCOLL: Medical Collaboration in Regional Healthcare Netwoks", IEEE Transactions on Information Technology in Biomedicine, vol. 1, No. 4, Dec 1997, pp. 257-269.

(Continued)

Primary Examiner — Gerald J. O'Connor
Assistant Examiner — Rajiv Raj

(57) ABSTRACT

A method of requesting assistance for a medical event occurring in a hospital. The method comprises receiving data regarding a location of the medical event; receiving data regarding a type of the medical event; receiving data regarding at least one wirelessly detectable tag, each one of the at least one wirelessly detectable tag being associated with a respective one of at least one clinician; determining a location of each clinician within the hospital based at least in part on the data regarding the at least one wirelessly detectable tag; identifying at least one particular clinician as being eligible to provide assistance, based at least in part on the location of the medical event, the type of the medical event, and the respective location of each clinician; and performing an action to cause requesting of assistance for the medical event from each particular clinician.

24 Claims, 29 Drawing Sheets

U.S. PATENT DOCUMENTS

| | | |
|---|---|---|
| 5,942,986 A | 8/1999 | Shabot et al. |
| 5,952,641 A | 9/1999 | Korshun |
| 6,009,333 A | 12/1999 | Chaco |
| 6,026,125 A | 2/2000 | Larrick, Jr. et al. |
| 6,054,950 A | 4/2000 | Fontana |
| 6,211,790 B1 | 4/2001 | Radomsky et al. |
| 6,236,333 B1 | 5/2001 | King |
| 6,239,741 B1 | 5/2001 | Fontana et al. |
| 6,259,355 B1 | 7/2001 | Chaco et al. |
| 6,262,662 B1 | 7/2001 | Back et al. |
| 6,302,844 B1 | 10/2001 | Walker et al. |
| RE37,531 E | 1/2002 | Chaco et al. |
| 6,344,794 B1 | 2/2002 | Ulrich et al. |
| 6,462,656 B2 | 10/2002 | Ulrich et al. |
| 6,539,393 B1 | 3/2003 | Kabala |
| 6,577,238 B1 | 6/2003 | Whitesmith et al. |
| 6,662,068 B1 | 12/2003 | Ghaffari |
| 6,690,741 B1 | 2/2004 | Larrick, Jr. et al. |
| 6,753,671 B1 | 6/2004 | Harvey |
| 6,773,396 B2 | 8/2004 | Flach et al. |
| 6,812,884 B2 | 11/2004 | Richley et al. |
| 6,823,199 B2 | 11/2004 | Gough |
| 6,825,763 B2 | 11/2004 | Ulrich et al. |
| 6,870,916 B2 | 3/2005 | Henrikson et al. |
| 6,876,303 B2 | 4/2005 | Reeder et al. |
| 6,958,677 B1 | 10/2005 | Carter |
| 6,958,706 B2 | 10/2005 | Chaco et al. |
| 6,972,683 B2 | 12/2005 | Lestienne et al. |
| 7,042,337 B2 | 5/2006 | Borders et al. |
| 7,080,061 B2 | 7/2006 | Kabala |
| 7,154,397 B2 | 12/2006 | Zerhusen et al. |
| 7,242,306 B2 | 7/2007 | Wildman et al. |
| 7,283,037 B2 | 10/2007 | Diorio et al. |
| 7,289,227 B2 | 10/2007 | Smetak et al. |
| 7,336,171 B2 | 2/2008 | Kishimoto et al. |
| 2001/0044731 A1 | 11/2001 | Coffman et al. |
| 2002/0044043 A1 | 4/2002 | Chaco et al. |
| 2002/0044059 A1 | 4/2002 | Reeder et al. |
| 2002/0069030 A1 | 6/2002 | Xydis |
| 2002/0147912 A1 | 10/2002 | Shmueli et al. |
| 2002/0165731 A1 | 11/2002 | Dempsey |
| 2002/0183078 A1 | 12/2002 | Hase |
| 2002/0183979 A1 | 12/2002 | Wildman |
| 2003/0055899 A1 | 3/2003 | Burger et al. |
| 2003/0078810 A1 | 4/2003 | Cole et al. |
| 2003/0078811 A1 | 4/2003 | Cole et al. |
| 2003/0132845 A1 | 7/2003 | McDaniel, III |
| 2004/0001446 A1 | 1/2004 | Bhatia et al. |
| 2004/0004460 A1 | 1/2004 | Fitch et al. |
| 2004/0008114 A1 | 1/2004 | Sawyer |
| 2004/0034284 A1 | 2/2004 | Aversano et al. |
| 2004/0078151 A1 | 4/2004 | Aljadeff et al. |
| 2004/0078219 A1 | 4/2004 | Kaylor et al. |
| 2004/0100376 A1 | 5/2004 | Lye et al. |
| 2004/0100377 A1* | 5/2004 | Brackett et al. .......... 340/539.13 |
| 2004/0108954 A1 | 6/2004 | Richley et al. |
| 2004/0125938 A1 | 7/2004 | Turcan et al. |
| 2004/0125940 A1 | 7/2004 | Turcan et al. |
| 2004/0145477 A1 | 7/2004 | Easter et al. |
| 2004/0153344 A1 | 8/2004 | Bui et al. |
| 2004/0178947 A1 | 9/2004 | Richley et al. |
| 2004/0186357 A1 | 9/2004 | Soderberg et al. |
| 2004/0193449 A1 | 9/2004 | Wildman et al. |
| 2004/0203930 A1 | 10/2004 | Farchmin et al. |
| 2004/0252015 A1 | 12/2004 | Galperin et al. |
| 2004/0257224 A1 | 12/2004 | Sajkowsky |
| 2005/0017864 A1 | 1/2005 | Tsoukalis |
| 2005/0027465 A1 | 2/2005 | Pozsgay et al. |
| 2005/0035862 A1 | 2/2005 | Wildman et al. |
| 2005/0105734 A1 | 5/2005 | Buer et al. |
| 2005/0128083 A1 | 6/2005 | Puzio et al. |
| 2005/0148831 A1 | 7/2005 | Shibata et al. |
| 2005/0151641 A1 | 7/2005 | Ulrich et al. |
| 2005/0153681 A1 | 7/2005 | Hanson |
| 2005/0168341 A1 | 8/2005 | Reeder et al. |
| 2005/0188095 A1 | 8/2005 | Gardiner et al. |
| 2005/0201345 A1 | 9/2005 | Williamson |
| 2005/0283382 A1 | 12/2005 | Donoghue et al. |
| 2006/0006999 A1 | 1/2006 | Walczyk et al. |
| 2006/0067250 A1 | 3/2006 | Boyer et al. |
| 2006/0143043 A1 | 6/2006 | McCallie, Jr. et al. |
| 2006/0158329 A1* | 7/2006 | Burkley et al. .......... 340/539.13 |
| 2006/0282459 A1 | 12/2006 | Kabala |

FOREIGN PATENT DOCUMENTS

| | | | |
|---|---|---|---|
| CA | 2362635 | A1 | 8/2000 |
| CA | 2373241 | A1 | 11/2000 |
| CA | 2434714 | A1 | 8/2002 |
| EP | 0 369 662 | A2 | 5/1990 |
| EP | 1 101 437 | A1 | 5/2001 |
| EP | 1 156 336 | A1 | 11/2001 |
| EP | 0 973 316 | A3 | 6/2002 |
| EP | 1 536 306 | A1 | 6/2005 |
| GB | 2 320 397 | A | 6/1998 |
| GB | 2 355 889 | A | 5/2001 |
| GB | 0602885.6 | | 6/2006 |
| GB | 0602887.2 | | 6/2006 |
| GB | 0602901.1 | | 6/2006 |
| GB | 0602903 | | 6/2006 |
| GB | 0602904.5 | | 6/2006 |
| GB | 0602906.0 | | 6/2006 |
| GB | 0602907.8 | | 6/2006 |
| JP | 2002157040 | A | 5/2002 |
| JP | 2003189359 | | 7/2003 |
| WO | WO 95/01617 | A1 | 1/1995 |
| WO | WO9739553 | | 10/1997 |
| WO | WO 99/04685 | | 2/1999 |
| WO | WO9949378 | | 9/1999 |
| WO | WO 99/64974 | A1 | 12/1999 |
| WO | WO 00/52498 | A1 | 9/2000 |
| WO | WO 2004/032019 | A3 | 4/2004 |
| WO | WO 2004/042563 | A3 | 5/2004 |
| WO | WO 2004/102457 | A2 | 11/2004 |
| WO | WO 2005/043402 | A1 | 5/2005 |
| WO | PCT/CA2006/000195 | | 5/2006 |
| WO | PCT/CA2006/000196 | | 5/2006 |
| WO | PCT/CA2006/000197 | | 5/2006 |
| WO | PCT/CA2006/000205 | | 5/2006 |
| WO | WO 2006/049728 | A1 | 5/2006 |
| WO | PCT/CA2006/000198 | | 6/2006 |
| WO | PCT/CA2006/000203 | | 6/2006 |
| WO | PCT/CA2006/000204 | | 6/2006 |
| WO | PCT//CA2006/001479 | | 12/2006 |

OTHER PUBLICATIONS

Rodriquez et al., "Location-Aware Access to Hospital Information and Services", IEEE Transactions on Information Technology in Biomedicine, vol. 8, No. 4, Dec. 2004, pp. 448-455.

Jonathan Collins, RFID Remedy for Medical Errors, RFID Journal, http://www.rfidjournal.com/article/view/961, May 28, 2004, pp. 1-3.

Claire Swedberg, Ford Deploys RFID-Enabled Chargers, RFID Journal, http://www.rfidjournal.com/article/articleview/1348/1/1/, Jan. 19, 2005, pp. 1-3.

Office Action mailed on May 16, 2008 in connection with U.S. Appl. No. 11/065,396.

Office Action mailed on Aug. 19, 2008 in connection with U.S. Appl. No. 11/065,047.

Office Action mailed on Oct. 2, 2008 in connection with U.S. Appl. No. 11/065,046.

Parco Merged Media Corporation: "The Parco Real Time Location System", downloaded from website of Parco Merged Media Corporation: www.parcowireless.com (Portland, Maine, U.S.A.), Feb. 2005 (5 pages).

Parco Merged Media Corporation: "Improving the Availability of Information", downloaded from website of Parco Merged Media Corporation: www.parcowireless.com (Portland, Maine, U.S.A.), Jan. 2005 (8 pages).

Parco Merged Media Corporation: "The Parco Wireless Health Care System (WHCS)", downloaded from website of Parco Merged Media Corporation: www.parcowireless.com (Portland, Maine, U.S.A.), Aug. 2004 (8 pages).

Robert J. Fontana, Ph.D.: "Experimental Results From an Ultra Wideband Precision Geolocation System", downloaded from website of Multispectral Solutions, Inc.: www.multispectral.com (Germantown, Maryland, U.S.A.), Aug. 2004 (9 pages).

Robert J. Fontana et al.: "Ultra-Wideband Precision Asset Location System", downloaded from website of Multispectral Solutions, Inc.: www.multispectral.com (Germantown, Maryland, U.S.A.), Aug. 2004 (5 pages).

Robert J. Fontana et al.: "Commercialization of an Ultra Wideband Precision Asset Location System", downloaded from website of Multispectral Solutions, Inc.: www.multispectral.com (Germantown, Maryland, U.S.A.), Aug. 2004 (5 pages).

Dr. Zeev Weissman: "Indoor Location", downloaded from website of Tadlys Ltd.: www.tadlys.com (Rishon LeZiyyon, Israel), Jul. 2004 (15 pages).

Dongquan, Chen et al., "Wireless local area network in a prehospital environment", BMC Medical Informatics and Decision Making, vol. 4, Aug. 31, 2004, 9 pages.

Office Action mailed on Dec. 4, 2008 in connection with U.S. Appl. No. 11/064,930.

Office Action mailed on Mar. 6, 2009 in connection with U.S. Appl. No. 11/065,396.

Office Action mailed on Mar. 19, 2009 in connection with U.S. Appl. No. 11/065,099.

Office Action mailed on Jun. 12, 2009 in connection with UK Patent Application 0602901.1.

Office Action mailed on Jun. 11, 2009 in connection with U.S. Appl. No. 11/064,930.

Office Action mailed on Sep. 2, 2009 in connection with U.S. Appl. No. 11/065,071.

Office Action mailed on Sep. 16, 2009 in connection with U.S. Appl. No. 11/303,989.

Office Action mailed on Nov. 16, 2009 in connection with U.S. Appl. No. 11/064,930.

USPTO Office Action Summary mailed Dec. 17, 2010 in U.S. Appl. No. 11/065,099.

\* cited by examiner

| EQUIPMENT ID 103 | EQUIPMENT-SPECIFIC TAG ID 105 | EQUIPMENT TYPE 107 | DISPLAY CAPABILITY 109 |
|---|---|---|---|
| | | | |
| | | | |
| | | | |
| | | | |

~35

| CLINICIAN ID 38 | CLINICIAN-SPECIFIC TAG ID 42 | AUTHENTICATION INFORMATION 40 | PROFILE 44 | ACCESS PRIVILEGES 46 |
|---|---|---|---|---|
| | | | | |
| | | | | |
| | | | | |
| | | | | |

~22

| PATIENT | HEALTH HISTORY | DIAGNOSTICS | TEST RESULTS | ADMISSIONS RECORD |
|---|---|---|---|---|
| | | | | |
| | | | | |
| | | | | |
| | | | | |

| EQUIPMENT ID 103 | EQUIPMENT-SPECIFIC TAG ID 105 | EQUIPMENT TYPE 107 | DISPLAY CAPABILITY 109 | AUTHORIZED USERS 1110 | PHYSICAL BOUNDARIES 1112 |
|---|---|---|---|---|---|
| | | | | | |
| | | | | | |
| | | | | | |

| EQUIPMENT ID 103 | EQUIPMENT-SPECIFIC TAG ID 105 | EQUIPMENT TYPE 107 | DISPLAY CAPABILITY 109 | MAXIMUM TRANSMITTED RF POWER 1210 | EXPOSED RF FIELD STRENGTH LIMIT 1220 |
|---|---|---|---|---|---|
| | | | | | |
| | | | | | |
| | | | | | |

← 1235

USE OF LOCATION AWARENESS TO REQUEST ASSISTANCE FOR A MEDICAL EVENT OCCURRING IN A HEALTHCARE ENVIRONMENT

CROSS-REFERENCE TO RELATED APPLICATION

The present application claims the benefit under 35 U.S.C. 119 (e) of a U.S. Provisional Patent Application to Graves et al. entitled "USE OF LOCATION AWARENESS TO ENHANCE COMMUNICATIONS FUNCTIONS IN A HEALTHCARE ENVIRONMENT", Ser. No. 60/651,623, filed on Feb. 11, 2005, hereby incorporated by reference herein.

FIELD OF THE INVENTION

The present invention relates to communications systems and methods having application to a healthcare environment, and benefiting from enhanced functionality and safety due to the availability of location awareness.

BACKGROUND

In recent years, use of electronic methods to store patient records has become more commonplace, both due to ad-hoc actions by physicians and as an industry response to government pressures. To fully exploit the resultant electronic health records (EHR), physicians and other clinicians need to be given access to both read and write these records. However, patient data is of a confidential nature, thus creating the problem of having to balance the need for privacy against the desire to simplify existing access and authentication protocols and procedures, which are often cumbersome.

In addition, a wide range of communications typically take place in a healthcare environment and are characterized by various degrees of criticality from the perspective of both patients and clinicians. The efficiency with which communications occur in a healthcare environment often directly affects the quality of the healthcare services provided to patients and, in some cases, has a critical impact on the condition of patients. For instance, in some situations where a few minutes can represent the difference between life and death for a patient, the efficiency of communications may be a determining factor in saving the patient's life.

Moreover, while wireless technology has the potential to provide the desired improvement in communications efficiency (such as improved clinician-clinician voice contact and delivery of medical information from databases to the clinician at the point-of-care), the electromagnetic radiating nature of this technology has led to concern over interference with sensitive medical equipment.

There is a thus a need in the industry for improvements in communications systems and methods having application in healthcare environments.

SUMMARY OF THE INVENTION

In accordance with a first broad aspect, the present invention seeks to provide a method of requesting assistance for a medical event occurring in a healthcare establishment. The method comprises receiving data regarding a location of the medical event within the healthcare establishment; receiving data regarding a type of the medical event; receiving data regarding at least one wirelessly detectable tag, each one of the at least one wirelessly detectable tag being associated with a respective one of at least one clinician; determining a respective location of each one of the at least one clinician within the healthcare establishment based at least in part on the data regarding the at least one wirelessly detectable tag; identifying at least one particular clinician of the at least one clinician as being eligible to provide assistance for the medical event, based at least in part on the location of the medical event, the type of the medical event, and the respective location of each one of the at least one clinician; and performing an action to cause requesting of assistance for the medical event from each one of the at least one particular clinician.

In accordance with a second broad aspect, the present invention seeks to provide a system for requesting assistance for a medical event occurring in a healthcare establishment. The system comprises a first functional entity adapted to determine a location within the healthcare establishment where the medical event has occurred; a second functional entity adapted to determine, based at least in part on data regarding wirelessly detectable tags associated with respective clinicians, the locations of the clinicians within the healthcare establishment; a third functional entity adapted to identify, based at least in part on the locations of the clinicians and the location where the medical event has occurred, at least one clinician eligible to provide assistance for the medical event; and a fourth functional entity adapted to cause assistance for the medical event to be requested from each one of the at least one clinician eligible to provide assistance for the medical event.

In accordance with a third broad aspect, the present invention seeks to provide a computer-readable storage medium comprising a program element for execution by a computing device to request assistance for a medical event occurring in a healthcare establishment. The program element includes computer-readable program code for determining a location within the healthcare establishment where the medical event has occurred; computer-readable program code for determining, based at least in part on data regarding wirelessly detectable tags associated with respective clinicians, the locations of the clinicians within the healthcare establishment; computer-readable program code for identifying, based at least in part on the locations of the clinicians and the location where the medical event has occurred, at least one clinician eligible to provide assistance for the medical event; and computer-readable program code for causing assistance for the medical event to be requested from each one of the at least one clinician eligible to provide assistance for the medical event.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

In the accompanying drawings:

FIG. 1D shows an example structure of an equipment database, a clinician database and an electronic health record;

FIG. 11 shows an example structure of the equipment database that is enhanced for the purposes of enabling a function that tracks equipment, in accordance with an embodiment of the present invention;

FIG. 12 shows an example structure of the equipment database that is enhanced for the purposes of enabling a function that monitors RF interference, in accordance with an embodiment of the present invention;

DETAILED DESCRIPTION OF EMBODIMENTS

1. First System Architecture

Figure 1A:
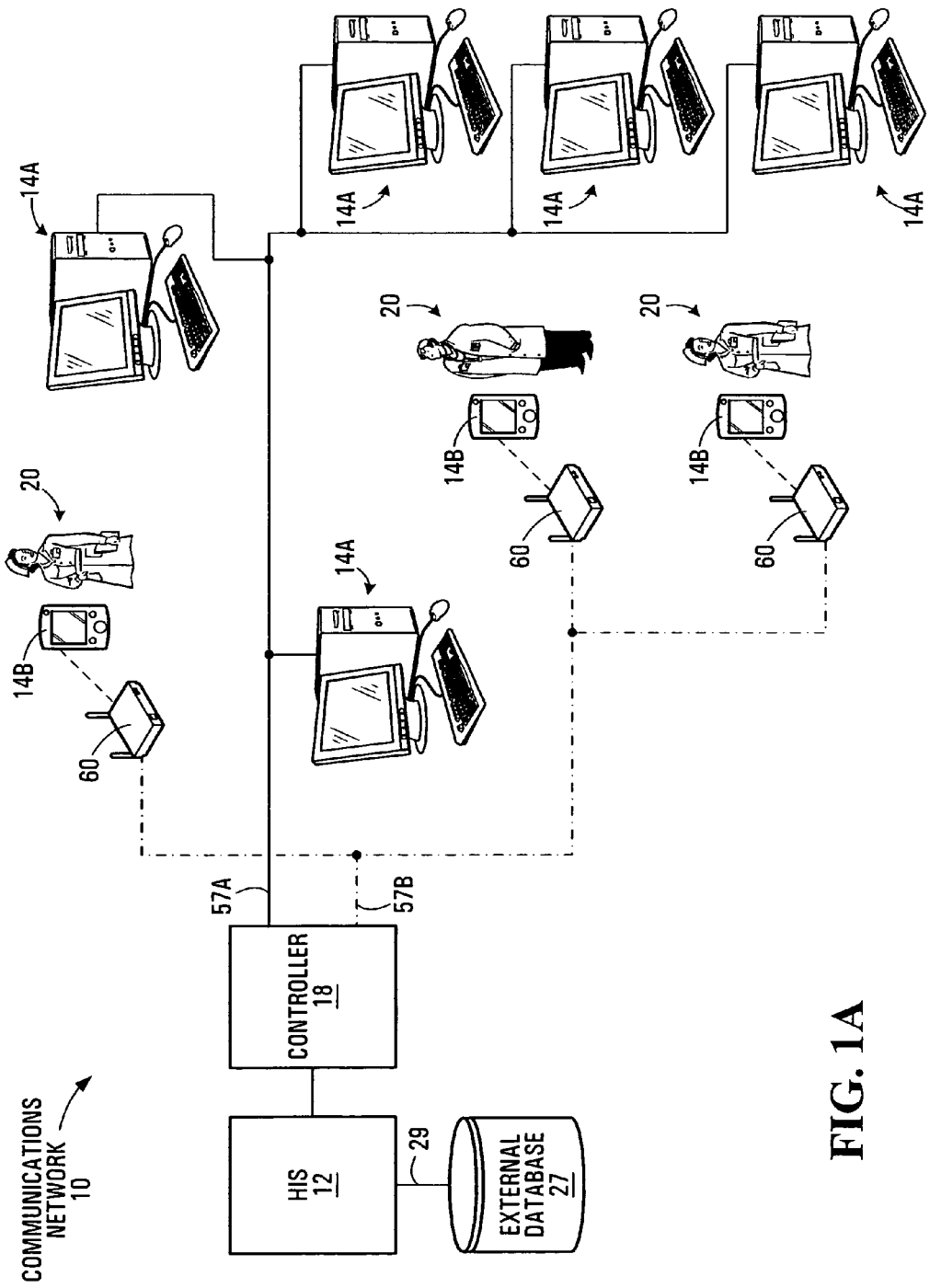
FIGS. 1A and 1B are conceptual block diagrammatic views of a communications network in a hospital, including a plurality of terminals, a hospital information system (HIS) and a controller.
Figure 1B:
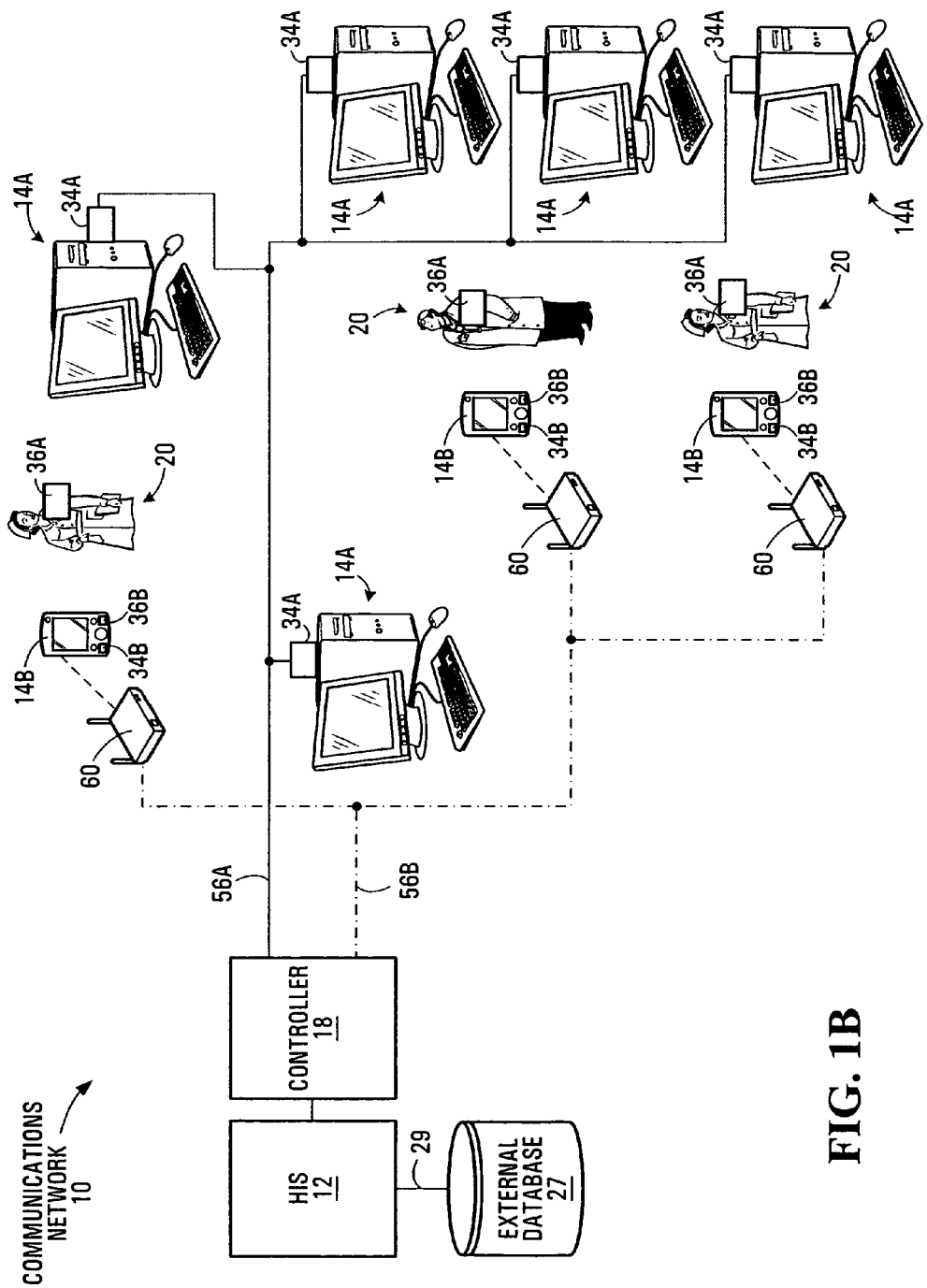

FIGS. 1A and 1B show a conceptual view of a communications network 1 of a healthcare establishment, in accordance with a first example of implementation of the present invention. For ease of reading, the healthcare establishment will hereinafter be referred to as a hospital, but it should be understood that the healthcare establishment may be of any size and may consist of a single building or a campus including one or more buildings or pavilions and possibly one or more adjacent areas such as roads and parking lots.

A plurality of fixed terminals 14A and a plurality of mobile terminals 14B serve as entry points to the communications network 10. The terminals 14A, 14B are accessed by a plurality of "clinicians" 20 who are mobile within the hospital. The term "clinician" is used to denote the broad category of individuals who may require access to the communications network 10 in the execution of their duties pertaining to diagnosis and/or treatment of one or more patient. While not intended to be an exhaustive list, typically clinicians 20 can include physicians, radiologists, pharmacists, interns, nurses, laboratory technicians and orderlies, who are all involved in patient diagnosis and/or treatment. In contrast, hospital administrative management, building facilities staff and janitorial staff are not considered to be "clinicians" under this interpretation.

The communications network 10 also includes a tag/detector subsystem (TDS) 16 connected to a controller 18, which is connected to a healthcare information system (HIS) 12. In the non-limiting example of implementation shown in greater detail in FIG. 1C, the HIS 12 includes a clinician database 22, a patient database 24, a departmental database 26 and an equipment database 35, as well as an authentication entity 28 and a point-of-care (POC) server 30. In addition, the HIS 12 may permit access to a trusted external database 27, for instance a national electronic health record (EHR) database, via a secure link 29.

The aforementioned components of the communications network 10 will now be described in greater detail.

Terminals 14A, 14B

The terminals 14A, 14B allow communication between the clinicians 20 and the HIS 12 via the controller 18. Terminals 14A are fixed-wire terminals, such as stationary terminals or workstations, connected to the controller 18 via communication links 57A. Terminals 14B are mobile terminals, such as handheld units (e.g., personal digital assistant (PDA)) or laptop computers, which communicate with the controller 18 via communication links 57B that include wireless portions. The wireless portions of the communication links 57B are secure links that may be encapsulated within the communications network 10, as would be the case for a wireless local area network (WLAN) using WLAN access points 60. In another embodiment, the wireless portions of the communication links 57B may involve an external network connection, as would be the case when the mobile terminals 14B are cellular phones or cellular data devices.

Each of the terminals 14A, 14B has a display capability, which may be different for different types of terminals. For example, mobile terminals 14B may have display capabilities limited by the necessity of being portable and hence of small size. On the other hand, certain ones of the fixed-wire terminals 14A may have superior display capabilities, not being faced with the same constraints as mobile terminals. For example, some fixed-wire terminals 14A may be uniquely qualified for displaying full diagnostic quality radiology images.

Equipment Database 35

With reference to FIG. 1D, the equipment database 35 stores information on the hospital's equipment such as terminals and medical devices. For example, the equipment database 35 comprises a plurality of fields for each piece of equipment, including a unique equipment identifier 103 (e.g., a serial number) and, in the case of equipment having a "tag" (further information regarding tags is provided herein below), an equipment-specific tag ID 105 associated with a tag that is expected to be associated with that piece of equipment. Still other information regarding the specific piece of equipment may include, inter alia, an equipment type 107 (such as "terminal", "fixed terminal", "mobile terminal", "PDA", "fetal heart monitor", etc.) and a display capability 109 (as described in the preceding paragraph). Still other information may be stored in the equipment database 35, such as a predetermined location of a static piece of equipment, if known.

Clinician Database 22

The clinician database 22 stores information regarding the clinicians 20. In one embodiment, with reference to FIG. 1D, the information regarding a specific clinician 20 includes a unique clinician identifier 38 (e.g., an employee number) for the specific clinician 20, as well as "authentication information" 40 for the specific clinician 20. The authentication information 40 can be, for instance, a password and/or data indicative of a biometric characteristic such as a fingerprint or retina scan of the specific clinician 20. Other information regarding the specific clinician 20 may include a clinician-specific tag ID 42 associated with a tag that is expected to be worn by the specific clinician 20.

(Further information regarding tags is provided herein below.) Still other information regarding the specific clinician 20 may include, inter alia, a profile 44 of the specific clinician 20, which defines certain qualifications of the specific clinician 20, as well as access privileges 46 defining types of information of the HIS 12 that the specific clinician 20 is allowed to access. For example, if the specific clinician 20 is a physician, still further other information regarding the physician can include a list of patients under the responsibility of the physician and/or a list of facilities commonly used by the physician.

Patient Database 24

The patient database 24 stores information on the hospital's patients. In one embodiment, with reference to FIG. 1D, the patient database 24 is configured as a database of electronic health records, whereby the information on each patient is stored as an electronic health record (EHR) 47 of the patient. For example, the EHR 47 of a given patient can include information regarding: the long-term and short-term health history of the patient; the treatment and/or surgical history of the patient; one or more diagnostics on the condition of the patient; ongoing and/or planned treatments or surgery for the patient; results of one of more tests performed on the patient (e.g., blood test results, images from medical imaging techniques (e.g. x-rays, MRI images, etc.), or results from any other conceivable test performed on the patient); as well as other information specific to the patient such as admissions records. Due to the sensitive and confidential nature of this information, access to the information contained in the patient database 24 is subject to various authentication and access privilege verifications, as described in further detail below.

Departmental Database 26

Figure 1C:
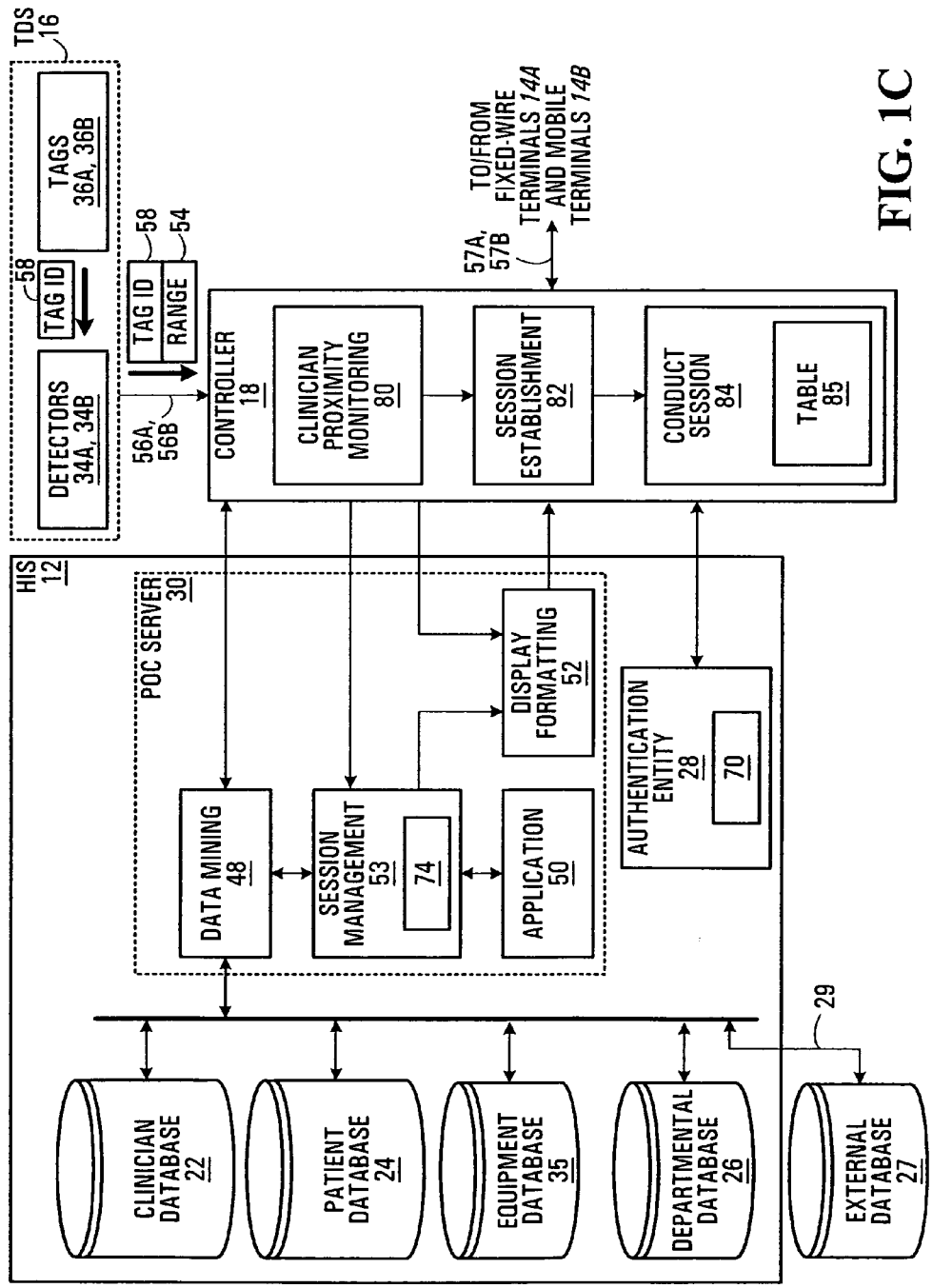
FIG. 1C is a detailed block diagrammatic view of the controller, in accordance with an embodiment of the present invention.

The departmental database 26 (there may be more than one) stores information related to a respective department of the hospital. For instance, the radiology department of the hospital may have its own database storing x-ray images and/or images from other modalities generated as a result of tests performed on patients of the hospital. Similarly, other departments of the hospital, such as the cardiology, chemotherapy, physiotherapy, pharmacy, emergency room, admissions, billing, maintenance, supplies, administration, kitchen, cafeteria, and any other conceivable department of the hospital, may have their own databases storing information pertaining to their respective nature and activities. Again, it should be understood that FIG. 1C depicts only one of many possible architectures for the HIS 12 and that various other architectures are possible without leaving the scope of the present invention. For example, in a possible architecture, the HIS 12 includes multiple departmental databases 26, or includes no departmental database, with all of the information related to the departments of the hospital being stored in a global database (not shown) of the HIS 12.

POC Server 30

The POC server 30 comprises suitable software, hardware and/or control logic for implementing a variety of functions, including a data mining function 48, one or more application functions 50, a display formatting function 52 and a session management function 53.

The purpose of the session management function 53 is to administrate "sessions" for authenticated clinicians interacting with the HIS 12 via the various terminals 14A, 14B in the communications network 10. As will be seen later on, a session established for a given clinician is basically a connection between a given terminal and the HIS 12, allowing the given clinician to run clinical applications at the given terminal or within the HIS 12 and to exchange information with the HIS 12 via the given terminal. The given terminal is said to "support" the session for the given clinician. Administrating a session involves any one or more of establishing, canceling, suspending, resuming and/or changing the data rate, accessible applications and/or accessible information of the session, as a function of various factors such as authentication and authorization levels.

During the course of a session for an authenticated clinician, the clinician may input certain queries, commands or responses, which are processed by the session management function 53, resulting in an action such as: a request for data to be read from or written to the HIS 12 (via the data mining function 48), activation of a clinical application (via the application functions 50), termination or suspension of the session, etc. Data destined for the authenticated clinician during a session is sent via the display formatting function 52. Further detail regarding the manner in which sessions are established between the HIS 12 and the terminals 14A, 14B will be provided herein below.

The purpose of the data mining function 48 is to retrieve from the clinician database 22, the patient database 24, the departmental database 26, the equipment database 35 and the external database 27, information to be made available at the terminals 14A, 14B for sessions established between the HIS 12 and the terminals 14A, 14B. Similarly, the data mining function 48 is also operative to modify information contained in the above-mentioned databases or add new information to these databases as a result of sessions established between the HIS 12 and the terminals 14A, 14B. In this way, the data mining function 48 acts as a conduit between the databases 22, 24, 26, 35, 27 and the clinicians 20.

The purpose of the one or more application functions 50 is to run various applications that may be required to process information exchanged in the course of sessions established between the HIS 12 and the terminals 14A, 14B. Examples of such applications are computerized physician order entry (CPOE) applications, decision information support tools (DIST), and any other conceivable applications that may be required based on the nature of the various sessions that can be established between the HIS 12 and the terminals 14A, 14B.

The purpose of the display formatting function 52 is to format the information to be displayed on the display of a specific one of the terminals 14A, 14B in accordance with the display capability of that display. For instance, the display formatting function 52 may cause an x-ray image to be displayed in its entirety and with high-resolution at one of the fixed terminals 14A having a display of relatively large size and high resolution, yet may cause the same x-ray image to be displayed only in part and/or with low-resolution at one of the mobile terminals 14B (e.g., a PDA) having a display of relatively small size and low resolution. Knowledge of the display capability of each of the terminals 14A, 14B may be stored in the display formatting function 52 or may be obtained from the terminals themselves during sessions between the terminals 14A, 14B and the HIS 12.

The above-mentioned functions of the POC server 30 implement a so-called "thin client" or "semi-thin client" architecture, whereby the bulk of the processing, such as retrieval, modification, addition, and formatting of information as well as running of applications involved in sessions established between the terminals 14A, 14B and the HIS 12, is mainly handled by the POC server 30. In such an architecture, the terminals 14A, 14B basically act as dependent terminals, primarily providing display and input functions. Advantageously, in such an architecture, sensitive information such as information regarding the hospital's patients does not need to be stored in non-volatile form at the terminals 14A, 14B during established sessions, thereby inhibiting access to such sensitive information via a given one of the terminals, should such be stolen or otherwise compromised. However, it is to be understood that, in other examples of implementation, part or all of the processing involved in sessions established between the terminals 14A, 14B and the HIS 12 may be handled by the terminals 14A, 14B.

Tag/Detector Subsystem (TDS) 16

The TDS 16 basically includes a system of tags and tag detectors, with the tags being attached to people (e.g., clinicians) or equipment (e.g., terminals, medical devices) that are to be tracked (e.g., because they are mobile), and the detectors being attached to the entry points into the communications network 10. The tags are referred to as being "wirelessly detectable", in the sense that their presence can be detected by a detector without requiring that a fixed-wire connection be established between the tags and the detector.

As best seen in FIG. 1B, the tags include a first plurality of tags 36A respectively associated with the clinicians 20 and a second plurality of tags 36B respectively associated with the mobile terminals 14B. By way of specific non-limiting example, the tags 36A attached to the clinicians 20 may be in the form of badges clipped to, or sewn into, the clothing of the clinicians 20. As for the tags 36B attached to the mobile terminals 14B, these may take the form of embedded or adhesively mounted devices. Of course, other ways of associating tags 36A to clinicians 20, and associating tags 36B to mobile terminals 14B, will be known to those of ordinary skill in the art and are within the scope of the present invention.

A given tag 36A, 36B operates in such a way as to allow its location and identity to be detected by a compatible detector. For instance, it may employ a brief radio frequency signal that encodes an identifier of the given tag 36A, 36B, hereinafter referred to as a "tag ID" 58. Without being interpreted as a limitation of the present invention, the tags 36A, 36B can be active (i.e. the tag frequently or periodically emits a signal), semi-active (i.e. the tag emits a signal only in response to receiving another signal), or passive (i.e. the tag only reflects a received signal). The decision to use active, semi-active or passive tags depends on various factors such as the required range, precision, and power consumption/battery lifetime/weight considerations. Also, other technologies may be used without departing from the scope of the present invention, such as acoustical, ultrasonic, optical, infrared, etc. As a non-limiting example example, one may use the UWB precision location receivers and tags from Multispectral Solutions, Inc. of Germantown, Md., USA.

The detectors include a first plurality of detectors 34A respectively associated with the fixed-wire terminals 14A and a second plurality of detectors 34B respectively associated with the mobile terminals 14B. The detectors 34A, 34B detects aspects of the location of the tags 36A, 36B as well as the tag ID 58. For instance, with detectors and tags utilizing RF transmission technologies, and depending on the type of tag used, each of the detectors 34A, 34B may include either a receiver for receiving radio frequency signals emitted by active tags, or both a transmitter for emitting radio frequency pulses and a receiver for receiving radio frequency signals emitted (or reflected) by semi-active (or passive) tags in response to the emitted radio frequency pulses.

As shown in FIG. 1B (which can be viewed as an overlay onto FIG. 1A), detectors 34A are connected to the controller 18 via communication links 56A. Since detectors 34A are associated with the fixed terminals 14A, it may prove economical or efficient to use the same physical medium for communication links 57A and 56A. Similarly, detectors 34B are connected to the controller 18 via communication links 56B that may include wireless portions. Since detectors 34B are associated with the mobile terminals 14B, it may prove economical or efficient to use the same physical medium for communication links 57B and 56B. However, this is not a requirement of the present invention.

Moreover, it is noted that in the case of detectors 34B, the associated mobile terminals 14B are also associated with the tags 36B as indicated above. Hence, in some embodiments, it may prove economical or efficient to equip each mobile terminal 14B with a single radio-frequency device that incorporates an individual detector 34B as well as the associated tag 36B. However, this is not a requirement of the present invention.

In view of the above, it will be apparent that the detectors 34A, 34B receive signals from one or more nearby tags 36A, 36B, detect the tag IDs 58 in the received signals and communicate the tag IDs 58 to the controller 18 along a set of communication links 56. The information contained in the tag ID 58 is unique for the various tags 36A, 36B. Assuming that there is a one-to-one physical association between the clinicians 20 and the tags 36A, then the tag ID 58 for the tag 36A attached to a given clinician 20 can contain the clinician identifier 38 of the given clinician 20. (Alternatively, if the clinician identifier 38 needs to be kept confidential, then the tag ID 58 can contain the clinician-specific tag ID 42 for the given clinician 20.) Similarly, if there is a one-to-one physical association between the mobile terminals 14B and the tags 36B, then the tag ID 58 for the tag 36B attached to a given mobile terminal 14B can contain a serial number or MAC address of the given mobile terminal 14B.

In addition to detecting the tag IDs 58 in the signals received from the tags 36A, 36B and forwarding the tag IDs 58 to the controller 18, the detectors 34A, 34B generate range messages 54 indicative of the distance between the tags 36A, 36B and the detectors 34A, 34B. The generation of the range messages 54 can be based on the intensity of the received signals, or on the round-trip travel time of individual tag IDs.

The range messages 54 may contain information permitting the determination of range (distance) between a given detector and a given tag, or they may reflect the result of signal processing at the given detector by virtue of which it was concluded that the given tag is "in proximity" to the given detector. Those skilled in the art will appreciate that still other parameters or characteristics of a signal received at a particular detector may serve as the basis to generate the range messages 54 for a particular tag ID 58 relative to a particular detector 34A, 34B.

It should also be understood that in cases where clinicians 20 are assumed at all times to be using specifically assigned mobile terminals 14B, the need for separate tags 36A, 36B attached to both the clinicians 20 and the mobile terminals 14B may be obviated, as long as the single tag contains the ability to convey authentication data from the clinician, as may be required in order to satisfy security constraints. Rather, a single set of tags (either 36A or 36B) would suffice to enable the various functions described herein.

It will thus be appreciated from the foregoing, as well as from portions of the description to follow, that detection by a particular detector of the tag ID 58 corresponding to a particular tag may lead to a conclusion that a clinician 20 or mobile terminal 14B is somewhere in the vicinity of the particular detector. In the case of a suspected nearby clinician 20, this implied knowledge should be confirmed by way of an authentication process, which will be described in further detail in the next section.

Authentication Entity 28

The authentication entity 28 comprises suitable software, hardware and/or control logic for implementing an authentication process 70, which positively confirms the clinician's identity and which manages access of the clinicians 20 to the HIS 12 via the terminals 14A, 14B. It should be understood that the authentication entity 28 may be a separate entity or it may be integrated to the controller 18 or to the POC server 30, for example.

Figure 2A:
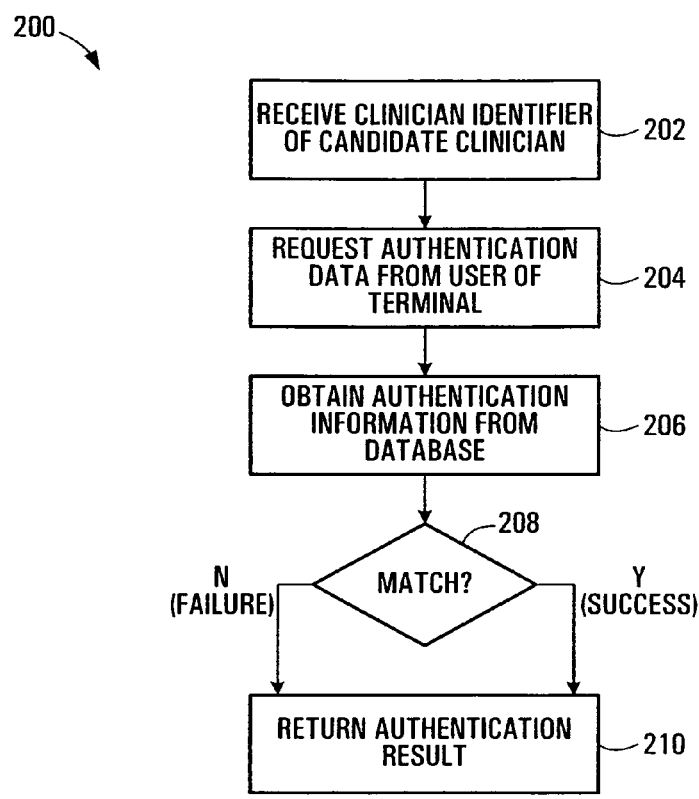
FIG. 2A is a flowchart showing steps in an authentication process performed by an authentication entity in the HIS, in accordance with an embodiment of the present invention.
Figure 2B:
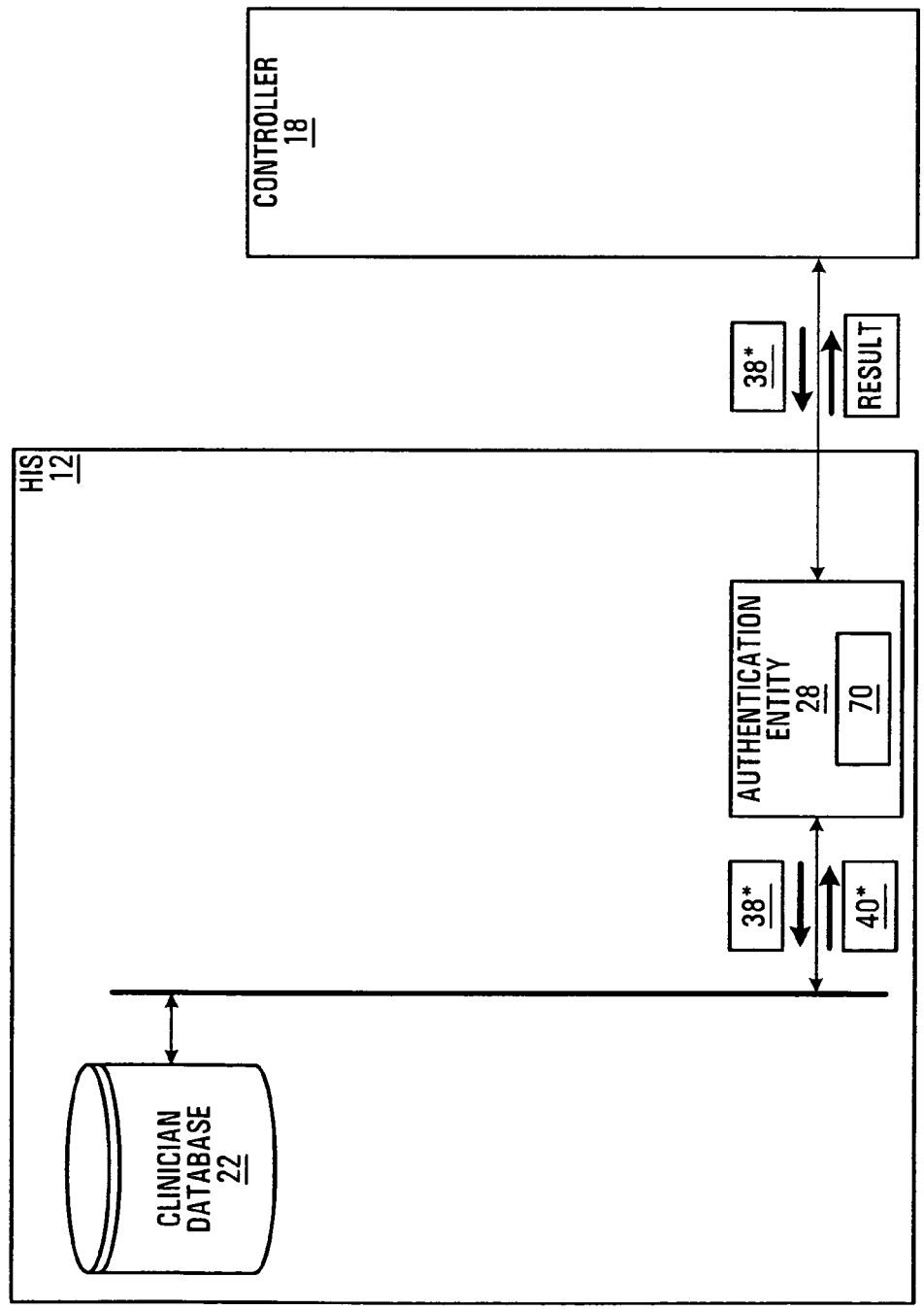
FIG. 2B shows interaction among various elements of the communications network as a result of performing the authentication process, in accordance with an embodiment of the present invention.

The authentication process 70 is now described in greater detail with additional reference to FIGS. 2A and 2B. More particularly, at step 202, the authentication entity 28 receives from the controller 18 the clinician identifier of a candidate clinician 20 who needs to be authenticated. This may be triggered under various conditions described later on in greater detail. Let the clinician identifier of the candidate clinician 20 be denoted 38\* and let the authentication information for the candidate clinician 20 be denoted 40\*.

The authentication process 70 then proceeds to step 204, where authentication data is requested from the candidate clinician 20. One example of authentication data is a password; another example of authentication data is biometric information. To this end, the badges worn by clinicians 20 may optionally be enhanced with a fingerprint reader operative to generate data indicative of a fingerprint of anyone (including of course the clinician himself/herself) touching the fingerprint reader. A non-limiting example of a fingerprint reader that is adequately dimensioned to be incorporated into a badge in the manner contemplated herein is the FingerLoc® AF-S2 fingerprint sensor manufactured by AuthenTec, Inc. Melbourne, Fla., USA, (see also www.authentec.com). The fingerprint of the candidate clinician 20 would be scanned by the sensor and the results of the scan transmitted to the authentication entity 28. The results of the scan may be in the form of a digitized image of the fingerprint or other metrics derived from local processing of the image.

Responsive to receipt of the authentication data, the authentication process proceeds to step 206, where the authentication entity 28 communicates with the clinician database 22 (via the data mining function 48) to obtain, for comparison purposes, the stored authentication information 40\* for the candidate clinician 20. This can be done by supplying to the clinician database 22 the clinician identifier 38\* of the candidate clinician 20, which was supplied by the controller 18 at step 202.

The authentication process 70 then proceeds to step 208, where an authentication result is generated. Specifically, the received authentication data is compared to the stored authentication information 40\* for the candidate clinician 20 as obtained from the clinician database 22 at step 206. The authentication result will be a success when there is a match and a failure otherwise. At step 210, the authentication result is returned to the controller 18, where consequential actions are taken in a manner that will be described in greater detail herein below.

It should be understood that steps 206 and 208 of the authentication process 70 may be replaced by a single step whereby the authentication entity 28 sends the received authentication data to the clinician database 22, prompting the latter to effect the comparison with the stored authentication information 40\* for the candidate clinician 20 and to return the authentication result to the authentication entity 28. This alternative approach may be advantageous from the point of view of data security, since the stored authentication information 40\* for the candidate clinician 20 need not exit the clinician database 22.

It should also be understood that other layers of security and authentication may be provided without departing from the scope of the present invention. For example, the tag IDs 58 may be encrypted to prevent spoofing of the authentication information by a non-valid tag. In addition, or alternatively, the tags 36A can contain memory and processing to associate a clinician's biometric data (such as a fingerprint) to that tag so that authentication is performed locally at the tag either in addition to, or instead of, at the authentication entity 28.

Controller 18

As previously mentioned, the controller 18 is connected to the TDS 16 by the communication links 56A, 56B, to the terminals 14A, 14B by the communication links 57A, 57B, as well as to the authentication entity 28 and to the POC server 30. In this first system architecture, the controller 18 comprises suitable software, hardware and/or control logic for implementing a clinician proximity monitoring process 80 that operates in the background until it detects that a certain condition is satisfied, whereupon further processing operations are performed. The detailed operation of the controller 18 is now described, beginning with the clinician proximity monitoring process 80.

Clinician Proximity Monitoring Process 80

Figure 3A:
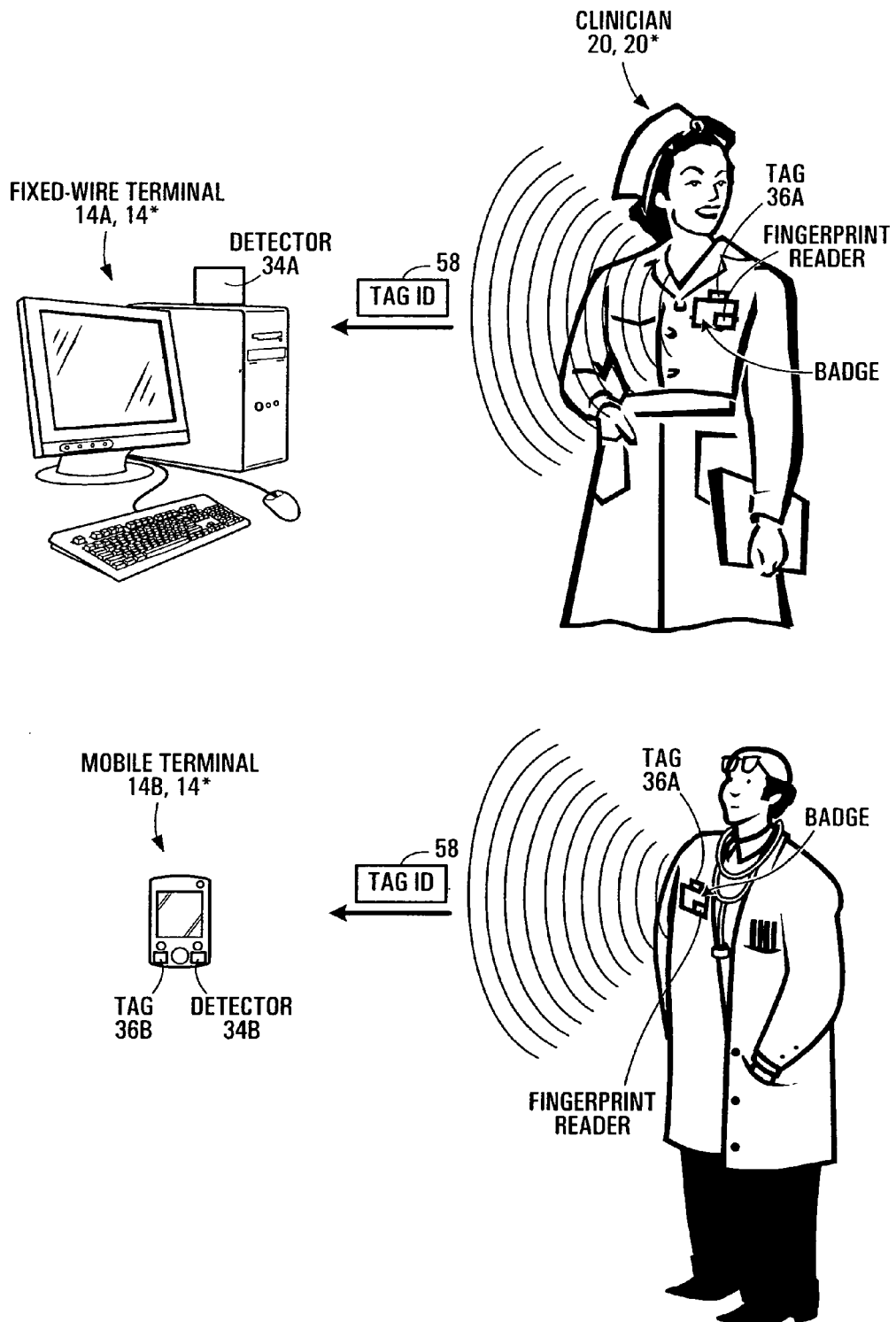
FIG. 3A illustrates two instances of a scenario where a clinician is located in proximity to a terminal of the hospital communications network.

The clinician proximity monitoring process 80 monitors the output of the TDS 16 to decide when individual clinicians 20, for whom sessions have not been established, are considered "in proximity" to individual ones of the terminals 14A, 14B. As will be described later on, being deemed "in proximity" has attributes of distance (usually less than a pre-set threshold value) and may also have attributes of time/duration, since a person transiting past a location has a different intent than someone remaining within a certain distance of a location for a certain duration. In one embodiment, the clinician proximity monitoring process 80 operates in the background until it detects that a trigger condition is satisfied, whereupon further processing operations are performed With reference to FIG. 3A, it is recalled that in this first system architecture, clinicians 20 are associated with tags 36A, and detectors 34A, 34B are terminal-specific. In other words, a given clinician of interest (denoted 20*) being "in proximity" to a given terminal of interest (denoted 14*) amounts to the tag 36A associated with clinician 20* being "in proximity" to the detector 34A, 34B associated with terminal 14*. The ability of the clinician proximity monitoring process 80 to make decisions regarding individual clinicians 20 (including clinician 20*) being in proximity to terminal 14* stems from the processing of tag IDs 58 and range messages 54 received from the TDS 16.

The definition of "proximity" may vary in accordance with operational requirements. In one embodiment, clinician 20* being "in proximity" to terminal 14* may be defined as satisfaction of a computed "proximity condition", which occurs when the estimated distance between clinician 20* and terminal 14* is below a threshold distance, continuously, for at least the duration of a time window. Generally speaking, a judicious choice of distance and/or the distance-time relationship ensures smooth, easy attachment and authentication for clinicians desirous of such events while not triggering "false starts" due to transient clinician traffic passing nearby terminal 14*. Too "close" a distance threshold leads to trouble triggering a greeting message/opportunity to authenticate, while too "far" a distance threshold leads to triggering numerous unnecessary greeting messages, which may ultimately affect existing sessions and/or core system load. Moreover, too brief a "time window" results in increased likelihood of false "in proximity" detections, while too lengthy a "time window" (say more than 1-2 seconds) will make the system seem sluggish and unresponsive. Additionally, the proximity condition may be variable in terms of both distance and duration—for instance a closer distance requiring a shorter time window. Of course, it is within the scope of the present invention to further refine the definition of the proximity condition using additional factors. For instance, such additional factors may include the identity or professional role of clinician 20*, the physical location of static equipment in the hospital and/or the hospital department in which terminal 14* is located.

Figure 3B:
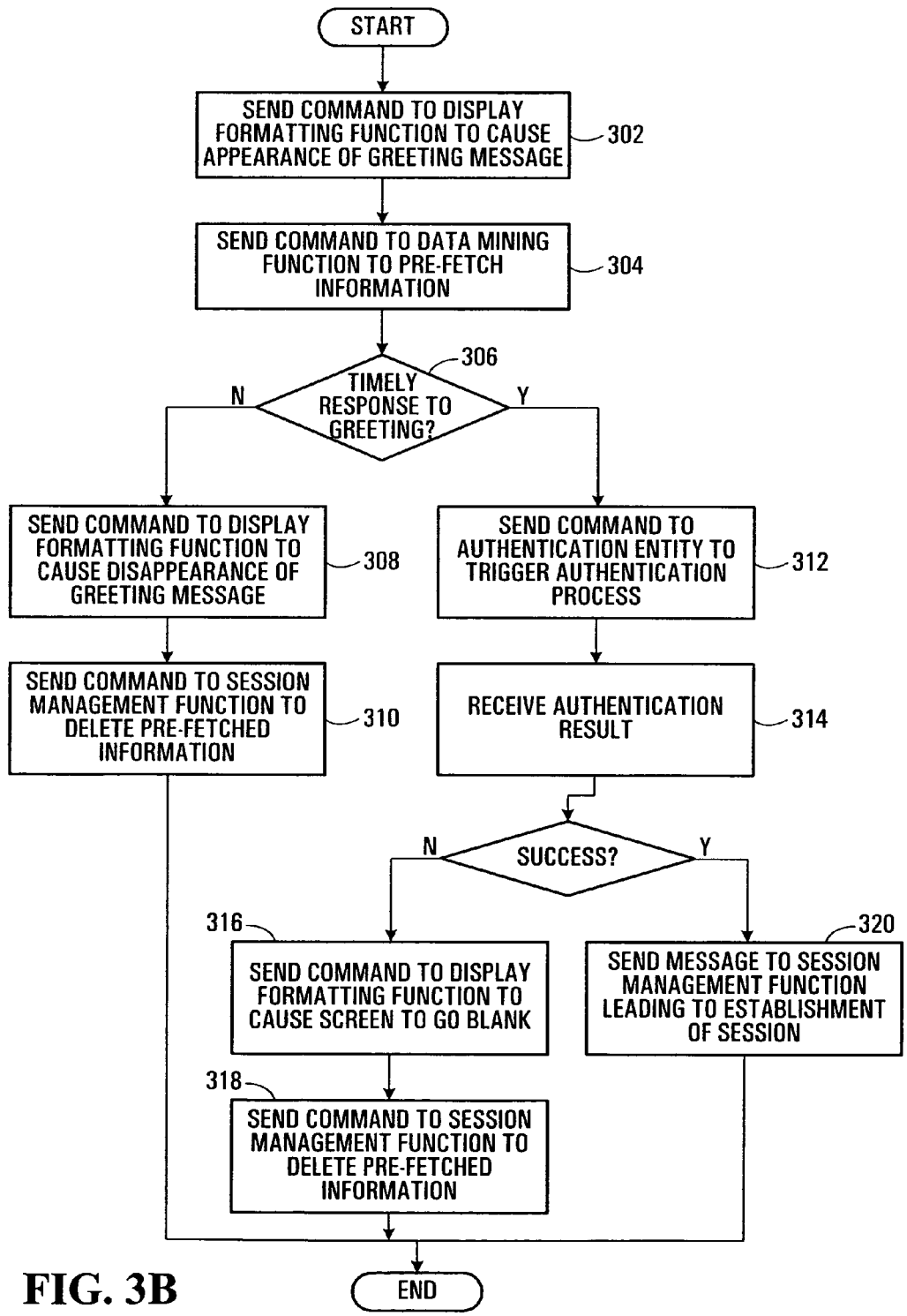
FIG. 3B is a flowchart showing steps in a session establishment process performed by the controller, in accordance with an embodiment of the present invention.
Figure 3C:
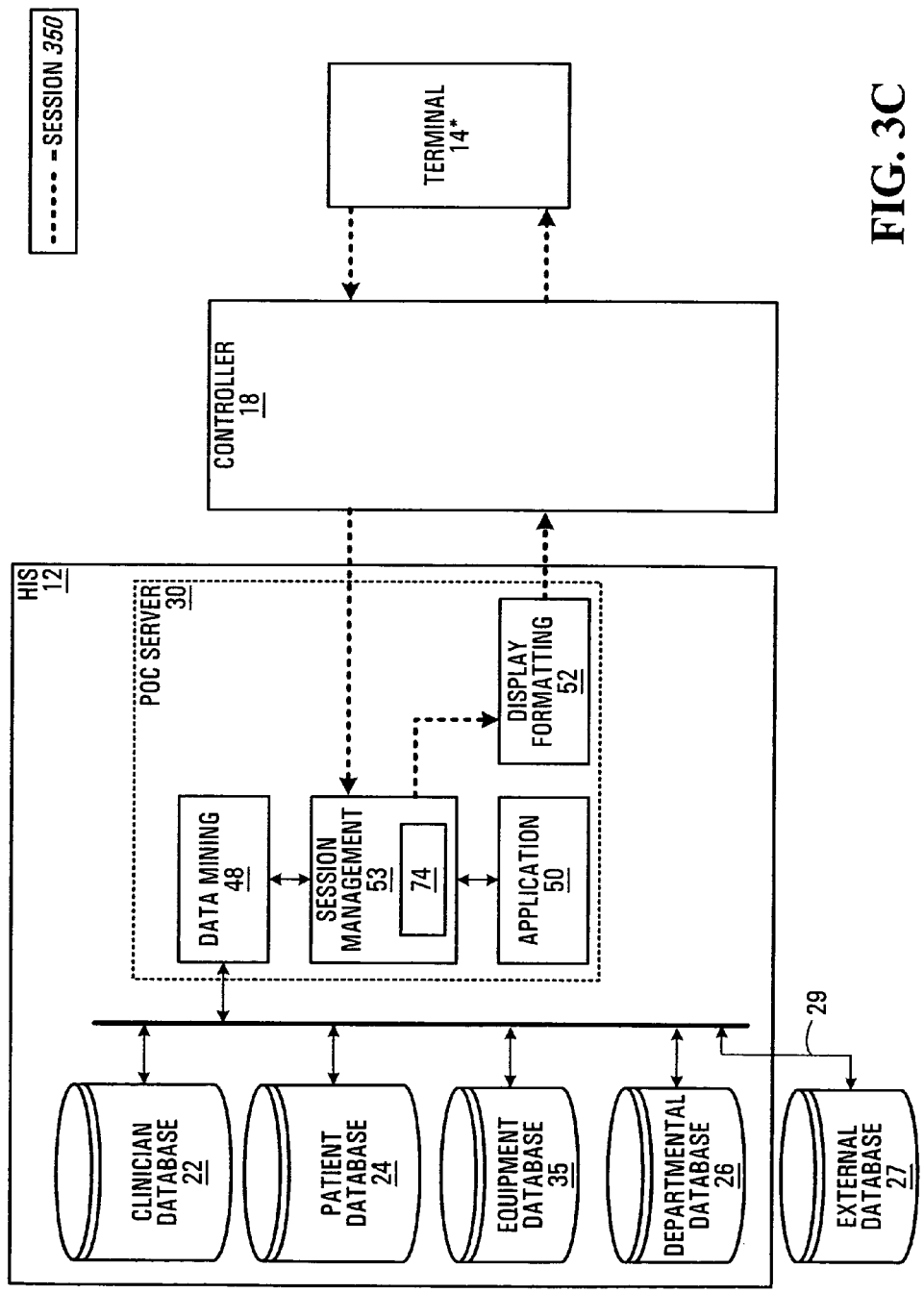
FIG. 3C depicts a path of an established session through elements of the communications network, in accordance with an embodiment of the present invention.

Once the clinician proximity monitoring process 80 has determined that the proximity condition has been satisfied for clinician 20* with respect to terminal 14*, the controller 18 executes a session establishment process 82, shown in FIG. 1C and now described with additional reference to FIGS. 3B and 3C.

Session Establishment Process 82

Although the clinician proximity monitoring process 80 has deemed clinician 20* to be in proximity to terminal 14*, his or her intent to use terminal 14* has not yet been established. Accordingly, at step 302 of the session establishment process 82, the controller 18 sends a command to the display formatting function 52, causing the latter to display a greeting message on the display of terminal 14* for clinician 20*. For instance, assuming that clinician 20* is a certain Dr. Jones, the greeting message displayed on the display of terminal 14* may be "Welcome Dr. Jones. Please confirm your identity if you wish to use this terminal.", or any conceivable variant thereof. It is noted that since the identity of terminal 14* is considered to be known by the display formatting function 52, its display capabilities will also be known a priori.

Meanwhile, or following execution of step 302, the controller 18 proceeds to step 304, which causes execution of a preliminary processing operation in anticipation of potential establishment of a session for clinician 20* between the HIS 12 and terminal 14*. In a non-limiting example of a preliminary processing operation, the controller 18 sends a command to the data mining function 48 in the POC server 30, causing the latter to pre-fetch information from the clinician database 22, the patient database 24, the departmental database 26, the equipment database 35 and/or the external database 27 in anticipation of potential establishment of a session for clinician 20*.

In the specific non-limiting case where clinician 20* is a physician, the pre-fetched information may include one or more of the profile of the physician; the access privileges of the physician; a list of patients under the responsibility of the physician; information (e.g., an electronic health record 47, or a portion thereof) related to one or more patients in the list of patients under the responsibility of the physician; and information related to one or more patients in proximity to terminal 14*.

It should be appreciated that the identity of patients in proximity to terminal 14* can be obtained in various ways. In one embodiment, terminal 14* is one of the fixed-wire terminals 14A, and the knowledge of nearby patients is obtained on the basis of information stored in the patient database 24, the departmental database 26, the equipment database 35 and/or the external database 27, such as the location of terminal 14* within the hospital and the location of each patient's bed within the hospital. In another embodiment, each patient is provided with a tag such as a tag in the form of a bracelet worn by the patient. In such an embodiment, the tag of a patient interacts with the detector 34A of terminal 14* in the aforementioned manner, allowing the controller 18 to learn of the relative proximity of each patient to terminal 14*. Alternatively, a standard RF-ID tag could be used, although in such an embodiment, there may be limitations in terms of range that need to be taken into consideration.

In addition, the information that is pre-fetched may also be organized or filtered by using the clinician's location and identity. For example, the list of patients for a particular physician may be sorted by those whose assigned beds are nearest the particular physician.

The information that is pre-fetched by the data mining function 48 is kept in a holding location 74 that is accessible to the session management function 53 but as yet inaccessible to clinician 20* deemed to be in proximity to terminal 14*. More specifically, the pre-fetched information will become available to clinician 20* once a session is established for clinician 20*, but such a session has not yet been established because (1) the intent of clinician 20* to use terminal 14* is still not known; and (2) clinician 20* has not been authenticated (for example, it has not yet been confirmed that the individual who is presumed to be Dr. Jones by virtue of information received from the TDS 16 really is Dr. Jones).

At step 306, the controller 18 continues to attempt to establish the intent of clinician 20* to use terminal 14* by waiting for input from clinician 20* in response to the greeting message. At this point, two basic outcomes are possible. In the first outcome, clinician 20* ignores the greeting message. Accordingly, the controller 18 will detect an absence of a response for a predetermined amount of time and will conclude that there is no intent by clinician 20* to use terminal 14*. This leads to execution of step 308, whereby a command is sent to the display formatting function 52, causing the greeting message to disappear from the display of terminal 14*. In addition, the controller 18 performs step 310, which is optional, whereby a command is sent to the session management function 53 to delete the pre-fetched information in the holding location 74 in order to avoid potential security leaks due to hacking. In an alternative embodiment, step 310 is replaced by a different series of steps, whereby the pre-fetched data may be held in the holding location 74 until clinician 20* leaves the vicinity of terminal 14*, so that the pre-fetched data can be delivered quickly, should clinician 20* later decide, during his/her patient encounter, to initiate a session. Thus, even though a session is not established for clinician 20*, it can be said that the pre-fetched data is held in trust for clinician 20*.

However, in the alternate outcome of step 306, clinician 20* does indeed respond to the greeting message in a timely manner, e.g., by pressing a key or touching the screen. This is interpreted by the controller 18 as an intent to use terminal 14*, and leads to step 312. Specifically, the controller 18 sends a message to the authentication entity comprising the clinician identifier of clinician 20*, denoted 38*. Receipt of clinician identifier 38* by the authentication entity 28 triggers the authentication process 70 previously described with reference to FIGS. 2A and 2B, which typically involves the submission of authentication data 40* by clinician 20* (e.g., via a fingerprint reader).

In an alternative embodiment, steps 302 and/or 312 may be omitted. For example, without having executed step 302, the controller 18 proceeds to step 304, which causes execution of a preliminary processing operation in anticipation of potential establishment of a session for clinician 20* between the HIS 12 and terminal 14*. At this point, without having displayed a greeting message, the controller 18 is attentive to clinician 20* requesting a session by touching a fingerprint reader on clinician 20*'s badge. This will be interpreted by the controller 18 as an intent to use terminal 14* as well as a submission of authentication data 40* by clinician 20*. In other words, steps 302 and 312 can be omitted if the mere fact that authentication data is submitted by clinician 20* serves to confirm the intent of clinician 20* to use terminal 14*. Hence, the use of greetings is not required. Of course, whether or not a greeting message is used is a design consideration, and both approaches are to be considered as being within the scope of the present invention.

In either case, at step 314, the controller 18 receives an authentication result from the authentication entity 28. If the authentication result is a failure, then clinician 20* may be allowed to make one or more additional attempts to authenticate himself or herself in accordance with security policies in effect. However, if authentication fails each time, then clinician 20* is denied access to the information contained in the HIS 12, i.e. no session is established for clinician 20*. Specifically, at step 316, the controller 18 sends a command to the display formatting function 52, causing a change in the display of terminal 14* (e.g., blank screen). In addition, the controller 18 performs step 318, whereby a command is sent to the session management function 53 to delete the pre-fetched information in the holding location 74 in order to avoid potential security leaks due to hacking.

On the other hand, the authentication result may be a success, in which case the controller 18 proceeds to step 320, where additional processing is performed in order to effect establishment of a session for clinician 20*. Specifically, the controller 18 sends a message to the session management function 53 in the POC server 30, which indicates to the session management function 53 that the clinician who is deemed to be at terminal 14* is permitted to access the pre-fetched information in the holding location 74 as well as possibly other information in the HIS 12. With specific reference to FIG. 3C, the session management function 53 establishes a connection 350 between the HIS 12 and terminal 14*, allowing clinician 20* to exchange information with the HIS 12 via terminal 14*. The connection 350 is hereinafter referred to as a "session", while terminal 14* is said to "support" the session 350 for clinician 20*.

It will thus be appreciated that establishment of the session 350 for clinician 20* at terminal 14* has been facilitated by (1) preparing information in anticipation of the intent of clinician 20* to use terminal 14*, thereby reducing the real-time computational load of the POC server 30 and other elements of the HIS 12; and (2) simplifying the log-in procedure for clinician 20* to a "confirmation of identity" procedure, whereby clinician 20* is simply required to provide data for his or her authentication; this can advantageously be done by clinician 20* touching a fingerprint reader on his or her badge.

It should also be understood that, in some situations, two or more clinicians 20 may be in proximity to terminal 14* at a given instant. In those situations, the controller 18 may then cause the POC server 30 to pre-fetch information related to each one of the nearby clinicians 20 in anticipation of potential establishment of a session for one or more of these individuals at terminal 14*. In cases where more than one of the nearby clinicians 20 simultaneously wish to use terminal 14*, the controller 18 may effect establishment and management of a session for a given one of those individuals based on a "first to authenticate" basis or based on an access priority for each one of those individuals (e.g. the access privileges of the nearby clinicians 20 may specify that one, e.g., a doctor, has access priority over the other, e.g., a nurse, etc.).

Conduct Session Process 84

Once the session 350 is established, the controller 18 enters a "conduct session" process 84 for the session 350, which is transparent to most of the goings on between clinician 20* and the session management function 53. For example, the conduct session process 84 transparently allows the session management function 53 to implement a graphical user interface (GUI) that presents information and applications available for use by clinician 20* during the session 350. Of course, the actual display of information on terminal 14* will continually be formatted by the display formatting function 52 in accordance with the display capabilities of terminal 14*.

During the session 350, clinician 20* may perform a variety of activities leading to any one of the following non-limiting example scenarios A- through D-.

A- Provide Traditional Point-of-Care Services

Consider the case where clinician 20* is a physician and terminal 14* is a fixed-wire terminal near the bed of a particular patient. In this scenario, the physician accesses one of the application functions 50, which allows the physician to retrieve information from, or add observations and diagnostic information to, the electronic health record 47 of the patient, order a certain treatment or test to be given to the patient, use various application functions 50 such as decision information support tools (DIST), etc.

B- Perform Location-Based Point-of-Care Functions

Consider the case where terminal 14* is a mobile terminal, such as a PDA, which has inferior display capabilities to those required for a particular function (e.g., viewing X-ray images). In this scenario, clinician 20* accesses a location-based POC function (e.g., one of the application functions 50 in the POC server 30, or a separate function in the controller 18) which informs clinician 20* of the nearest available terminal having the required display capabilities.

Specifically, the indication provided by location-based POC function can be based on knowledge of the particular communications link 57B and WLAN access point 60 that the PDA (i.e., terminal 14*) is using to communicate with the POC server 30, thereby allowing a list of terminals in the "coverage zone" of the WLAN access point 60 (or of a plurality of WLAN access points) to be identified. Combined with knowledge at the POC server 30 of which of the terminals in the list are available for use, the capabilities of these terminals and the display quality required by the image to be viewed, this allows identification of the nearest available terminal having the required display capability. Let this nearest available terminal be denoted 14+. As a possible option, the location-based POC function may allow clinician 20* to "reserve" terminal 14+ for a short period of time, say 2 minutes (to cover the estimated walking time of clinician 20* to reach terminal 14+).

C- Explicitly Terminate the Session

Consider the case where clinician 20* wishes to terminate the session 350. In this scenario, clinician 20* interacts with the session management function 53 to perform a log-off procedure to terminate the session 350. For example, this can be effected by entering a log-off command at terminal 14*, e.g., by clicking on a log-out icon on the display of terminal 14*. This command is detected by the session management function 53 which, in response, sends a command to the display formatting function 52, causing a change in the display of terminal 14* (e.g., blank screen). In addition, the session management function 53 deletes session-related information it may have stored (such as pre-fetched information in the holding location 74).

D- Explicitly Suspend the Session

Consider the case where clinician 20* wishes to suspend the session 350 for various reasons (e.g., snack break, migration to another terminal, etc.). In this scenario, clinician 20* interacts with the session management function 53 to trigger a session suspend process to suspend the session 350. For example, this can be effected by entering a suspend command at terminal 14*, e.g., by clicking on a suspend icon on the display of terminal 14*. This command is detected by the session management function 53 which, in response, sends a command to the display formatting function 52, causing a change in the display of terminal 14* (e.g., blank screen). However, the session management function 53 does not delete session-related information, since the session may be resumed by clinician 20* at a later time in a variety of ways.

If the session 350 remains suspended for a considerable length of time (e.g., beyond a certain threshold such as 10 minutes) without having been resumed in one of the variety of ways alluded to above, then the session suspend process in the session management function 53 may autonomously terminate the session 350, which will result in deletion of session-related data such as the pre-fetched data in the holding location 74.

Although it is transparent for most of the activities conducted during the session 350, the conduct session process 84 nevertheless continues to monitor the information from the TDS 16 in order to detect certain conditions of clinician-terminal proximity and terminal-terminal proximity. Specifically, during the session 350, clinician 20* may perform a variety of activities in addition to the above, which may lead to one of the following non-limiting example scenarios E- through G-.

E- Move Away From Terminal 14*

Consider the case where clinician 20* leaves the vicinity of terminal 14* without having terminated or suspended the session 350. One situation in which this may occur is when clinician 20* has identified (or has been directed to) a nearby terminal with superior display capabilities (see B- above) and heads towards that terminal. Another situation in which this may occur is when clinician 20* simply forgets to terminate or suspend the session 350.

In each of these and myriad other example scenarios, the conduct session process 84 will detect, using the data available from the TDS 16, that clinician 20* is no longer within a certain distance of terminal 14*. More generally, clinician 20* can be said to satisfy a computed "remoteness condition".

However, it is not yet clear whether clinician 20* did or did not intend to terminate the session. Thus, instead of terminating the session immediately, the conduct session process 84 causes the session to be suspended by causing the session management function 53 to autonomously execute the session suspension process (see D- above).

Clearly, the autonomous suspension of the session 350 based on deeming clinician 20* to have left the vicinity of terminal 14* reduces the potential of confidential information being viewed at terminal 14* by a patient, passerby or unauthorized clinician, as well as reduces the possibility of undesired access to the HIS 12 via terminal 14* without having clinician 20* nearby. The overall effect is an increase in the security of the HIS 12 and the information contained therein.

F- Appear in Proximity to a Terminal (With Previously Suspended Session)

Figure 4:
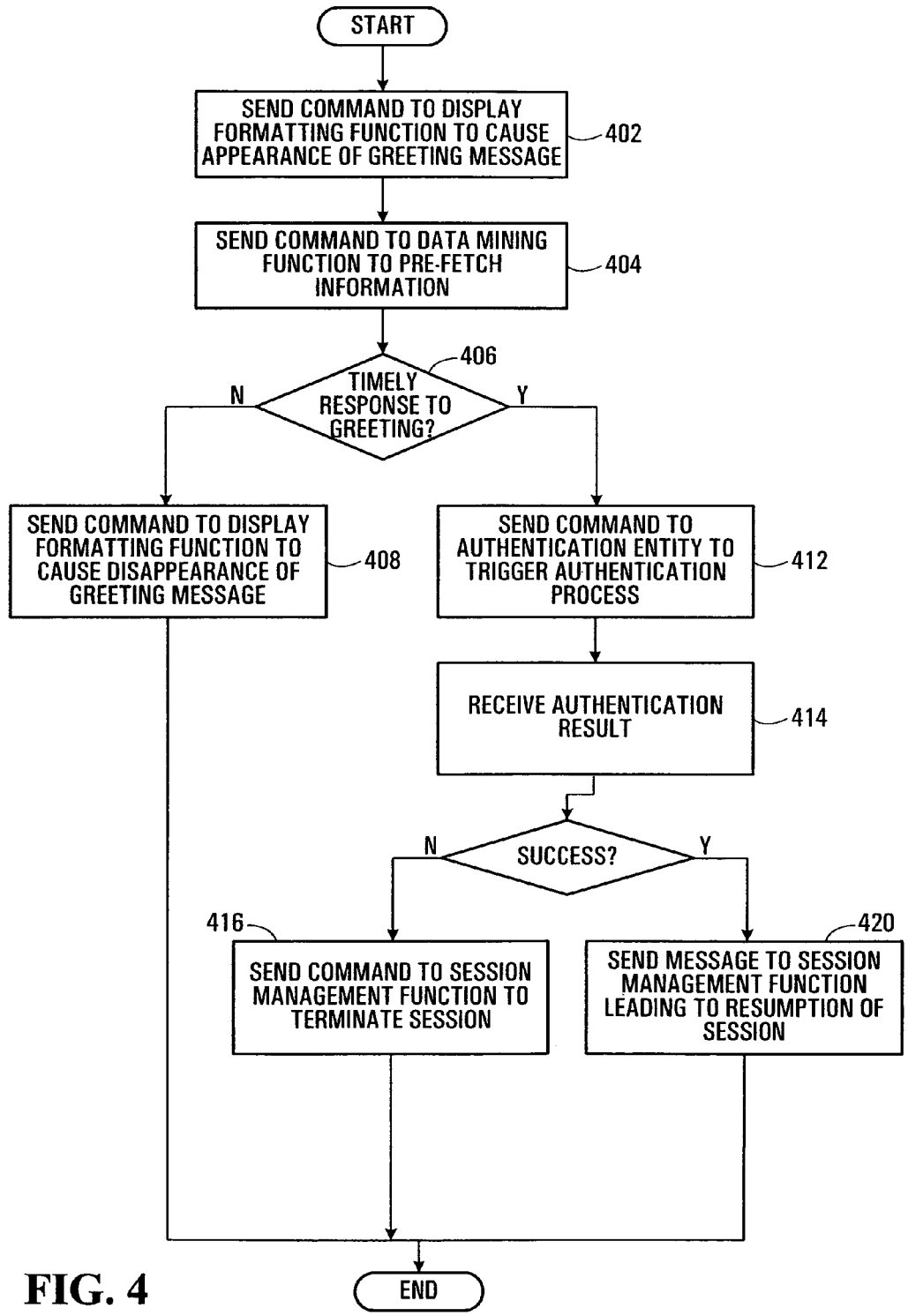
FIG. 4 is a flowchart showing steps in a session resumption process performed by the controller, in accordance with an embodiment of the present invention.

Consider the case where the session 350 has been suspended as described herein above (e.g., either by explicit action on the part of clinician 20* or autonomously as a result of clinician 20* having left the vicinity of terminal 14*). In addition, clinician 20* approaches a terminal, denoted 14+, which may or may not be the same terminal 14* as the one previously used by clinician 20* at the time the session 350 was suspended. The conduct session process 84 will detect, using the data available from the TDS 16, that clinician 20* is in proximity to terminal 14+. This triggers a session resumption process, now described with reference to FIG. 4.

At this stage, it is not yet known whether clinician 20* intends to use terminal 14+. Thus, the conduct session process 84 begins by establishing the intent of clinician 20* to access the HIS 12 at terminal 14+. Specifically, at step 402, the conduct session process 84 sends a command to the display formatting function 52, causing the latter to display a greeting message on the display of terminal 14+. Since the session 350 is in a suspended state, the greeting message may be adapted to reflect this fact. For instance, assuming that clinician 20* is still presumed to be Dr. Jones, the greeting message displayed on the display of terminal 14+ may be "Welcome Dr. Jones. Please confirm your identity if you wish to resume your session at this terminal.", or any conceivable variant thereof. It is noted that since the identity of terminal 14+ is considered to be known a priori by the display formatting function 52, its display capabilities will also be known. Of course, if terminal 14+ is different from terminal 14*, its display capabilities may be different as well. This leads to the advantageous situation where the information displayed to clinician 20* is tailored to the terminal in use.

Meanwhile, or following execution of step 402, the controller proceeds to step 404, where a preliminary processing operation is caused to take place. In a non-limiting example of a preliminary processing operation, the conduct session process 84 causes a command to be sent to the data mining function 48 in the POC server 30, causing the latter to pre-fetch information from the clinician database 22, the patient database 24, the departmental database 26, the equipment database 35 and/or the external database 27. Now, it is recalled that the session 350 for clinician 20* has been suspended. Hence, portions of the preliminary processing operation that would otherwise be required are not needed.

Specifically, in the case where clinician 20* is a physician, the pre-fetched information which is already in the holding location 74 due to the session 350 having been previously established may include one or more of the profile of the physician; access privileges of the physician; a list of patients under the responsibility of the physician; and information (e.g., an electronic health record 47, or a portion thereof) related to one or more patients in the list of patients under the responsibility of the physician. Thus, the preliminary processing operation performed at step 404 can be limited to other information specifically related to terminal 14+. For example, this information may relate to one or more patients in proximity to terminal 14+. (If terminal 14+ is the same as terminal 14\*, then even this last piece of information does not need to be pre-fetched during execution of step 404.)

The information that is pre-fetched by the data mining function 48 during step 404 is added to the other information in the holding location 74 that is accessible to the session management function 53 but as yet inaccessible to clinician 20\*. More specifically, the pre-fetched information will become available to clinician 20\* once the session 350 is resumed, but it is not yet appropriate to resume the session 350 because (1) the intent of clinician 20\* to use terminal 14+ is not known; and (2) clinician 20\* has not been authenticated (in this example, it has not yet been confirmed that the individual who is presumed to be Dr. Jones by virtue of information received from the TDS 16 really is Dr. Jones).

From this point on, the remainder of the steps performed by the conduct session process 84 are similar, although sometimes not identical, to steps 306-320 described previously with reference to FIG. 3A. At step 406, the conduct session process 84 continues to attempt to establish the intent of clinician 20\* to use terminal 14+ by waiting for input from clinician 20\* in response to the greeting message. At this point, two basic outcomes are possible. In the first outcome, clinician 20\* ignores the greeting message. Accordingly, the conduct session process 84 will detect an absence of a response for a predetermined amount of time and will conclude that there is no intent by clinician 20\* to use terminal 14+. This leads to execution of step 408, whereby a command is sent to the display formatting function 52, causing the greeting message disappear from the display of terminal 14+. However, no command is issued to cause deletion of the pre-fetched information in the holding location 74, since there is an underlying assumption that clinician 20\* will eventually wish to resume the session 350, although perhaps not at terminal 14+. Rather, deletion of pre-fetched information related to the suspended session 350 may occur for other reasons, such as the amount of time during which the session 350 has been suspended (see D- above).

When clinician 20\* does indeed respond to the greeting message in a timely manner, e.g., by pressing a key or touching the screen, this is interpreted by the conduct session process 84 as an intent to use terminal 14+, and leads to step 412. Specifically, the conduct session process 84 causes a message to be sent the authentication entity 28, comprising the clinician identifier 38\* of clinician 20\*. Receipt of the clinician identifier 38\* by the authentication entity 28 triggers the authentication process 70 previously described with reference to FIGS. 2A and 2B, which typically involves the submission of authentication data by clinician 20\* (e.g., via a fingerprint reader). It should be understood that step 412 can be omitted if the submission of authentication data (e.g., touching the fingerprint reader) is itself used to confirm one's intent to use terminal 14+.

In either case, at step 414, the conduct session process 84 receives an authentication result from the authentication entity 28. If the authentication result is a failure, then clinician 20\* may be allowed to make one or more additional attempts to authenticate himself or herself in accordance with security policies in effect. However, if the authentication result is a failure each time, then clinician 20\* is denied access to the information contained in the HIS 12, i.e. the session 350 is not resumed. In fact, the conduct session process 84 may go so far as to cause termination of the suspended session 350 by issuing a command at step 416. This command is detected by the session management function 53 which, as previously described (see C- above), sends a command to the display formatting function 52, causing a change in the display of terminal 14\* (e.g., blank screen) and deletes session-related information it may have stored (such as pre-fetched information in the holding location 74).

On the other hand, the authentication result may be a success, which leads to resumption of the session 350 for clinician 20\*. Specifically, at step 420, the conduct session process 84 causes a message to be sent to the session management function 53 in the POC server 30, which indicates to the session management function 53 that the clinician deemed to be at terminal 14+ should be permitted to regain access to the pre-fetched information in the holding location 74 as well as other information in the HIS 12. The session management function 53 then establishes a new connection, this time between the HIS 12 and terminal 14+, allowing clinician 20\* to exchange information with the HIS 12 and perform the various other functions referred to above. The new connection represents a resumed version of the once suspended session 350, and is now supported by terminal 14+.

It will thus be appreciated that resumption of a session for clinician 20\* at terminal 14+ has been facilitated by (1) relying on pre-fetched information in anticipation of the clinician's intent to use terminal 14+, thereby reducing the real-time computational load of the POC server 30 and other elements of the HIS 12; and (2) simplifying the re-log-in procedure for clinician 20\* to a "confirmation of identity" procedure, whereby clinician 20\* is simply required to provide data for his or her authentication; this can advantageously be done by touching a fingerprint reader on his or her badge.

G- Appear in Proximity to a New Terminal 14+, Accompanied by Terminal 14\* (Which Continues to Support an Ongoing Session)

Figure 5A:
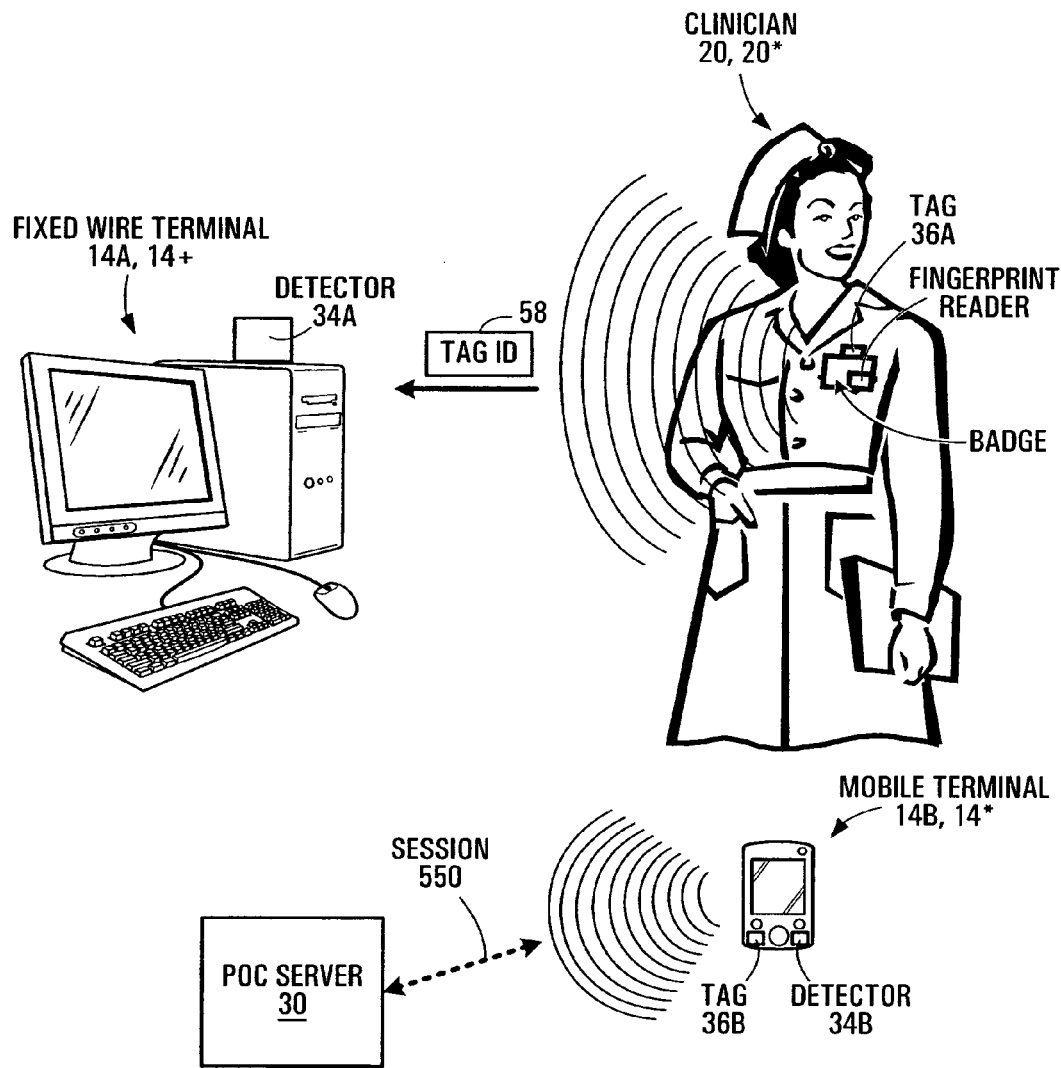
FIG. 5A illustrates a scenario in which a clinician who has an established session with one terminal of the communications network is located in proximity to a second terminal of the communications network.

With reference to FIG. 5A, consider the case where clinician 20\* approaches a new terminal, denoted 14+, while a session 550 is ongoing between the HIS 12 and terminal 14\*. One situation in which this may occur is when clinician 20\* is a physician communicating with the HIS 12 through the physician's PDA (in this case terminal 14\* which supports the session 550) and the physician wishes to view certain information on a fixed terminal with advanced display capabilities (in this case terminal 14+ which is being approached). Of course, it should be understood that the following description also applies to the case where the terminal being approached (i.e., terminal 14+) is a mobile terminal.

Figure 5B:
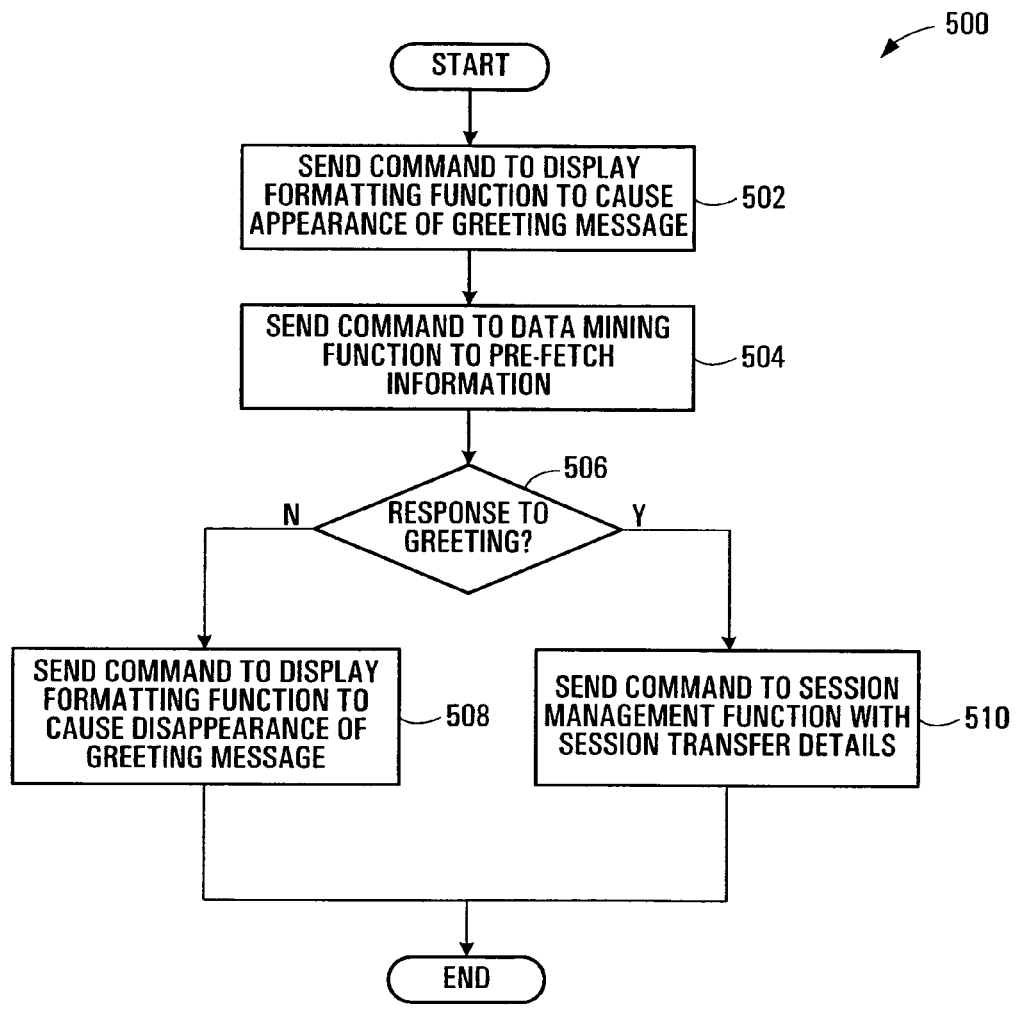
FIG. 5B is a flowchart showing steps in a session transfer process performed by the controller, in accordance with an embodiment of the present invention.

Based on data available from the TDS 16, the conduct session process 84 detects that terminal 14\* is in proximity to terminal 14+. This causes the conduct session process 84 to trigger a live session transfer process, now described with reference to the flowchart in FIG. 5B. Specifically, at step 502, the conduct session process 84 causes a command to be sent to the display formatting function 52, which causing the latter to display a greeting message on the display of terminal 14+ for clinician 20\*. For instance, assuming that clinician 20\* is Dr. Jones, the greeting message displayed on the display of terminal 14+ may be "Welcome Dr. Jones. Please confirm your desire to transfer your session to this terminal.", or any conceivable variant thereof. It is noted that since the identity of terminal 14+is known to the display formatting function 52, its display capabilities will also be known.

Meanwhile or following execution of step 502, the conduct session process 84 executes step 504, whereby a preliminary processing operation is performed. In a non-limiting example of a preliminary processing operation, the conduct session process 84 causes a command to be sent to the data mining function 48 in the POC server 30, causing the latter to pre-fetch information from the clinician database 22, the patient database 24, the departmental database 26, the equipment database 35 and/or the external database 27. However, it is recalled that the session 550 for Dr. Jones is ongoing between the HIS 12 and terminal 14*. Therefore, certain elements of the preliminary processing operation that would otherwise be required are not needed.

For example, where clinician 20* is a physician, the information which is already in the holding location 74 by virtue of prior establishment of the session 550 includes one or more of: the profile of the physician, access privileges of the physician, a list of patients under the responsibility of the physician, and information (e.g., an electronic health record 47, or a portion thereof) related to one or more patients in the list of patients under the responsibility of the physician. Thus, the preliminary processing operation performed at step 504 can be limited to pre-fetching additional information specifically related to terminal 14+, such as information relating to the patients that may find themselves near terminal 14+.

Generally speaking, at this stage, the information in the holding location 74 pertains to two terminals that are related to one another by a common clinician 20* and a common session 550. One of these terminals is the one with which clinician 20* had an ongoing session before approaching the other. Thus, one of these terminals can have the status of a "session transferor" and the other can have the status of a "session transferee". In this example, terminal 14* is the session transferor and terminal 14+ is the session transferee. Moreover, each of the terminals is associated with a session page delivery indicator that indicates which "pages" of the session 550 are currently being supported by that terminal. At this stage in the live session transfer process, the session transferor supports the entirety of the session 550 and the session transferee does not yet support any of the session 550.

In order to help keep track of which terminal is the session transferor and which terminal is the session transferee for a variety of sessions, the controller 18 may store a table 85 that is accessible to the conduct session process 84. The table 85, which can be stored in the controller 18 or elsewhere, may resemble the following (for the as yet untransferred session 550). Note that terminal 14+ does not yet have the knowledge that it is about to have certain pages of the session 550 transferred to it:

| Terminal | Session | Status | Pages |
|---|---|---|---|
| 14* | 550 | Transferor | All |
| 14+ | N/A | N/A | None |

Next, the conduct session process 84 proceeds to establish the intent of clinician 20* to transfer at least a portion (e.g., certain pages) of the session 550 from terminal 14* (the session transferor) to terminal 14+ (the session transferee). Thus, at step 506, the conduct session process 84 waits for input from clinician 20* in response to the greeting message. At this point, two basic outcomes are possible. In the first outcome, clinician 20* ignores the greeting message. Accordingly, the conduct session process 84 will detect an absence of a response for a predetermined amount of time and will conclude that there is no intent by clinician 20* to transfer any pages of the session 550 to terminal 14+. This leads to execution of step 508, whereby a command is sent to the display formatting function 52, causing the greeting message disappear from terminal 14+. However, no command is issued to cause deletion of the pre-fetched information in the holding location 74, since the session 550 is still ongoing between clinician 20* and terminal 14*. Thus, operation of terminal 14* (the session transferor) remains unaffected.

In the other possible outcome, clinician 20* responds to the greeting message in a timely manner to signal an intent to transfer at least a portion (e.g., some pages) of the session 550 to terminal 14+ or to resume a given session at a given point or page. This can occur in the various ways previously described, such as a pressing a key or touching the screen of terminal 14+.

In addition, the response provided by clinician 20* may indicate the pages of the session 550 that are to be transferred (e.g., the entire session, only visualization of images, etc.) to the session transferee. Alternatively, the portion of the session 350 to be transferred to terminal 14+ may be established by the application context. For example, if clinician 20* has requested an X-ray image on his/her PDA (terminal 14*) and the application has noted the unsuitability of the PDA display and has directed clinician 20* to a terminal that does have a suitable display, then the application can remain in control of displaying the X-ray image on the high quality terminal (terminal 14+), once clinician 20* is authenticated as being at that terminal.

Another way in which clinician 20* can signal an intent to transfer at least a portion of the session 550 to terminal 14+ is by bringing terminal 14* closer to terminal 14+ than what initially caused the conduct session process 84 to deem that terminal 14* was "in proximity" to terminal 14+. Generally, this can be referred to causing terminal 14* to satisfy a computed "terminal proximity condition" with respect to terminal 14+. The terminal proximity condition may be defined by a different distance-time relationship than the "proximity condition" defined earlier. Of course, it is within the scope of the present invention to further refine the definition of the terminal proximity condition using additional factors. For instance, such additional factors may include the type of terminal 14* and the type of terminal 14+.

The conduct session process 84 therefore monitors the data available from the TDS 16 to detect whether terminal 14* has indeed satisfied the terminal proximity condition relative to terminal 14+. If this is the case, then the conduct session process 84 concludes that clinician 20* intends to transfer at least a portion of the session 550 to terminal 14+. Whether the session is fully or partly transferred is a design consideration, and may further be made selectable (e.g., by requiring user input via a keyboard or by requiring that terminal 14* be moved so as to satisfy a computed "terminal remoteness condition" and then moved again to satisfy the terminal proximity condition within a predetermined amount of time, such as 5 seconds, etc.).

Yet another way in which clinician 20* can signal an intent to transfer at least a portion of the session 550 to terminal 14+ is by submitting biometric data (e.g., the transmittal of which is triggered by touching a fingerprint reader on a badge) in the absence of a request for authentication.

Whether the session 550 is fully or partly transferred is a design consideration, and may further be made selectable (e.g., by requiring user input via a keyboard or by requiring that biometric data be resubmitted several times in a given sequence). Alternatively, the pages to be transferred may be established by the session application function 50. In either case, the conduct session process 84 learns of a desired portion of the session 550 to be transferred from the session transferor to the session transferee.

Once the intent of clinician 20* to transfer certain desired pages the session from terminal 14* to terminal 14+ has been confirmed, the conduct session process 84 proceeds transfer the desired portion of the session 550 for clinician 20* from terminal 14* to terminal 14+. Specifically, the conduct session process 84 causes a message to be sent to the session management function 53 in the POC server 30, thereby indicating to the session management function 53 which portion of the session 550 is now to be conducted with terminal 14+ and which portion is no longer to be conducted by terminal 14+.

Meanwhile, terminal 14* of course remains the "session transferor" and terminal 14+ remains the "session transferee". However, the session page delivery indicator for these two terminals will change under the control of the session management function 53. This change is reflected in the table 85 stored in the controller 18, which may now resemble the following:

| Terminal | Session | Status | Pages |
| --- | --- | --- | --- |
| 14* | 550 | Transferor | All except pages A...N |
| 14+ | 550 | Transferee | A...N |

Figure 5C:
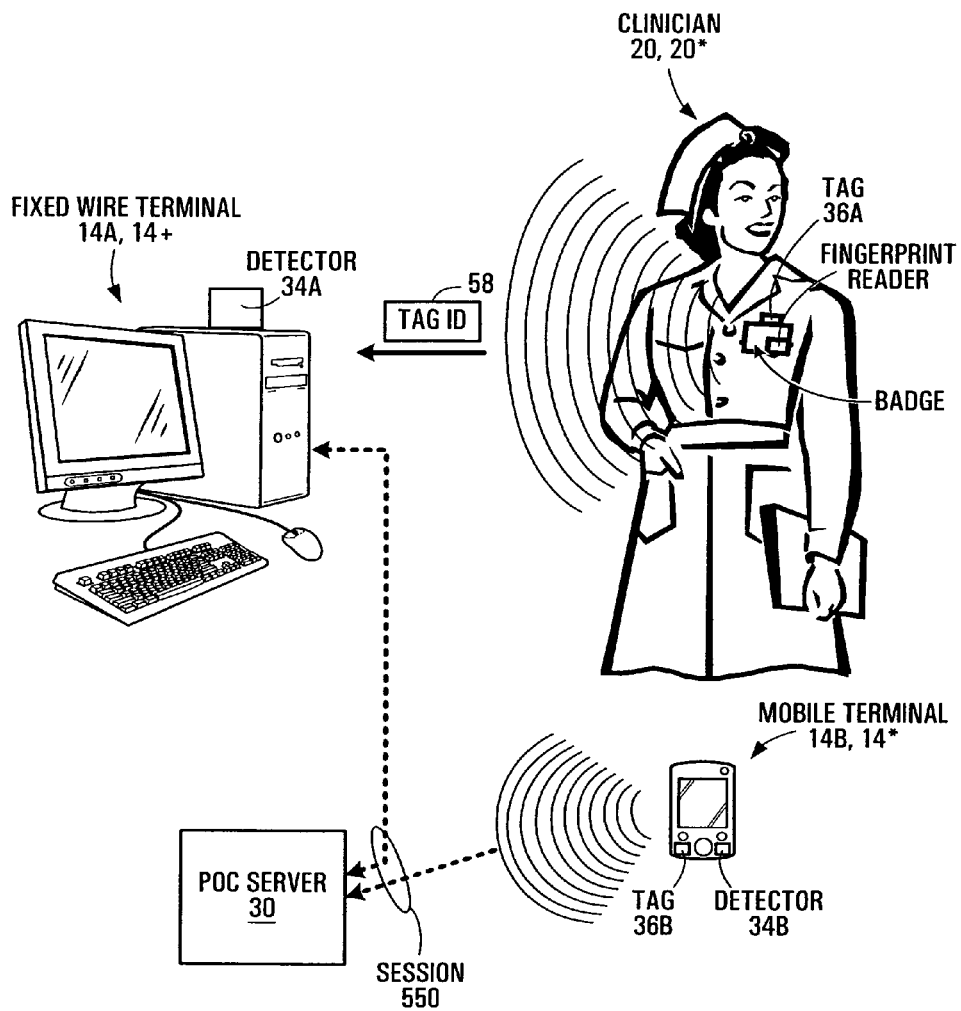
FIG. 5C illustrates the scenario of FIG. 5A upon transfer of at least part of the session to the second terminal, in accordance with one path in the flowchart of FIG. 5B.

Thus, with reference to FIG. 5C, the session 550, which previously existed only between the HIS 12 and terminal 14*, now exists either between the HIS 12 and terminal 14+ alone, or has a first portion that exists between the HIS 12 and terminal 14+ in addition to a remaining portion that exists between the HIS 12 and terminal 14*.

Clinician 20* can then perform a number of tasks during the session 550 while using terminal 14+ (and possibly also terminal 14*). Moreover, clinician 20* may continue conducting the session 550 with terminal 14+ as long as necessary, after which point there are a number of possibilities, each of which is now discussed.

First Possibility (Explicit Transfer of Session)

Figure 5D:
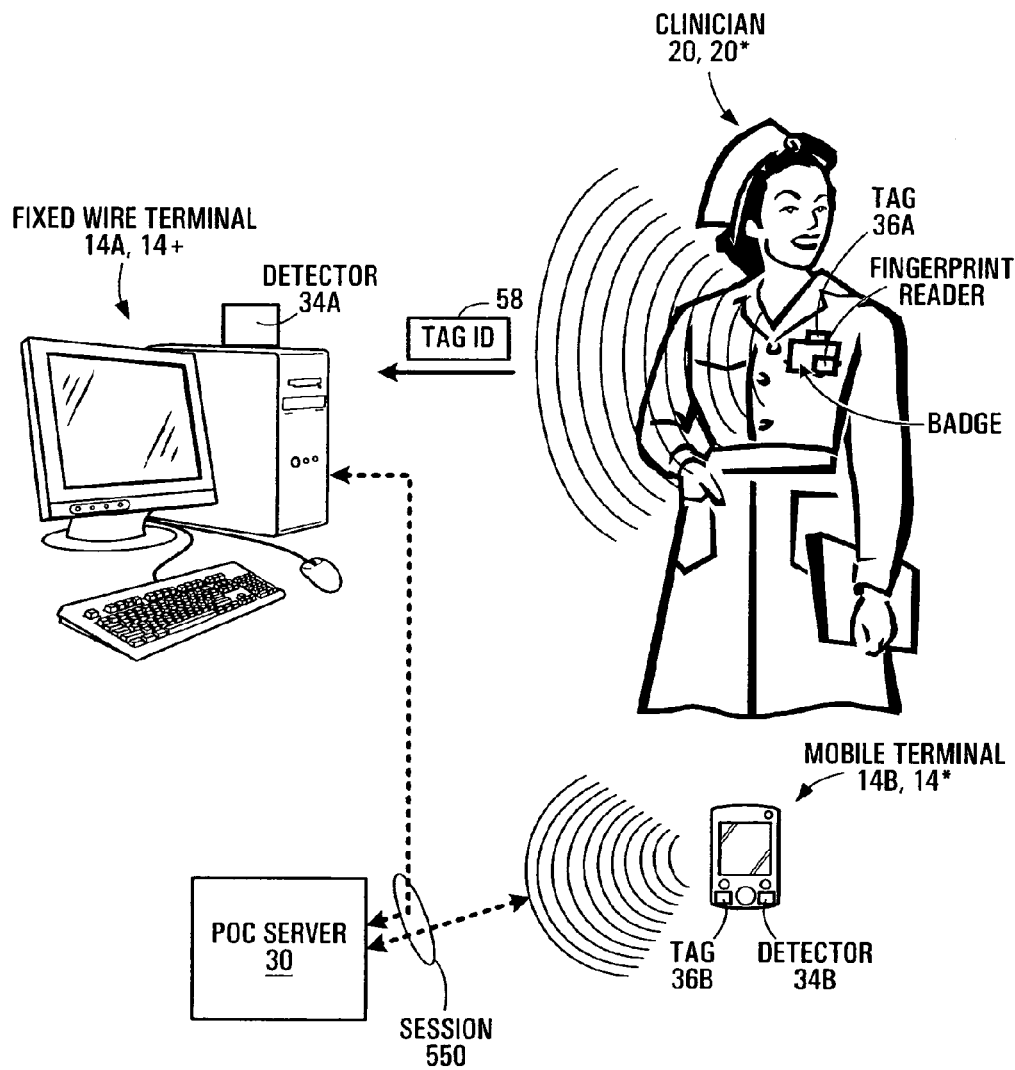
FIGS. 5D through 5G illustrate the scenario of FIG. 5C after a re-transfer of part of the session back to the first terminal, in accordance with various embodiments of the present invention.

Under a first possibility, with reference to FIG. 5D, clinician 20* explicitly signals an intent to transfer the session 550 back to terminal 14*. For example, clinician 20* may click on an appropriate "transfer back" icon on the display of terminal 14+ (or terminal 14*). Alternatively, clinician 20* will cause terminal 14* to re-satisfy the "terminal proximity condition" (with respect to terminal 14+). In either case, an intent to transfer the session 550 back to the session transferor, i.e., terminal 14*, has been signaled by clinician 20*.

Clinician 20*'s intent to transfer the session 550 is detected by the conduct session process 84, which causes a message to be sent to the session management function 53 in the POC server 30, indicating to the session management function 53 that the session 550 is no longer to be conducted with terminal 14+. In response, the session management function 53 sends a command to the display formatting function 52, causing a change in the display of terminal 14+ (e.g., blank screen). However, the session management function 53 does not delete session-related information, since the session 550 continues to be conducted with terminal 14*.

In addition, the session page delivery indicator for terminal 14* and terminal 14+ will change under the control of the session management function 53. This change is reflected in the table 85 stored in the controller 18, which may now resemble the following:

| Terminal | Session | Status | Pages |
| --- | --- | --- | --- |
| 14* | 550 | Transferor | All |
| 14+ | 550 | Transferee | None |

As long as clinician 20* and terminal 14* remain in proximity to terminal 14+, the session 550 can continue to be transferred back and forth between the two terminals as described above. If the session 550 is explicitly transferred back to terminal 14*, and clinician 20* then moves away from terminal 14+, this is detected by the conduct session process 84. The conduct session process 84 then informs the session management function 53, which modifies the above to indicate that terminal 14+ has lost its status as "session transferee" for the session 550. At this point, terminal 14+ will be treated like any other terminal in the communications network 10.

Second Possibility (Mobility Scenario I)

Figure 5E:
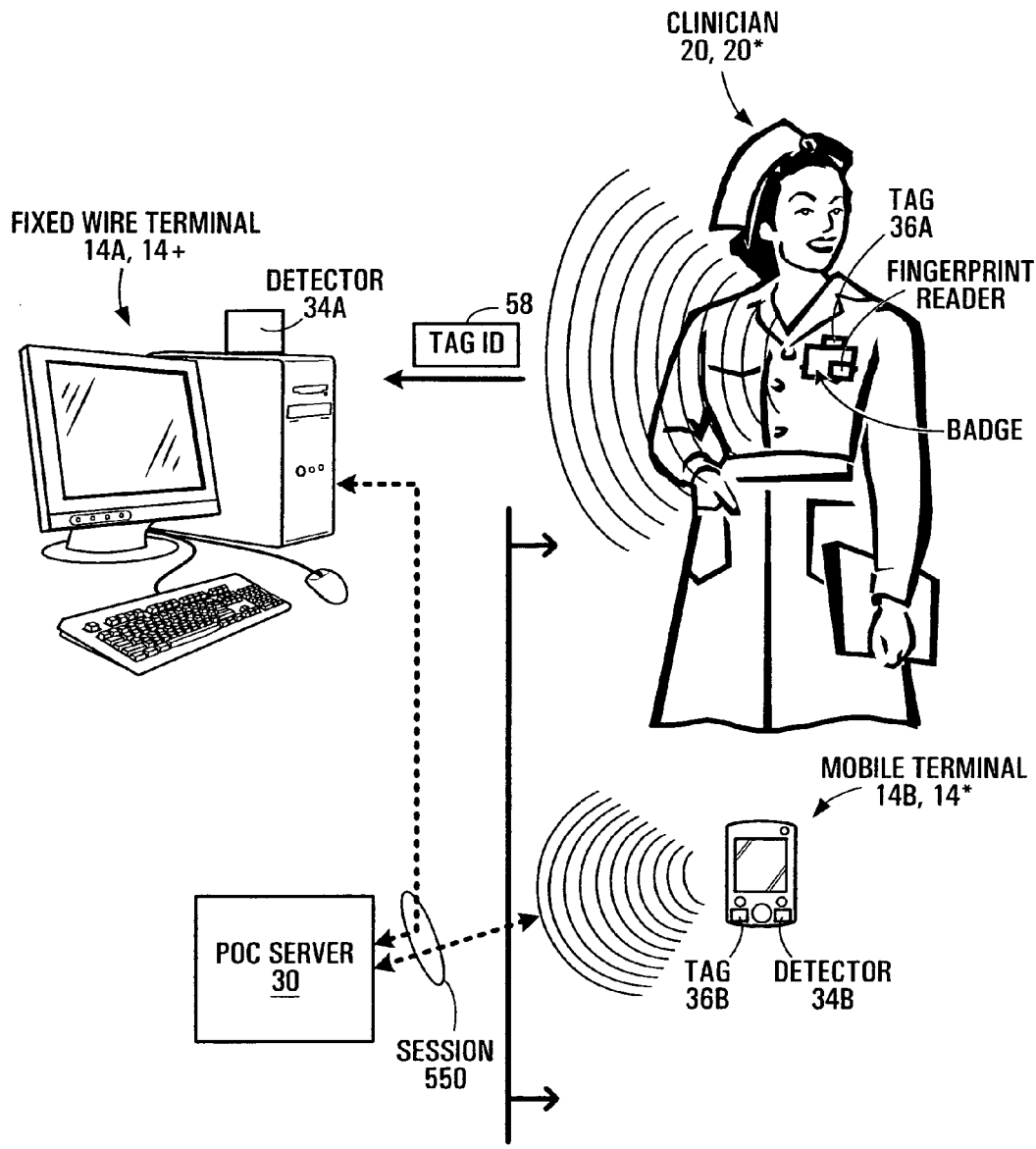

Under a second possibility, with reference to FIG. 5E, clinician 20* takes terminal 14* and moves away from terminal 14+ without having explicitly transferred the session 550 back to terminal 14* before his or her departure from terminal 14+. In other words, clinician 20* remains in proximity to terminal 14* but not in proximity to terminal 14+. This is detected by the conduct session process 84 as satisfaction of a computed "terminal remoteness condition". The conduct session process 84 then takes the necessary actions to autonomously effect a transfer the session 550 back to terminal 14*. This can be referred to, from the session 550's point of view, as "snapping back" to the session transferor (i.e., terminal 14*).

Specifically, the conduct session process 84 causes a message to be sent to the session management function 53 in the POC server 30, indicating to the session management function 53 that the session 550 is no longer to be conducted with terminal 14+. In response, the session management function 53 sends a command to the display formatting function 52, causing a change in the display of terminal 14+ (e.g., blank screen). This eliminates the risk of displaying sensitive data on the display of terminal 14+. However, the session management function 53 does not delete session-related information from the holding location 74, since the session 550 continues to be conducted with terminal 14*.

In addition, the session management function 53 modifies the aforementioned table 85 to indicate that terminal 14+ has lost its status as "session transferee" for the session 550, and also modifies the table 85 to indicate that the full session is supported by terminal 14*. From this point, terminal 14+ is treated like any other terminal in the communications network 10.

Third Possibility (Mobility Scenario II)

Figure 5F:
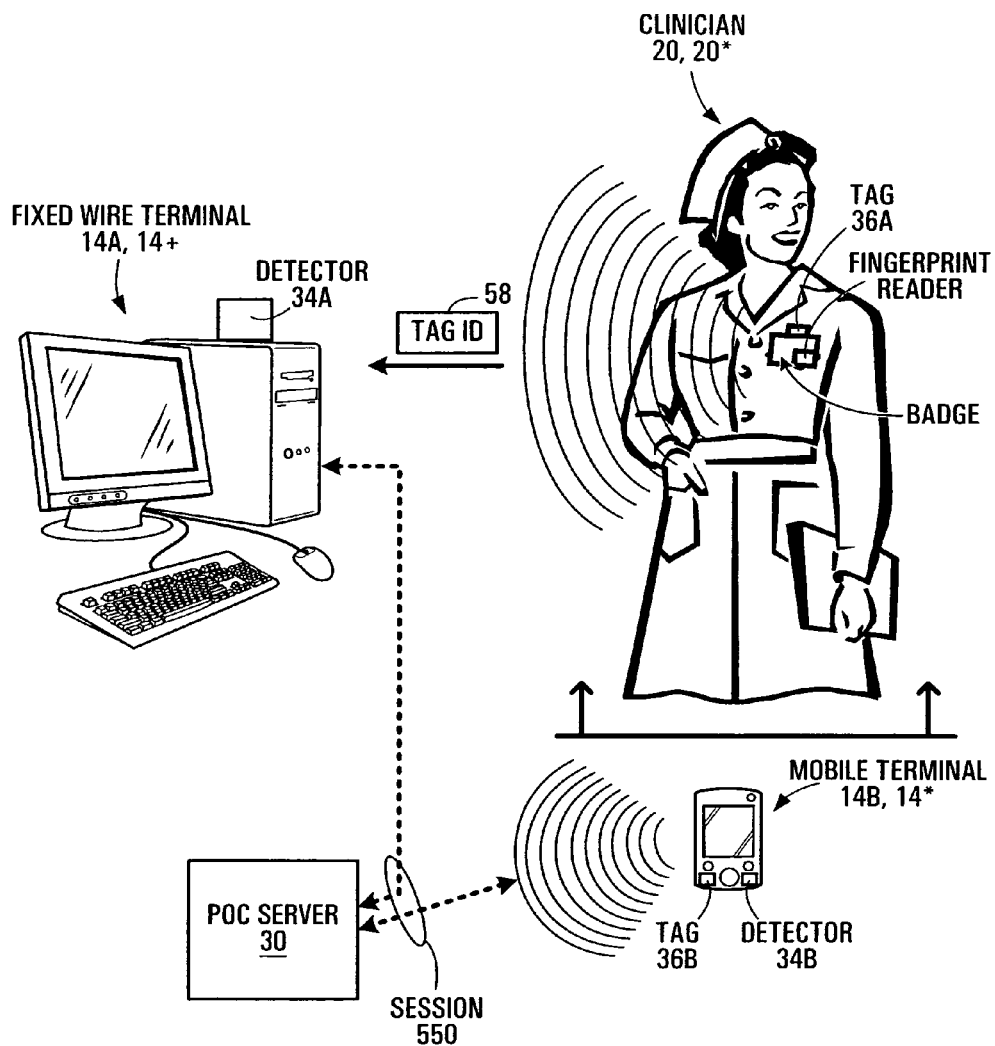

The third possibility is similar to the second possibility, in that clinician 20* moves away from terminal 14+ without having explicitly transferred the session 550 back to terminal 14* before his or her departure from terminal 14+. However, in this case and with reference to FIG. 5F, clinician 20* is unaccompanied by terminal 14*. In other words, clinician 20* remains is no longer in proximity to either terminal 14* or terminal 14+. This is detected by the conduct session process 84, which then takes the necessary actions to transfer the session 550 back to the session transferor, but to immediately follow by suspending the session 550.

Specifically, the conduct session process 84 causes a message to be sent to the session management function 53 in the POC server 30, indicating to the session management function 53 that the session 550 is no longer to be conducted with terminal 14+. In response, the session management function 53 sends a command to the display formatting function 52, causing a change in the display of terminal 14+ (e.g., blank screen). This eliminates the risk of displaying sensitive data on the display of terminal 14+. Accordingly, the session management function 53 modifies the aforementioned table 85 to indicate that terminal 14+ has lost its status as "session transferee" for the session 550, and also modifies the table 85 to indicate that the full session is supported by terminal 14\*. From this point, terminal 14+ is treated like any other terminal in the communications network 10.

In addition, the conduct session process 84 suspends the session 550 by autonomously executing the session suspend process for terminal 14\* (see E- above), since clinician 20\* is deemed to have moved away from terminal 14\*.

Fourth Possibility (Mobility Scenario III)

Figure 5G:
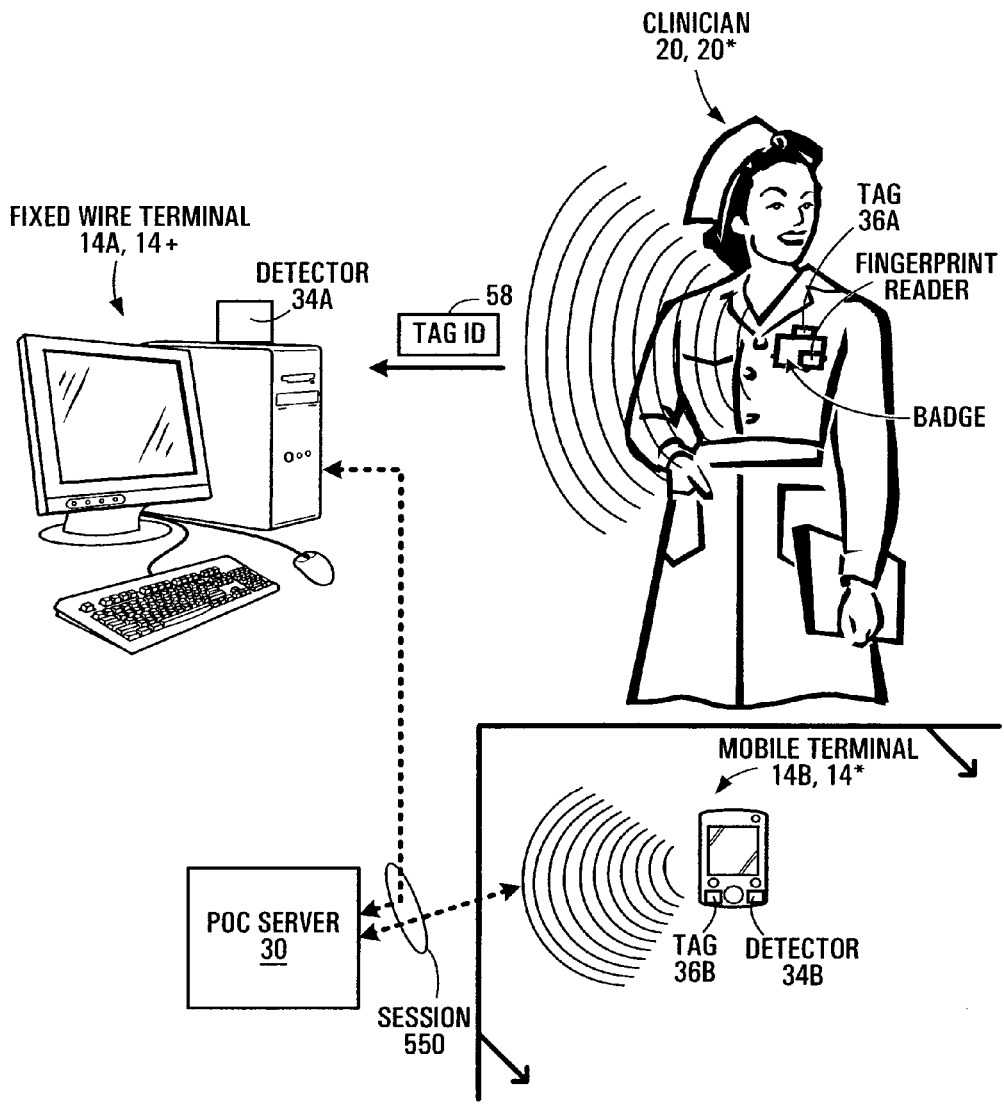

Under a second possibility, with reference to FIG. 5G, terminal 14\* (which is the session transferor for the session 550) leaves the vicinity of both clinician 20\* and terminal 14+. Such a scenario may arise if clinician 20\*'s PDA is lent to a co-worker or is carried away while clinician 20\* is viewing a large-screen display on terminal 14+ (the session transferee).

It is noted that this scenario actually amounts to the equivalent of clinician 20\* moving away from terminal 14\* and satisfying a remoteness condition, which is covered by E- above. Specifically, in accordance with E- above, the conduct session process 84 would send a message to the session management function 53, causing the latter to execute the session suspend process for terminal 14\*. Additionally, in view of F- above, because clinician 20\* is still in proximity to terminal 14+, clinician 20\* would then immediately be asked if he or she wishes to resume the now suspended session at terminal 14+(see F- above).

Now, although the above actions have the desirable effect of preventing a security breach from arising, there may be a disruption to the activities taking place at terminal 14+. To avoid such a disruption, an additional layer of complexity may be added to E- and F- above. Specifically, instead of suspending the session 550 and then asking clinician 20\* if he or she wishes to resume the session 550, the session 550 can simply be transferred to terminal 14+, provided that terminal 14+ is the session transferee for the session 550 (which, in this case, it is).

2. Second System Architecture

In the first system architecture, advantageous use was made of the knowledge that individual clinicians and mobile terminals were in proximity to individual fixed-wire of mobile terminals. This enabled various functions related to establishment and management of sessions with the HIS 12. The second system architecture enables these same functions, in addition to a variety of other functions that make advantageous use of the position (or location) of individually "tagged" clinicians and equipment (e.g., terminals or medical devices) within an overall "location-awareness area" in the hospital. These include:

communication with clinicians based depending on their deemed availability;
assembling a team of clinicians in response to a medical emergency occurring at a given location in the hospital;
tracking of equipment associated with individual clinicians to detect suspicious movement of such equipment;
preventative control of communications devices when found to be in proximity of sensitive medical devices.

The second system architecture differs from the first one in that:

an array of detectors is established across the entire location-awareness area, which may be the overall campus or a significant portion thereof; and
the absolute location of tagged clinicians and equipment (e.g., terminals and medical devices) is detected, calculated and tracked.

From the location and tracking of absolute coordinates of tags, relative to the building spatial grid, the distance between two tag-bearing people or pieces of equipment can be calculated and from a history of these distance calculations, it can be determined whether a given proximity or remoteness constraint is satisfied.

Figure 6A:
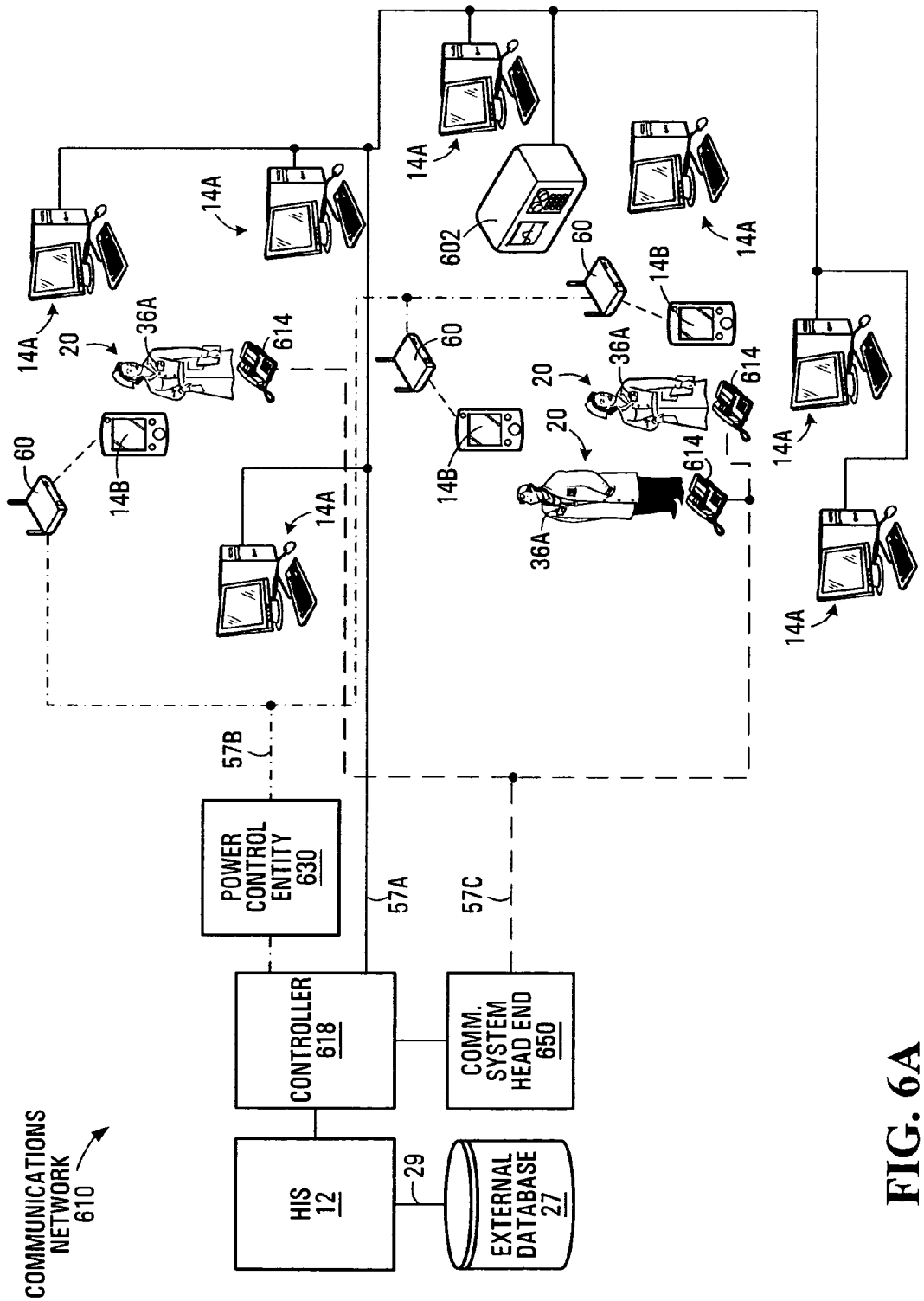
FIGS. 6A and 6B are conceptual block diagram views of a communications network, including a plurality of terminals, a hospital information system (HIS) and a controller.
Figure 6B:
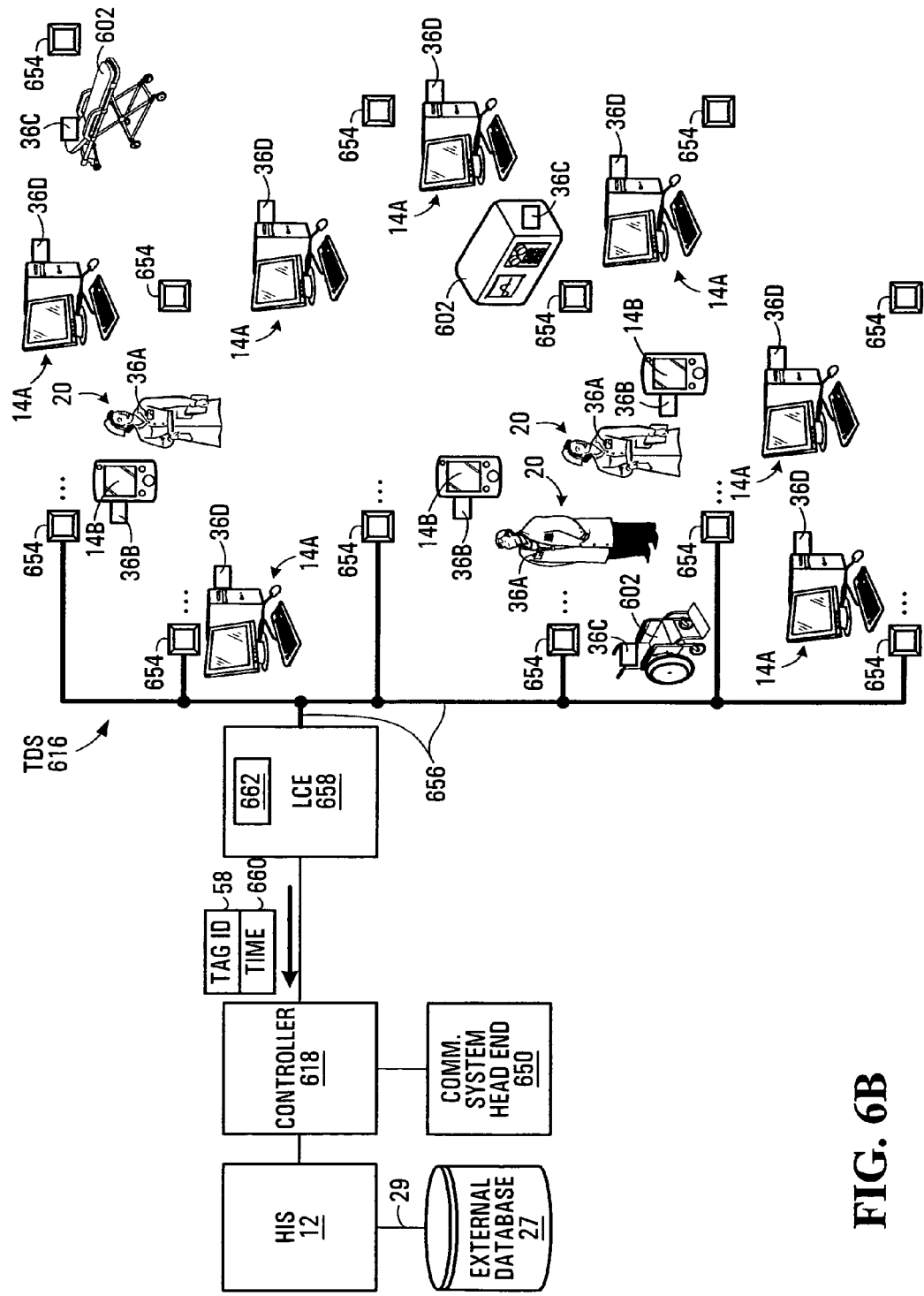

Accordingly, FIGS. 6A and 6B (which should be considered overlaid onto one another) show a conceptual view of a communications network 610 of a healthcare establishment, in accordance with a second example of implementation of the present invention. Again, for ease of reading, the healthcare establishment will hereinafter be referred to as a hospital, but it should be understood that the healthcare establishment may be of any size and may generally consist of a single building or a campus including one or more buildings or pavilions and possibly one or more adjacent areas such as roads and parking lots.

A plurality of fixed terminals 14A and a plurality of mobile terminals 14B serve as entry points to the communications network 610. The terminals 14A, 14B are accessed by a plurality of clinicians 20 who are mobile within the hospital. The term "clinician" is used to denote any individual who may require access to the communications network 10 in the execution of their duties pertaining to diagnosis and/or treatment of one or more patient. While not intended to be an exhaustive list, typically clinicians 20 can include physicians, radiologists, pharmacists, interns, nurses, laboratory technicians and orderlies. In either case, when interpreting the present invention, the word "clinician" should not be construed as limiting the invention to applicability in an environment where individuals are required to have specific medical qualifications.

The communications network 610 also includes a tag/detector subsystem (TDS) 616 connected to a controller 618, which is connected to a healthcare information system (HIS) 12 and a communications system head end 650. In a non-limiting example of implementation, shown in and previously described with reference to FIG. 1C, the HIS 12 includes a clinician database 22, a patient database 24, a departmental database 26, an equipment database 35, as well as an authentication entity 28 and a point-of-care (POC) server 30. In addition, the HIS 12 may permit access to a trusted external database 27, for instance a national electronic health record (EHR) database, via a secure link 29.

Some of the aforementioned components of the communications network 10 will now be described in greater detail. However, a description of the clinician database 22, the patient database 24, the departmental database 26, the equipment database 35, the authentication entity 28 and the point-of-care (POC) server 30 is omitted, since these components have already been described with reference to FIG. 1C, and any variations or modifications required to support the second system architecture will be readily understood and easily implemented by a person of ordinary skill in the art.

Terminals 14A, 14B

The terminals 14A, 14B allow communication between the clinicians 20 and the HIS 12 via the controller 618. Terminals 14A are fixed-wire terminals, such as stationary terminals or workstations, connected to the controller 618 via communication links 57A. Terminals 14B are mobile terminals, such as handheld units (e.g., personal digital assistant (PDA)) or laptop computers, which communicate with the controller 18 via communication links 57B that include wireless portions. The wireless portions of the communication links 57B are secure links that may be encapsulated within the communications network 610, as would be the case for a wireless local area network (WLAN) using WLAN access points 60. In another embodiment, the wireless portions of the communication links 57B may involve an external network connection, as would be the case when the mobile terminals 14B are cellular phones or cellular data devices.

Each of the terminals 14A, 14B has a display capability, which may be different for different types of terminals. For example, mobile terminals 14B may have inferior display capabilities, while certain ones of the fixed-wire terminals 14A may have superior display capabilities.

Medical Devices 602

A plurality of medical devices 602 is also collectively shown in FIGS. 6A and 6B. A medical device refers to a piece of healthcare equipment used for a particular purpose in the hospital. Examples of medical devices 602 include but are not limited to surgical instruments, wheelchairs, emergency resuscitation carts (colloquially referred to as "crash carts"), life-support units, computerized axial tomography (CAT) or magnetic resonance imaging (MRI) scanners, and any other conceivable piece of equipment, either mobile or stationary, normally found in a healthcare environment.

It will be noted that a first subset of the medical devices 602 is connected to the communications network 610, and these are shown in FIG. 6A. Non-limiting examples of medical devices that may be members of the first subset include devices that are used to input data into the HIS 12 or extract data from the HIS 12, for example CAT scanners and MRI scanners. Stationary medical devices in the first subset may be connected to the communications network 610 via the communication links 57A, while mobile medical devices in the first subset may be connected to the communications network 610 by communication links 57B.

Aspects of operation of the medical devices 602 in the first subset (i.e., connected to the communications network 610) can be controlled by the controller 618. One example of operation that can be controlled would be authorization/authentication to use a particular medical device, this being limited to only those operatives trained in so-doing. This would be achieved by only allowing the medical device to be functional while a qualified, authorized, authenticated operator is found to be in its vicinity. Another example of an aspect of operation is an on/off state of the medical device 602.

A second subset of the medical devices 602 is not connected to the communications network 610 because there is no need to exchange data between these devices and the HIS 12. Such medical devices may be referred to as "passive" from the communications standpoint and, although not illustrated in FIG. 6A, they are represented in FIG. 6B. By way of non-limiting example, wheelchairs and stretchers may be members of the second subset of the medical devices 602. However, it is envisaged that certain other conventionally "passive" devices may be equipped with communication functionality and therefore whether a particular medical device belongs to the first subset or the second subset might depend on factors other than simply the nature of particular medical device.

Communications System Head End 650

Although clinicians 20 may communicate with one another using mobile terminals 14B, the communications network 610 may further provide the ability to use a more conventional communications system. To this end, the communications system head end 650 enables telephony-style or other communication between individuals in the hospital or external to the hospital, including the clinicians 20. In one embodiment, the communication system head end 650 may comprise a switch and processing equipment, and may be connected to an intercom system and speakers distributed throughout the hospital for communicating with individuals or group of individuals in the hospital. Optionally, the communication system head end 650 may be connected to a plurality of communication devices 614 via a plurality of paths 57C (fixed or partly wireless). Non-limiting examples of the communication devices 614 include pagers and WLAN phones. The communication devices 614 are typically carried by the clinicians 20, allowing telephony-style communications to be established with specific individuals in the hospital. The communications system head end 650 could also comprise a PBX connected to fixed and wireless telephones, with the location of the fixed telephones being known a priori.

Tag/Detector Subsystem (TDS) 616

With specific reference now to FIG. 6B, the TDS 616 includes a plurality of tags 36A, 36B, 36C, 36D, a plurality of contact-less tag detectors 654 and a location calculation engine (LCE) 658, which may be integrated with the controller 618 or separate therefrom. The tags 36A, 36B, 36C and 36D are associated with the various people and equipment whose location needs to be ascertained. In this case, as before, tags 36A are respectively associated with the clinicians 20 and tags 36B are respectively associated with the mobile terminals 14B. In addition, tags 36C are respectively associated with the medical devices 602 in both the first and second subsets, while tags 36D are respectively associated with the fixed-wire terminals 14A.

Similarly to what was described with reference to the first system architecture, a given tag 36A, 36B, 36C, 36D operates in such a way as to provide a brief radio frequency signal that encodes an identifier of the given tag 36A, 36B, 36C, 36D, hereinafter referred to as a "tag ID" 58. Without being interpreted as a limitation of the present invention, the tags 36A, 36B, 36C, 36D can be active (i.e. the tag frequently or periodically emits a signal), semi-active (i.e. the tag emits a signal only in response to receiving another signal), or passive (i.e. the tag only reflects a received signal). The decision to select active, semi-active or passive tags depends on various factors such as the required range, precision, and power consumption/battery lifetime/weight considerations.

In the selection of a suitable tag technology, care should also be taken to ensure that the tags, which are themselves transmitters of RF energy, do not interfere with sensitive medical equipment, e.g., certain ones of the medical devices 602. In a non-limiting example, the use of a low-power multi-GHz center-frequency Ultra Wideband (UWB) solution, which operates with RF bursts of 1 nanosecond duration at a peak power of 15--30 mW (giving an average power of nanowatts or picowatts), meets this requirement.

It is noted that the information contained in the tag IDs 58 is unique for the various tags 36A, 36B, 36C, 36D. Assuming that there is a one-to-one physical association between the clinicians 20 and the tags 36A, then the tag ID 58 for the tag 36A attached to a given clinician 20 can contain the clinician identifier 38 of the given clinician 20. (Alternatively, if the clinician identifier 38 needs to be kept confidential, then the tag ID 58 can contain the clinician-specific tag ID 42 for the given clinician 20.) Similarly, if there is a one-to-one physical association between the mobile terminals 14B, medical devices 602 and fixed-wire terminals 14A on the one hand, and the tags 36B, 36C and 36D on the other, then the tag ID 58 for the tag attached to a given one of these pieces of equipment can contain a serial number or MAC address of the given piece of equipment.

The detectors 654 are distributed throughout the hospital rather than being collocated with the fixed-wire terminals 14A. The detectors 654 are positioned at known locations and may take the form of a grid or an array. Specifically, the locations of the detectors 654 may be kept in a database 662 in the location calculation engine (LCE) 658. In addition, the detectors 654 may span multiple floors of a common building, thus effectively being distributed in three dimensions. Also, the detectors 654 may be vertically separated on a given floor, thereby giving an improved capability for z-axis spatial resolution within that floor.

Depending on the type of tag used, each of the detectors 654 may include either a receiver for receiving radio frequency signals emitted by active tags, or both a transmitter for emitting radio frequency pulses and a receiver for receiving radio frequency signals emitted (or reflected) by semi-active (or passive) tags in response to the emitted radio frequency pulses.

Each of the detectors 654 detects tags in a surrounding three-dimensional volume which is a "coverage zone" for that detector 654. The union of the coverage zones for all of the detectors 654 defines a location-awareness area of the hospital. If a given tag is located within the location-awareness area of the hospital, then the tag ID 58 that the given tag emits (or reflects) will be detectable by at least one of the detectors 654. The fact that the location of the detectors 654 is known is sufficient to give an approximate idea as to where a detected tag is located within the location-awareness area of the hospital; however, it is insufficient to provide a precise estimate of the location of that tag. Thus, the second system architecture utilizes the LCE 658 to provide the precision required in estimating the location of individual tags in the location-awareness area of the hospital.

For example, assume that the desired precision in the relative location between a clinician 20 and a piece of equipment (e.g., terminal 14A, terminal 14B, medical device 602), or between two pieces of equipment, is on of the order of ±10-25 cm. Thus, approximately twice this precision (i.e., ±5-12.5 cm) on the absolute measurements is required, assuming that errors occur randomly. The required precision can be achieved by use of high resolution ultra-wideband radio-frequency transmitting tags, which emit sub-nanosecond bursts of radio frequency. Alternatively, the required precision can be achieved by use of ultrasonic acoustic tags which emit sub-millisecond bursts of acoustic energy, since the propagation length of both a 1 ns electromagnetic burst and a 1 millisecond acoustic burst is of the order of 1 foot, limiting the spatial resolution to around this level, depending upon exactly how the signal is received and measured.

Figure 7:
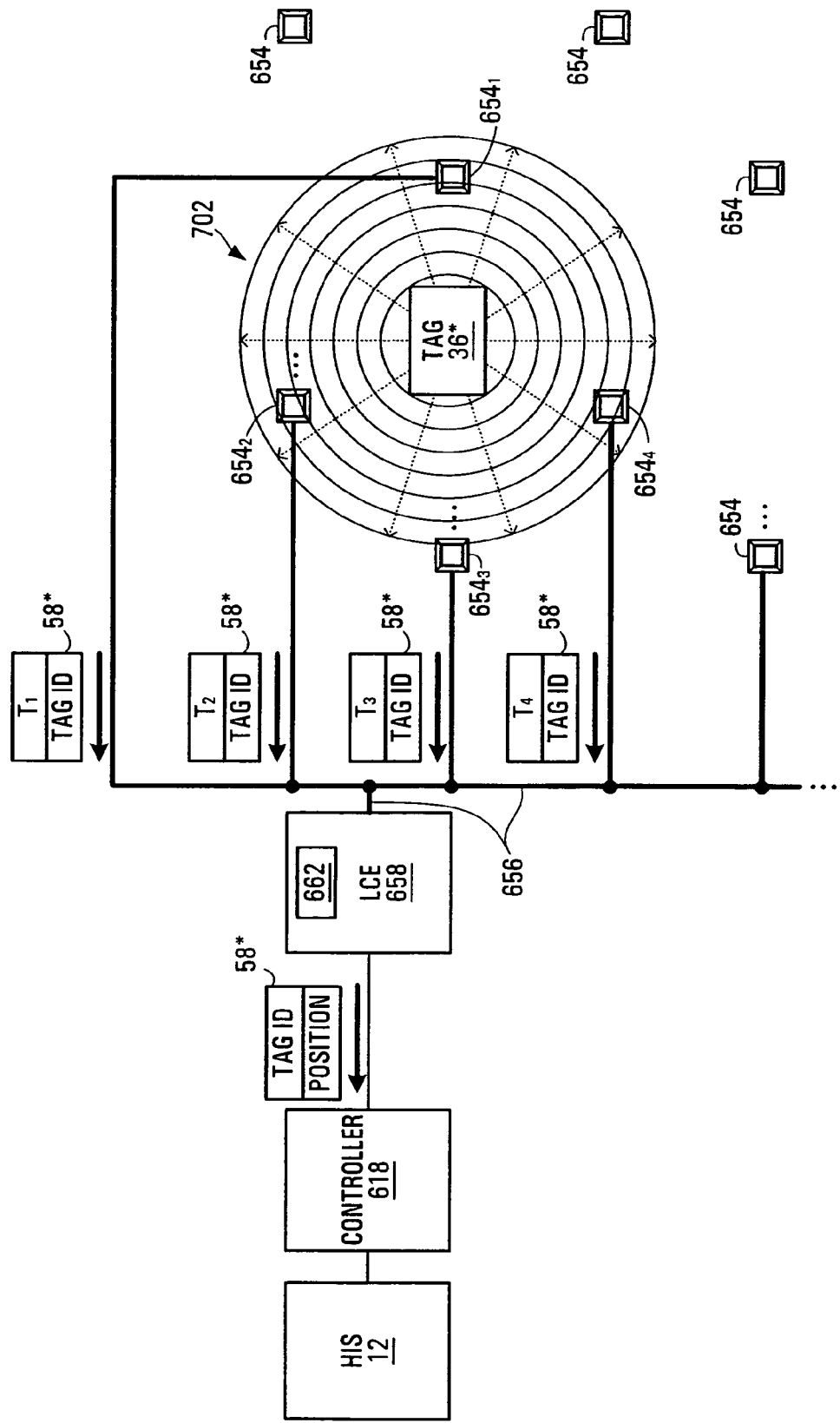
FIG. 7 depicts detection of a burst of radio frequency emitted by a tag in order to determine the location of the tag, in accordance with an embodiment of the present invention.

One possible way to achieve adequate spatial resolution on the basis of time measurements is now described. Specifically, the LCE 658 maintains an absolute system time reference, which it distributes to the detectors 654. With reference to FIG. 7, when a burst 702 corresponding to a particular tag (denoted 36*) having a particular tag ID (denoted 58*) is received at a particular detector (denoted $654_1$), the particular detector $654_1$, measures the absolute system time $T_1$ at which the burst 702 was received. In addition, other detectors (in this case three detectors denoted $654_2$, $654_3$, $654_4$) also receive the same burst 702, possibly at different times. Upon receipt of the burst 702, each of the detectors $654_1$, $654_2$, $654_3$, $654_4$ sends to the LCE 658 the detected tag ID 58* and the absolute system time $T_1$, $T_2$, $T_3$, $T_4$ at which the burst 702 was received.

At the LCE 658, the received times $T_1$, $T_2$, $T_3$, $T_4$ can be compared to calculate the differences in time of flight to each of at least 3 of the detectors $654_1$, $654_2$, $654_3$, $654_4$. These differences can then be used to estimate the position of the tag 36* in two- or three-dimensional space, since the detectors' locations are known a priori from the installation grid and are available by consulting the database 662 in the LCE 658.

In an alternative embodiment, rather than use an absolute system time reference, one can measure received signal direction from multiple detectors. To render such an embodiment capable of achieving the required precision, one should consider enhancements such as the use of a large array of large antennas, a very high (~30-40 GHz) radio frequency combined with smaller directional antennas, a directional and/or time difference-measuring optical pulse, or other technologies, such as acoustic, infrared, ultrasonic, etc.

Of course, the greater the number of detectors used, the greater the number of detectors that will receive a given burst 702 and thus, the more accurate the position estimate will be. For example, while a two-dimensional position estimate of the particular tag 36* requires a minimum of three detectors to detect the tag ID 58*, it may be desirable to use the data from four detectors that receive the tag ID 58*. This will allow for "occlusion" of one detector; alternatively, it allows the use of four sets of three measurements to produce four position estimates, each of which will contain errors. The overall error can be reduced by combining these in various ways including "least squares fit" as well as other methods. In this context, "occlusion" means that no useful signal reaches the detector, and exemplifies an environment where ultra-wideband (UWB) solutions are significantly more robust than optical or acoustic ones.

In addition, a position estimate can be obtained by integrating the results from multiple bursts. This will lead to an increased location precision for static and slow-moving tag-bearing people or pieces of equipment, but a velocity-related lag in computing the location of fast-moving tag bearers. The effects are dependent upon the pulse repetition rate, the number of pulses over which location data is integrated, the velocity of the tag bearer and the required precision in the location measurement.

Similarly, to achieve a three-dimensional position estimate, one theoretically requires only four measurements, but such a measurement is rendered difficult and error-prone due to a small vertical baseline (Z-axis) allowed by floor-ceiling distance triangulation in the vertical axis. Thus, it may be preferable to use multiple measurements and reduce error though processing operations. For example, it may be advantageous to collect the data from six (6) detectors, allowing 30 sets of position estimates to be made without receiver occlusion, or 5 sets of position estimates to be made with one receiver being occluded.

To summarize the above, the detectors $654_1$, $654_2$, $654_3$, $654_4$ receive the burst 702 from the nearby tag 36*, detect the tag ID 58* in the received burst 702 and communicate the tag ID 58* to the LCE 658 along a set of communication links 656. Along with the tag ID 58*, the detectors 654 provide the absolute system time $T_1$, $T_2$, $T_3$, $T_4$ at which the burst 702 was received (or, on the other hand, the direction from which the individual tag ID 58* is detected). Based on this information and on knowledge of the positions of the detectors $654_1$, $654_2$, $654_3$, $654_4$ within the location-awareness area of the hospital, the LCE 658 then determines the estimated position of the tag 36* within the hospital. The tag ID 58* and the estimated position of the corresponding tag 36* (generally: tags 36A, 36B, 36C, 36D) are provided to the controller 618, which will now be described in greater detail.

Controller 618

Figure 8:
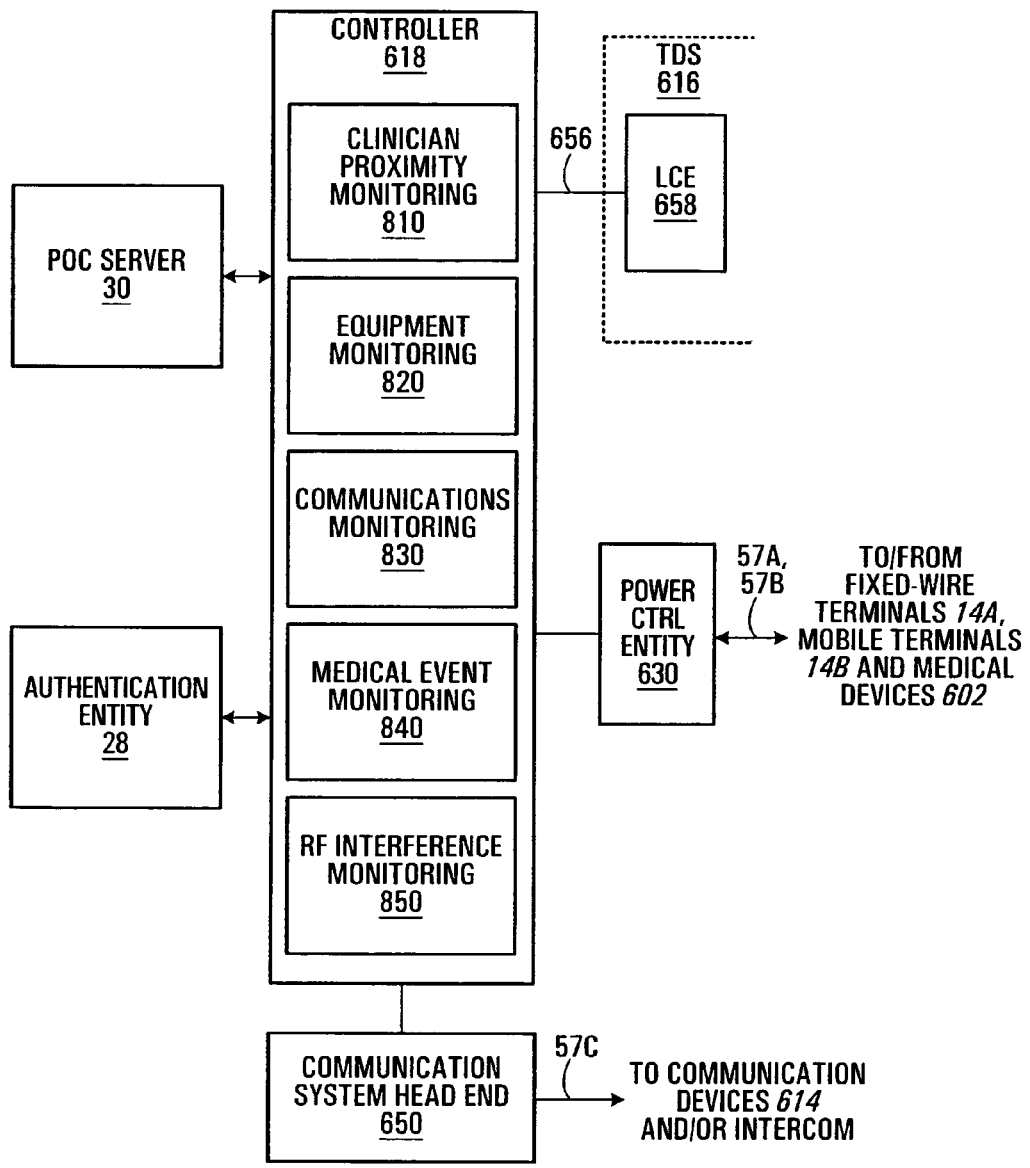
FIG. 8 is a detailed block diagrammatic view of the controller of FIGS. 6A and 6B, in accordance with an embodiment of the present invention.

The controller 618 comprises suitable software, hardware and/or control logic for implementing a variety of "monitoring processes" that operate in the background until they detect that a certain trigger condition is satisfied, whereupon further processing operations are performed. As shown in FIG. 8, these include a clinician proximity monitoring process 810, a tagged equipment monitoring process 820, a communications monitoring process 830, a medical event monitoring process 840 and an RF interference monitoring process 850. The monitoring processes 810-850 may all run in parallel to one another. Each of the aforementioned monitoring processes is now described in greater detail.

I- Clinician Proximity Monitoring Process 810

Similar to the clinician proximity monitoring process 80 described earlier, the clinician proximity monitoring process 810 monitors the output of the TDS 616 to decide when clinicians 20 who do not have sessions are found to be in proximity to individual ones of the terminals 14A, 14B. The definition of "in proximity" may vary in accordance with operational requirements. In one embodiment, a given clinician of interest (denoted 20*) is deemed to be "in proximity" to a given terminal of interest (denoted 14*) when a computed "proximity condition" is satisfied, e.g., when the relative distance between the estimated position of the tag 36A associated with clinician 20* and the estimated position of the detector 34A, 34B associated with terminal 14* remains less than a certain threshold distance, continuously, for at least the duration of a time window.

Of course, it is within the scope of the present invention to further refine the definition of the proximity condition using additional factors. For instance, such additional factors may include the identity or professional role of clinician 20*. Another example of such an additional factor includes an indication of whether terminal 14* is in clinician 20*'s "field of view". In one embodiment, determining whether terminal 14* is within clinician 20*'s field of view may involve processing the intensity of the signal received from the tag associated with clinician 20*. Based upon the estimated position of clinician 20*, relative to the nearby detectors 654 and hence the known free space path length from clinician 20* to those detectors, the expected received powers at the various detectors 654 can be computed. Any differences from those powers, such as a significant power level drop in one or two detectors, can be attributed to absorption of the signal by the body of clinician 20*, which allows the direction in which clinician 20* is facing to be inferred.

In other words, a lower-intensity signal may indicate that clinician 20*'s body is in the way and hence it is possible to infer in which direction clinician 20* is facing and determine whether terminal 14* is in clinician 20*'s field of view. In another embodiment, the controller 618 computes a velocity vector of clinician 20* by tracking the location of clinician 20* over time. By taking into account a certain angle on both sides of the velocity vector, and assuming that clinician 20* is moving in the direction that he or she faces, the controller 618 can obtain a field of view of clinician 20* and determine whether terminal 14* is in that field of view. Furthermore, the computed velocity of clinician 20* may allow for a determination of intent, in that if clinician 20* who intends to use terminal 14* will approach it and slow down (and eventually stop), whereas clinician 20* who does not intend to use terminal 14* will likely remain at a high walking speed.

Thus, it will be appreciated that consideration of clinician 20*'s field of view may be advantageous in order to take into account situations wherein clinician 20*, although "close" to terminal 14*, is oriented in such a way that he or she cannot interact with terminal 14*. (For instance, clinician 20* has his or her back facing terminal 14*.) Thus, the proximity condition may be satisfied not only when clinician 20* is "close" to terminal 14*, but when terminal 14* is within clinician 20*'s "field of view".

Once the clinician proximity monitoring process 810 has deemed clinician 20* to be in proximity to terminal 14* (i.e., the proximity condition is satisfied), the controller 618 executes a "session establishment" process, which is similar to the session establishment process 82 previously described with reference to FIGS. 3B and 3C. This results in the establishment of a session for clinician 20* between terminal 14* and the HIS 12.

Once the session is established, the controller 618 enters a "conduct session" process for the session, which is similar to the conduct session process 84 previously described. During the session, clinician 20* may perform a variety of activities leading to any one of the previously described non-limiting example scenarios A- through D-. In addition, although it is transparent for most of the activities conducted during the session, the conduct session process nevertheless continues to monitor the information from the TDS 616 in order to detect certain conditions of clinician-terminal proximity and terminal-terminal proximity. Specifically, during the session, clinician 20* may perform a variety of activities in addition to the above, which may lead to one of the previously described non-limiting example scenarios E- through G-.

In the specific case of scenario G- and mobility scenario III related thereto, it is recalled that this scenario covered the case where clinician 20* had approached a new terminal, denoted 14+, while a session was ongoing between the HIS 12 and terminal 14*. This was followed by terminal 14* leaving the vicinity of both clinician 20* and terminal 14+. It is recalled that such a scenario may arise if clinician 20*'s PDA is lent to a co-worker or is carried away while clinician 20* is viewing a large-screen display on terminal 14+ (the session transferee). If the PDA is being lent to colleague, then there may not be cause for concern. However, if the PDA has been stolen, then it may be desirable to detect this action so that the appropriate measures can be taken. Specifically, potentially suspicious motion of tagged equipment in this and other scenarios is handled by the tagged equipment monitoring process, as now described.

II- Tagged Equipment Monitoring Process 820

In order to support the tagged equipment monitoring process 820, the equipment database 35 is expanded so as to include additional fields for each piece of tagged equipment (e.g., terminal or medical device), including but not limited to valuable mobile equipment, such as PDAs and tablet PCs. Specifically, with reference to FIG. 11, an enhanced equipment database 1135 includes the same fields as the equipment database 35 in FIG. 1D, in addition to an "authorized users" field 1110 and a "physical boundaries" field 1112.

For a given piece of tagged equipment, the authorized users field 1110 provides a list of clinicians who have the authorization to use the given piece of tagged equipment. The clinicians in this list can be identified by their clinician ID 38 or clinician-specific tag ID 42, for example, or by any other conceivable identifier. The list of clinicians who have the authorization to use a given piece of tagged equipment may change over time and may be under the control of hospital administration.

For a given piece of tagged equipment, the physical boundaries field 1112, which is optional, may indicate specific areas of the hospital where the given piece of tagged equipment is allowed to be present, with everywhere else being considered impermissible. Alternatively, the physical boundaries field 1112 may indicate specific areas of the hospital where the given piece of tagged equipment is not allowed to be present, with everywhere else being considered permissible. The chosen significance of the physical boundaries field 1112 may be different for different pieces of tagged equipment, and may depend on the most efficient representation in memory. By way of non-limiting example, it may be the case that a crash cart in a particular Ward should not be removed from there but may be moved around within the ward; hence, the physical boundaries for this particular piece of tagged equipment could be the particular Ward in question.

Based on the data from the enhanced equipment database 1135 and the data from the TDS 616, the tagged equipment monitoring process 820 determines, for each piece of tagged equipment, the position of the tag associated with the piece of tagged equipment, consults the authorized users field 1110 for the piece of tagged equipment, determines the position of the tags for the clinicians who are authorized to use the piece of tagged equipment, and determines the estimated distance between the tags of the piece of tagged equipment and each of these authorized clinicians. If, for a particular piece of tagged equipment, the estimated distance exceeds a threshold value for all of the authorized clinicians (or is not within the threshold value for at least one of the authorized clinicians), and if the particular piece of tagged equipment is in motion (e.g., based on historical data), the tagged equipment monitoring process 820 will conclude that the particular piece of tagged equipment is being transported by someone or something other than one of the authorized clinicians of the particular piece of tagged equipment. The particular piece of tagged equipment is said to be undergoing suspicious motion, which may be the result of an act of theft. A suitable alarm signal can thus be generated, which may lead to actions such as communicating with building security, activation of cameras, locking of doors, erasure of data, etc.

In addition, having determined, for each piece of tagged equipment, the position of the tag associated with the piece of tagged equipment, the tagged equipment monitoring process 820 consults the physical boundaries field 1112 for the piece of tagged equipment and determines whether the piece of tagged equipment is in an area where it is (or is not) allowed to be, irrespective of whether the piece of tagged equipment is in motion or not. If the piece of tagged equipment in question is in an area where it is not allowed to be (or is outside any and all areas where it is allowed to be) then a suitable alarm signal can be generated as described above.

III- Communications Monitoring Process 830

Figure 9A:
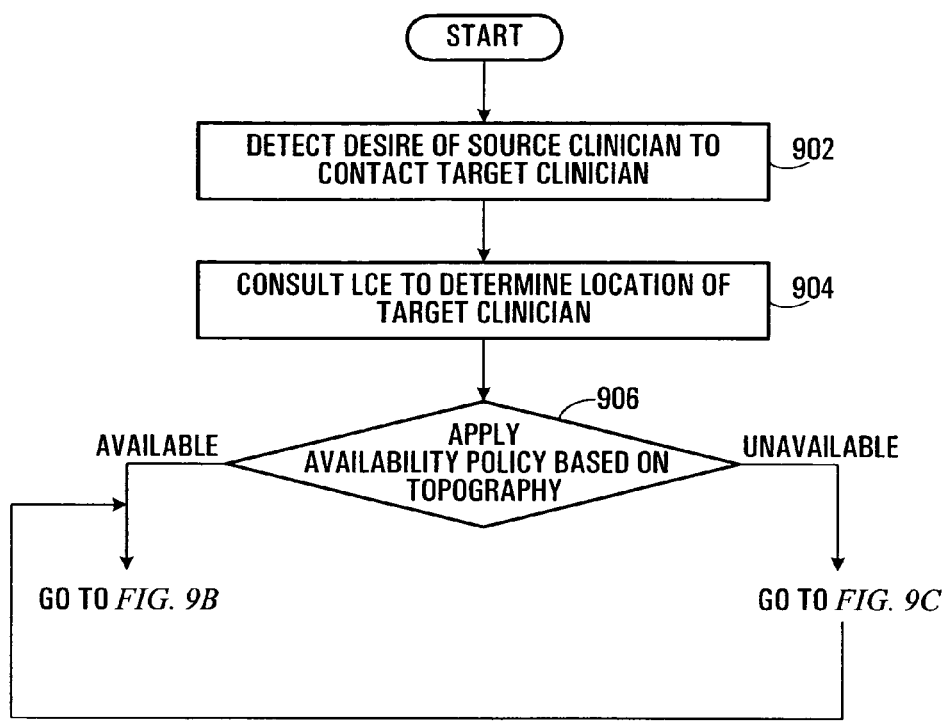
FIGS. 9A to 9C combine to create a flowchart showing steps in a process used to establish communications with a target clinician in the hospital, in accordance with an embodiment of the present invention.
Figure 9B:
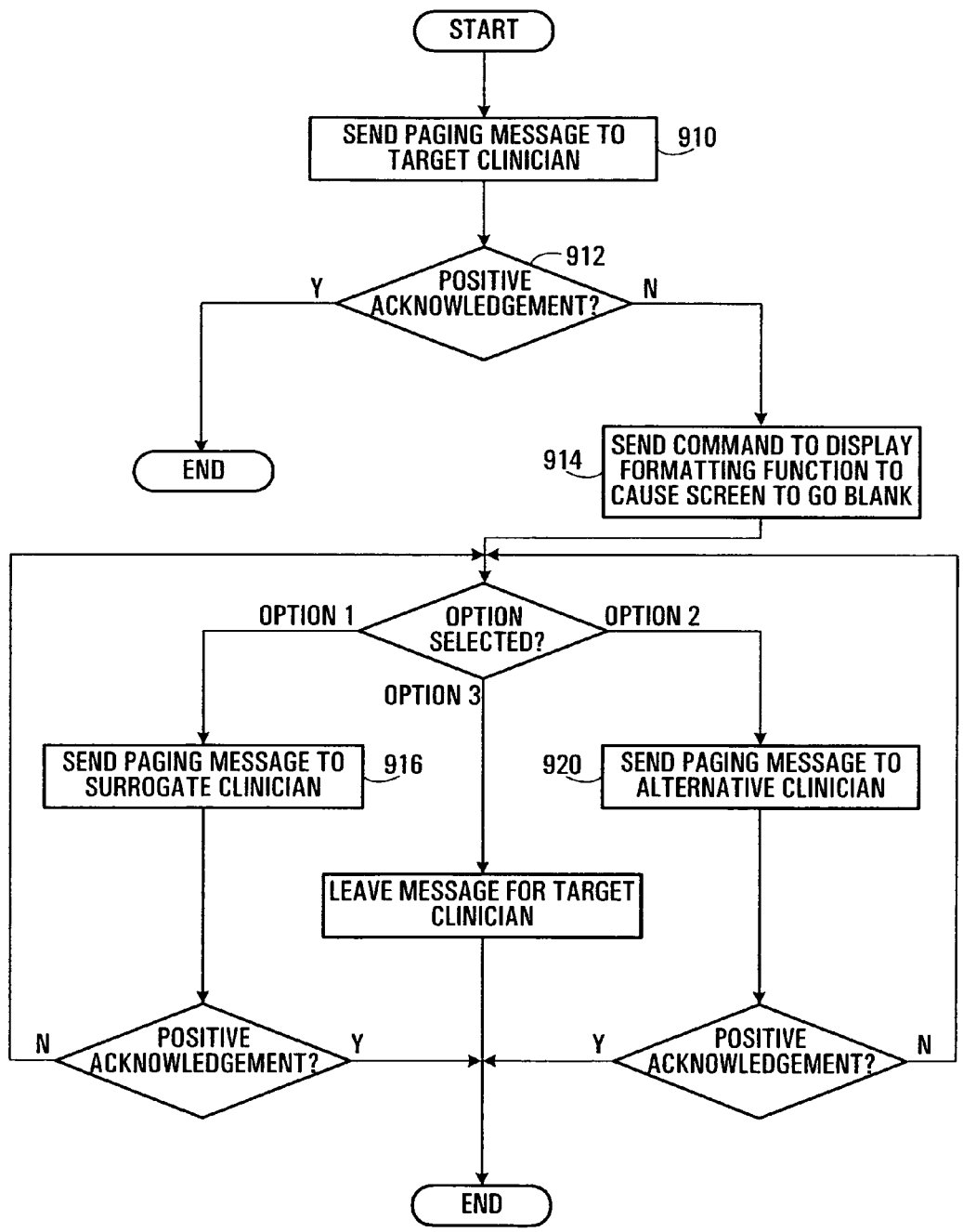
Figure 9C:
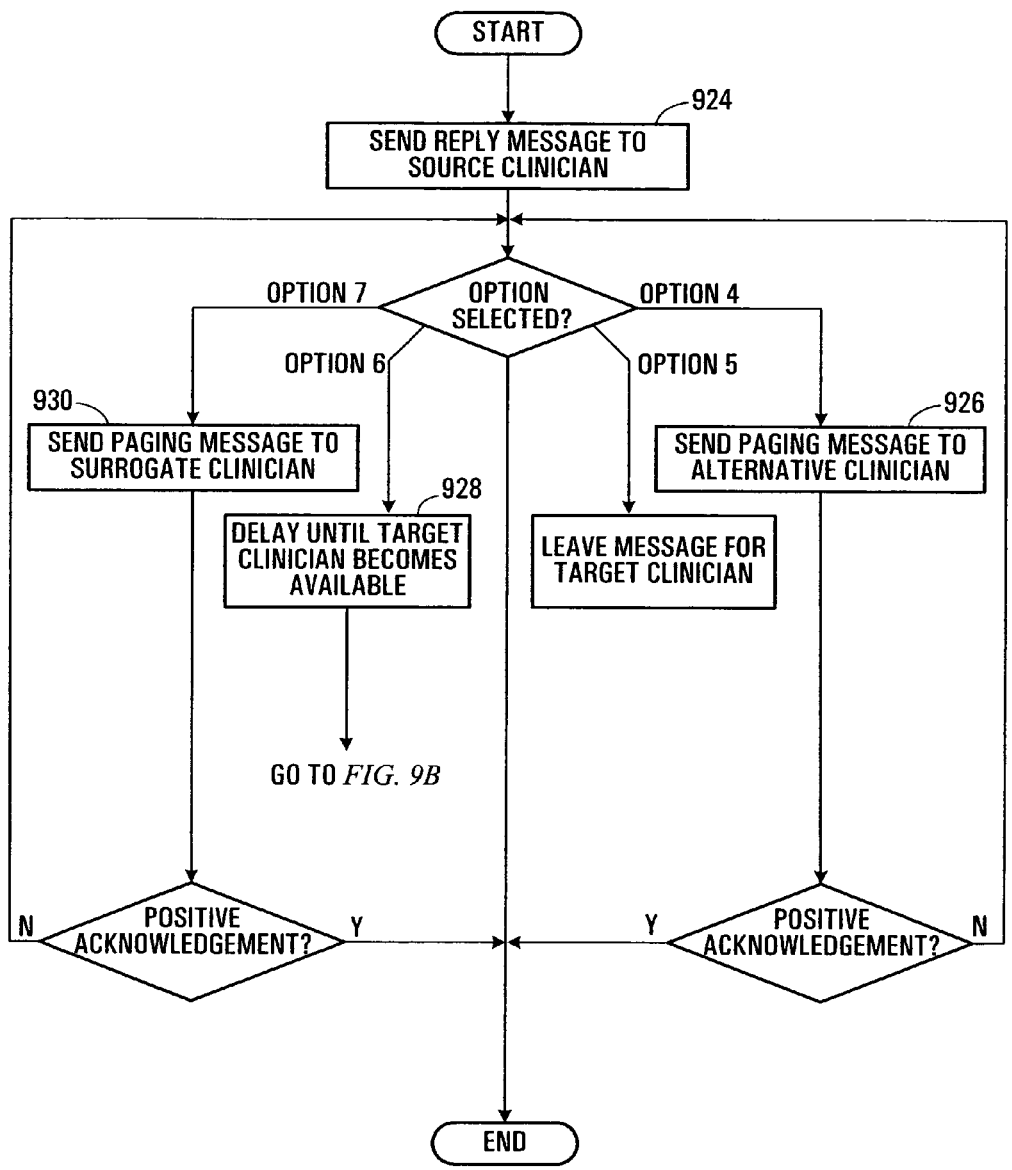

With reference to FIGS. 9A, 9B and 9C, at step 902, the controller 618 detects that a "source clinician" desires to reach a "target clinician" in the hospital. This can be achieved by monitoring the communications system head end 650, as well as the data exchanged during an ongoing session for the source clinician, to detect a particular clinician identifier, or the address or directory number of the communication device 614 (e.g., pager or WLAN phone) or terminal 14A, 14B being used by a particular clinician. For the purposes of the discussion below, the particular clinician will be referred to as the "target" clinician.

At step 904, the controller 618 consults the LCE 658 to determine the location of the target clinician identified at step 902. At step 906, the controller 618 determines whether the target clinician is available by applying an "unavailability policy" based at least in part of the location of the target clinician determined at step 904. A non-limiting example of an unavailability policy is to deem the target clinician as "unavailable" when located in a subset of the location-awareness area of the hospital, where the subset includes operating rooms and emergency rooms. Conversely, if the target clinician does not fall within this subset of the location-awareness area of the hospital, the target clinician is deemed to be available.

Generally speaking, the subset of the location-awareness area of the hospital where the target clinician will be deemed unavailable depends on knowledge of the topography of the hospital, i.e., the layout and configuration of the various rooms, floors and areas of the hospital. The topography of the hospital may be stored in the controller 618 or it may be stored in the departmental database 26 and accessed by the controller 618 when needed.

Of course, the unavailability policy may be more complex than the mere identification of certain fixed areas of the hospital where target clinicians are deemed unavailable. For example, the unavailability policy may be a function of the professional role (e.g., doctor vs. nurse vs. orderly) of the target clinician. In yet another example, the target clinician's schedule may impact the result of applying the unavailability policy. For example, a target clinician located in the scrub room before a planned surgical intervention may be deemed unavailable, but would not be deemed unavailable if present in the scrub room after surgery is complete. Hence, the unavailability policy may include an element of target clinician location history as well as actual location. For instance, for the case of "history=general hospital area" and "current location=scrub room" then the target clinician may be deemed unavailable, whereas for "location history=operating theatre" and "current location=scrub room", then the target clinician may be deemed available.

Thus, it is apparent that the unavailability policy may range from simple to complex, to the point where it involves the target clinician's professional role, identity, schedule, etc. It should also be appreciated that the controller 18 may obtain the information relevant for application of the unavailability policy from the clinician database 22, whereas the overall unavailability policy itself may be stored in memory the controller 18, and changed from time to time by hospital administrative staff.

If the outcome of step 906 is that the target clinician is deemed available, then with reference to FIG. 9B, the controller 618 proceeds to step 910, where a paging message is sent to the target clinician. In a non-limiting example embodiment, the paging message can be sent via the communication system head end 650 to reach the communication device 614 (e.g., pager or WLAN phone) being used by the target clinician. Alternatively, the paging message can be sent as an electronic message to the fixed-wire or mobile terminal 14A, 14B with which the target clinician has an ongoing session with the HIS 12. In yet another embodiment, plural uses of a paging message to attempt to reach the target clinician (who, it is recalled, was deemed to be available) can be employed in parallel.

At step 912, the controller 618 is attentive to receipt of a positive acknowledgement from the target clinician, either by way of a response via the terminal 14A, 14B being used by the target clinician or via the communication system head end 650. If a positive acknowledgement is received within a certain amount of time (e.g., 10 seconds), then no further action needs to be taken, since the target clinician has been reached and has positively acknowledged that he or she is available. The remainder of the communication between the source clinician and the target clinician may occur in a conventional manner.

However, if the controller 618 does not receive a positive acknowledgement for a certain amount of time (e.g., 10 seconds) or receives a negative acknowledgement, then the controller 618 proceeds to step 914, where it takes a specific action, depending on the circumstances. A simple example of an action is the display of a reply message at a device being used by the source clinician, which states something to the effect that "Dr. Smith cannot be reached" and offers the source clinician a menu of choices. These may include:

1) Attempt to reach a surrogate clinician for Dr. Smith.
2) Attempt to reach an alternative clinician for Dr. Smith;
3) Leave a message for Dr. Smith.

In this context, a "surrogate clinician" for Dr. Smith represents a clinician who is located near Dr. Smith, and who can therefore contact Dr. Smith in case of emergency, but who may not have a comparable skill set to that of Dr. Smith. An "alternative clinician" for Dr. Smith represents a clinician who has a skill set comparable to that of Dr. Smith, and who acts as a "backup" for Dr. Smith, but who may not be located as near to Dr. Smith as the surrogate clinician. The identity of a surrogate clinician and an alternative clinician for a given target clinician represent additional data elements that are associated with the target clinician and it is envisaged that they may be stored in the clinician database 22 alongside other data for the target clinician. Moreover, the identity of the surrogate clinician may be updated by a function operating in the controller 18, which relies on the LCE 658 to determine which clinician should be the surrogate clinician for the target clinician. Also, there may be more than one alternative or surrogate clinician for any one target clinician. Furthermore, the location of the alternative clinician and/or the skill set of the surrogate clinician may be displayed for the source clinician to consider before selecting one of the options 1), 2) and 3) above.

If the source clinician selects option 1) above, then the controller 618 proceeds to step 916, where an attempt to reach the surrogate clinician is made, e.g., by sending a paging message to the surrogate clinician. In a non-limiting example embodiment, the paging message can be sent via the communication system head end 650 to reach the communication device 614 (e.g., pager or WLAN phone) being used by the surrogate clinician. Alternatively, the paging message can be sent as an electronic message to the fixed-wire or mobile terminal 14A, 14B with which the surrogate clinician has an ongoing session with the HIS 12. In yet another embodiment, plural uses of a paging message to attempt to reach the surrogate clinician (who may or may not be available) can be employed in parallel.

The paging message destined for the surrogate clinician may further contain the message to be passed by the surrogate clinician to the target clinician. Assuming again that the target clinician is Dr. Smith, the paging message sent to the surrogate clinician could be "Kindly find out from Dr. Smith whether he checked on Mrs. Jones this morning.", which exemplifies a simple message asking the surrogate clinician to elicit a simple response from the target clinician, and which cannot be answered until the target clinician is reached.

In the event that option 1) does not end in a satisfactory way (e.g., the surrogate clinician does not positively acknowledge the paging message), then the controller 618 causes the above options to be re-presented to the source clinician.

If the source clinician selects option 2) above, e.g., after execution of step 914 or after execution of step 916, the controller 618 proceeds to step 920, where an attempt to reach the alternative clinician is made, e.g., by sending a paging message to the alternative clinician. In a non-limiting example embodiment, the paging message can be sent via the communication system head end 650 to reach the communication device 614 (e.g., pager or WLAN phone) being used by the alternative clinician. Alternatively, the paging message can be sent as an electronic message to the fixed-wire or mobile terminal 14A, 14B with which the alternative clinician has an ongoing session with the HIS 12. In yet another embodiment, plural uses of a paging message to attempt to reach the alternative clinician (who may or may not be available) can be employed in parallel.

In the event that this option does not end in a satisfactory way (e.g., the alternative clinician does not positively acknowledge the paging message), then the controller 618 causes the above options to be re-presented to the source clinician.

If the source clinician selects option 3) above, e.g., after execution of step 914 or after execution of step 916 or after execution of step 920, then the source clinician is prompted to leave a message for the target clinician. The message is then delivered to, and accessed by, the target clinician in a conventional manner.

It is noted that the selection of option 1), 2) or 3) can be automatic based on source clinician preferences, or manual, based on the judgment of the source clinician. For example, the source clinician may consider that it is preferable to contact a surrogate clinician with a slightly inferior or superior skill set than to contact an alternative clinician who may be further from the target clinician. In other circumstances, the source clinician may decide just the opposite, when a very specific skill set is required.

Returning now to step 906, if the outcome of this step was that the target clinician is deemed unavailable, then with reference now to FIG. 9C, the controller 618 proceeds to step 924, where a reply message is sent to the source clinician. Assuming that target clinician is Dr. Smith, and that the location of the target clinician was found to be "Operating Room 22", the reply message may state something to the effect that "Dr. Smith is currently unavailable in Operating Room 22" and offers the source clinician a menu of choices. These include:

4) Attempt to reach an alternative clinician for Dr. Smith;
5) Leave a message for Dr. Smith;
6) Wait for Dr. Smith to become available;
7) Attempt to reach a surrogate clinician for Dr. Smith.

If the source clinician selects option 4) above, then the controller 618 proceeds to step 926, where an attempt to reach the alternative clinician is made, e.g., by sending a paging message to the alternative clinician. In a non-limiting example embodiment, the paging message can be sent via the communication system head end 650 to reach the communication device 614 (e.g., pager or WLAN phone) being used by the alternative clinician. Alternatively, the paging message can be sent as an electronic message to the fixed-wire or mobile terminal 14A, 14B with which the alternative clinician has an ongoing session with the HIS 12. In yet another embodiment, plural uses of a paging message to attempt to reach the alternative clinician (who may or may not be available) can be employed in parallel.

In the event that this option does not end in a satisfactory way (e.g., the alternative clinician does not positively acknowledge the paging message), then the controller 618 causes the above options to be re-presented to the source clinician.

If the source clinician selects option 5) above, e.g., after execution of step 924 or after execution of step 926, then the source clinician is prompted to leave a message for the target clinician. The message is then delivered to, and accessed by, the target clinician in a conventional manner. If the source clinician selects option 6) above, e.g., after execution of step 924 or after execution of step 926, the controller 618 performs step 928, where communication with the target clinician is delayed until continued application of the unavailability policy reveals that the target clinician has become available. At that point, a paging message is sent as described herein above with reference to step 910 in FIG. 9B and the steps thereafter.

If the source clinician selects option 7) above, then the controller 618 proceeds to step 930, where an attempt is made to reach the surrogate clinician, e.g., by sending a paging message to the surrogate clinician. In a non-limiting example embodiment, the paging message can be sent via the communication system head end 650 to reach the communication device 614 (e.g., pager or WLAN phone) being used by the surrogate clinician. Alternatively, the paging message can be sent as an electronic message to the fixed-wire or mobile terminal 14A, 14B with which the surrogate clinician has an ongoing session with the HIS 12. In yet another embodiment, plural uses of a paging message to attempt to reach the surrogate clinician (who may or may not be available) can be employed in parallel.

The paging message may further contain the message to be passed to the target clinician. Assuming again that the target clinician is Dr. Smith, the paging message sent to the surrogate clinician could be "Thank you for finding out from Dr. Smith whether he checked on Mrs. Jones this morning.", which exemplifies a simple message having a "Yes/No" response but which cannot be asked of any other clinician than the target clinician.

In the event that this option does not end in a satisfactory way (e.g., the alternative clinician does not positively acknowledge the paging message), then the controller 618 causes the above options to be re-presented to the source clinician.

It is noted that the selection of option 4), 5), 6) or 7) can be automatic based on source clinician preferences, or manual, based on the judgment of the source clinician. For instance, option 7) should ideally be used only in cases of extreme urgency, where Dr. Smith's personal input is vital, such as in a matter of life and death. This is reasonable as a last resort since there is a chance that even though Dr. Smith was deemed unavailable at step 908, he or she may still be in a position to reprioritize his or her activities upon evaluating the merits the current situation.

Thus, it should be appreciated that application of an unavailability policy which is sensitive to a target clinician's whereabouts can save valuable time in a situation where one wishes to reach the target clinician. For example, if the target clinician is deemed unavailable, this will be known to the controller 618 and therefore the source clinician will not have to wait in vain for the lack of a response before attempting to contact another clinician. Moreover, the ability to contact a surrogate clinician who is in the vicinity of the target clinician also has advantages.

IV- Medical Event Monitoring Process 840

Figure 10:
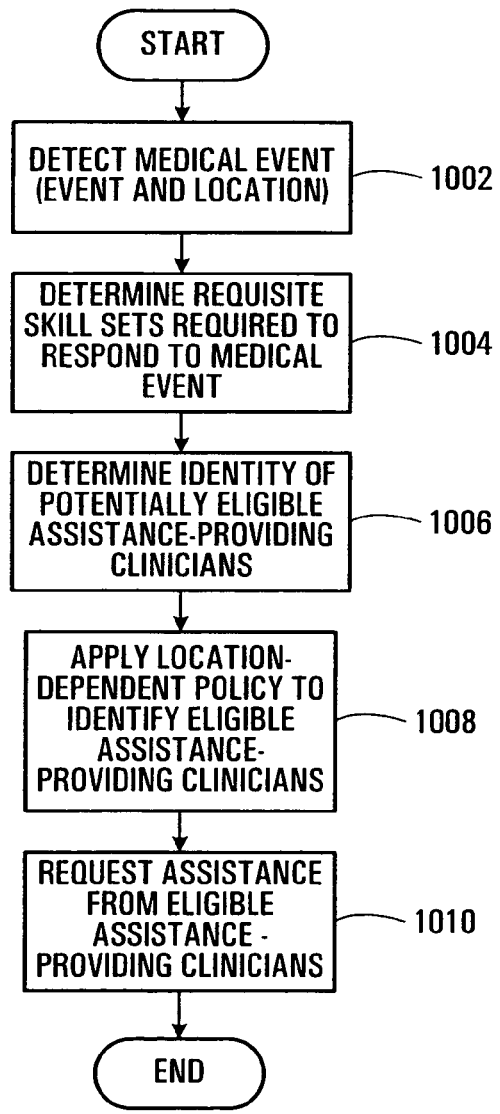
FIG. 10 is a flowchart showing steps in a process used to establish communications with a team of clinicians required to respond to a medical event in the hospital, in accordance with an embodiment of the present invention.

With reference to FIG. 10, at step 1002, the controller 618 detects that an emergency "medical event" has occurred in the hospital, along with its location. The term "medical event" include but is not limited to an internal hospital emergency that afflict a patient admitted to the hospital, such as the occurrence of a heart attack, seizure, etc. However, the term "medical event" should not be construed as applying only to admitted patients, and therefore is meant to include medical emergencies that may afflict a clinician or other worker in the hospital or even a visitor of an admitted patient. In addition, the term "medical event" should also be understood to include an occurrence that is non-medical in nature (such as an electrical shock, hurricane, tornado, flood) but that may require medical assistance.

For example, "Code Blue" is an expression indicative a medical event where a person is possibly in danger of immediately dying. The procedure is to immediately call for help (dial 911 or press the nearest "code blue button") and begin life-saving techniques if necessary. Code Blue buttons (not shown in the drawings) are typically distributed throughout the hospital at known locations, and in an embodiment of the present invention they may be in communication with the controller 618 via a network and/or possibly the communications system head end 650. The controller 618 therefore has the ability to determine when a particular Code Blue button has been pressed as well as the location of that code blue button, which can be determined from the hospital floor plan. Alternatively, for mobile Code Blue buttons, these can be provided with their own tags (not shown) and the location of a Code Blue button that has been pressed would be determined using the TDS 616.

Similarly, the controller 618 has the ability to monitor the communications from the various communication devices 614 in order to detect if someone has dialed 911 and the location of the communication device 614 that has dialed 911. In addition, the nature and location of the medical event can be entered by anyone with access to one of the terminals 14A, 14B, which causes the controller 618 to obtain this information regarding the medical event.

At step 1004, the controller 618 determines a skill set associated with the medical event. For example, a "Code Blue" may require a physician and two nurses. The skill sets associated with various medical events can be encoded in a mapping that is stored in a database (not shown) in the controller 618 or in one of the databases 22, 24, 26, 35, 27.

At step 1006, the controller 618 determines the identity of clinicians whose skills match one or more of the requisite skills sets found at step 1004. For example, by consulting the clinician profiles in the clinician database 22, the controller 618 can determine the identity of the various clinicians who are on duty and who have the requisite skill sets. These clinicians are considered to be "potentially eligible assistance-providing clinicians".

At step 1008, the eligibility of the potentially eligible assistance-providing clinicians is confirmed, at least in part on the basis of distance from where the medical event is taking place. For example, the controller 618 consults the LCE 658, which maintains location information regarding various clinicians based on detection of the tags worn by those clinicians. On the basis of the location of the medical event and the locations of the potentially eligible assistance-providing clinicians, the controller 618 determines which potentially eligible assistance-providing clinicians are eligible to provide assistance for the medical event. Thus, in one embodiment, eligibility can be a function of proximity to the medical event; in other words, the closer a potentially eligible assistance-providing clinician is to the medical event, the more eligible he or she is deemed to be to provide assistance. However, it should be understood that a more complex, but still location-dependent, policy can be applied, based additionally on schedule, historical data, etc.

The net result of this approach is that the nearest suitably qualified clinicians (i.e., the eligible assistance-providing clinicians) are summoned, thereby minimizing the time to bring the "code blue" team together.

At step 1010, the controller 618 requests assistance from the eligible assistance-providing clinicians determined at step 1008. Specifically, this can involve transmission of a message to the eligible assistance-providing clinicians which specifies the nature and location of the medical event, as determined at step 1002. The message destined for a particular eligible assistance-providing clinician can be transmitted to that clinician via a fixed-wire or mobile terminal 14A, 14B being used by the clinician, or through a communication device 614 (e.g., pager or WLAN phone) being used by the clinician, etc. If the eligible assistance-providing clinician is the only one having that skill set within a certain acceptable distance from the medical event, and if an that clinician is not reachable for any reason, then a surrogate clinician in the vicinity may be contacted to forward the message.

In a variant, steps 1006 and 1008 can be reversed. Specifically, the controller 618 may begin by applying a location-dependent policy to all clinicians, regardless of their skill set. For example, the controller 618 may consult the LCE 658 in order to obtain the identity and location of the clinician closest to the medical event. In other cases, the location-dependent policy may be more complex. In any event, the end result is the identification of an "eligible potentially assistance-providing clinician", i.e., a clinician who is located close to the medical event, but whose skill set remains unknown. Accordingly, the controller 618 then consults the clinician database 22 to determine whether the skill set associated with the eligible potentially assistance-providing clinician matches or exceeds one of the skill sets that is required in order to handle the medical event. If so, that particular skill set is considered to have been met and the search for an eligible assistance-providing clinician is over for that particular skill set (although there may be more than one requisite skill set or a need for more than one clinician of the same skill set; in such cases, the process is repeated as many times as needed). If, however, the eligible potentially assistance-providing clinician does not have any of the requisite skill sets, then this clinician is not "assistance-providing" and the search continues for the next closest clinician, et cetera, until an eligible assistance-providing clinician for all requisite skill sets has been identified. Again, operation of the controller 618 expedites formation of a response team to the medical event, by identifying the nearest clinicians of the requisite skill set. In this way, precious seconds or minutes can be saved before the team is assembled.

V- RF Interference Monitoring Process 850

In order to support the RF interference monitoring process 850, the equipment database 35 is expanded so as to include additional fields for each piece of tagged equipment (e.g., terminal or medical device), including but not limited to RF-radiating terminals and sensitive medical devices. Specifically, with reference to FIG. 12, an enhanced equipment database 1235 includes the same fields as the equipment database 35 in FIG. 1D, in addition to a "maximum transmitted RF power" field 1210 and an "exposed RF field strength limit" field 1220. Of course, an enhanced equipment database could be based on the enhanced equipment database 1135 previously described with reference to the tagged equipment monitoring process 820.

For a given piece of tagged equipment, the "maximum transmitted RF power" field 1210 indicates the maximum level of RF power that can be generated by the given piece of tagged equipment under its current operating condition. This may be given in units such as milliwatts (mW). For example, a WLAN phone may generate in the range of 50-100 mW of RF power.

For a given piece of tagged equipment, the "exposed RF field strength limit" field 1220 indicates the immunity of the given piece of tagged equipment, e.g., level of RF interference that the given piece of tagged equipment is designed to withstand. One common way of expressing the exposed RF field strength limit is in terms of a field strength (V/meter) over a given range of frequencies. The immunity may be defined by a standard, a non-limiting example of which is IEC-60601-1-2, $2^{nd}$, 2001 edition, incorporated by reference herein. According to this standard, modern medical devices are required to function in a 10V/m radio frequency interfering field (over a wide RF frequency range) if it is life-supporting equipment and 3V/m if it is not life-supporting. In other words, life-supporting equipment manufactured to meet the above standard may malfunction if exposed to RF interference having a level of greater than 10V/m and non-life-supporting equipment manufactured to meet the above standard may malfunction if it is exposed to RF interference having a (somewhat weaker) level of more than 3 V/m.

Based on the above example data, a WLAN phone operating at around 50-100 mW can come to within about 2 meters of a 3V/m-immune medical device or to within about 0.6-0.7 meters of a 10 V/m-immune medical device without any deleterious effect, but coming any closer both violates IEC-60601-1-2 and puts the performance of the medical device in jeopardy. Those skilled in the art will appreciate that IEC-60601-1-2 defines adequate and ample margins such that, irrespective of propagation conditions, a transmitter that does not approach a medical instrument to closer that the transmit-power-dependent-distance defined in that specification can never cause an RF field in excess of the design limits of a medical instrument at that transmit power.

Also, it is recalled that the medical devices 602 themselves are equipped with tags, which are transmitting elements in their own right. While this may seem self-defeating at first glance, interference into the medical device 602 can be avoided by using ultra-low-power transmission. This is possible because the bandwidth needed to convey a tag identifier at a required periodicity is miniscule, relative to the bandwidth required for communication via a WLAN phone. Specifically, by application of Shannon's limit theory on information channels, the low data rate requirement allows the tags to operate at a significantly lower power level than a WLAN phone.

For example, the tags may be UWB multi-GHz tags which transmit infrequent (1-10/sec) RF bursts of very short duration (e.g. 1 nanosecond) and with burst peak powers around 15-30 mW such that the integrated RF power over time is extremely low (nanowatts or less), such that it does not interfere with narrowband or even wideband electronics found in a given medical device. On the other hand, the spectral components of multi-GHz CW modulated transmissions from a WLAN phone do interfere if received at a high enough power, since non-linearities in the electronics of the medical device rectify the high-frequency carrier, thereby injecting the resulting demodulated envelope into the rest of the medical device. This may contain signal components within the passband of the medical device, causing the latter to malfunction.

Since a sensitive medical device may malfunction if strong sources of RF power are brought so close as to overcome the immunity of the medical device in question, it becomes highly advantageous to control the transmitted RF power as a function of distance between the sensitive medical device and the source of RF power. Specifically, as a source of RF power approaches the sensitive medical device (or vice-versa), it is advantageous to reduce the transmitted RF power of the source. Conversely, when there is no longer any sensitive medical device in the vicinity of the emitter, its transmitted RF power can be increased again (e.g., in order to support a higher data rate).

Figure 13:
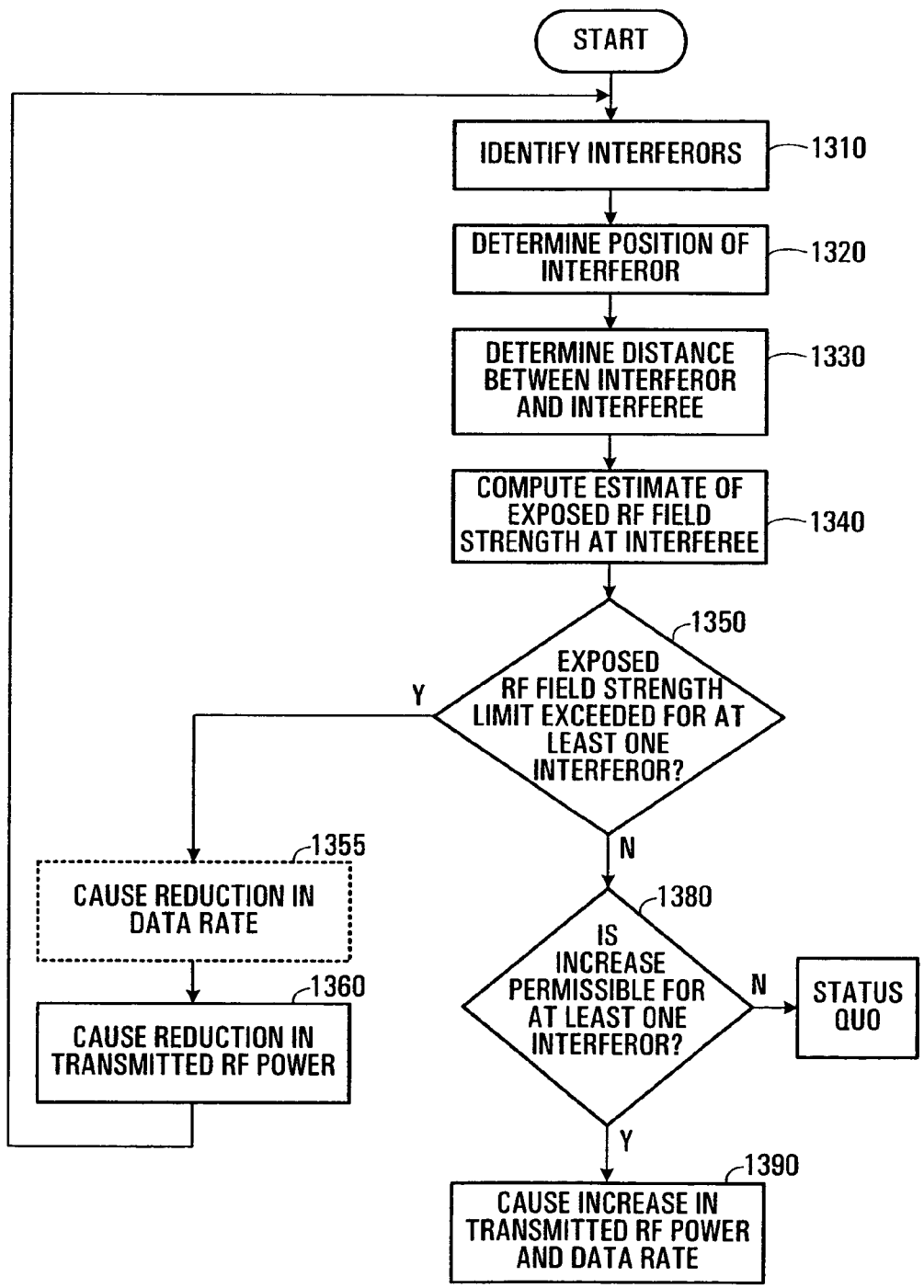
FIG. 13 is a flowchart showing steps in a process used to monitor and control RF interference, in accordance with an embodiment of the present invention.

The aforementioned principle is now described in somewhat greater detail with additional reference to FIG. 13, which is shown as being executed for a particular piece of tagged equipment having a non-zero entry in the exposed RF field strength limit field 1220. This is representative of a sensitive medical device and will hereinafter be referred to as an "interferee". It should be understood that a similar flowchart may be executed in parallel for all other interferees.

At step 1310, based on the data from the enhanced equipment database 1135 and the data from the TDS 616, the RF interference monitoring process 850 identifies those pieces of tagged equipment having a non-zero entry in the transmitted RF power field 1210. In other words, the RF interference monitoring process 850 identifies potential sources of RF interference for the interferee, which are hereinafter referred to as "interferors".

At step 1320, for each given interferor, the RF interference monitoring process 850 determines the position of the tag associated with the given interferer (along with the position of the tag associated with the interferee, although this could possibly be pre-computed or computed on a less frequent basis). At step 1330, the RF interference monitoring process 850 determines the estimated distance between the positions computed at step 1320. At step 1340, the RF interference monitoring process 850 computes an estimate of the exposed RF field strength at the interferee by computing a mathematical function of (i) the current transmitted RF power of the given interferer and (ii) the estimated distance between each given interferor and the interferee (found at step 1330).

In specific non-limiting examples, the mathematical function may be based upon (a) textbook inverse-square-law-based free space propagation properties; (b) a reference model (e.g. AWGN, HiperLAN) that tries to take into account median building properties; and/or (c) mathematical relationships defined in IEC-60601-1-2 or a similar direct EMI standard. Where a reference is in place, such as the IEC-60601-1-2 standard, the transmit-power/interferee-sensitivity/interferor-interferee-distance relationships from the reference can be used to ensure that transmitters do not violate a safe power level according to that reference.

Generally speaking, the mathematical function may take into consideration various useful, concrete and tangible factors, such as analytical data regarding free space propagation and empirical data regarding propagation in the environment of the hospital in question (or hospitals in general). In addition, the mathematical function may also take into consideration the location coordinates of the tags associated with each given interferor and the interferee with respect to topographical and structural knowledge of the hospital (e.g., floor plan, number and thickness of walls between each given interferor and the interferee, as well as materials used to construct them), in addition to knowledge of whether each given interferer and the interferee are located on the same floor (to account for RF absorption by floors and ceilings). Still other functions that permit the computation of an estimate of the exposed RF field strength at the interferee are within the scope of the present invention.

At step 1350, the outcome of step 1340, which is an estimate of the exposed RF field strength at the interferee due to each given interferor, is compared to the value in the exposed RF field strength limit field 1220 for the interferee. If the estimate of the exposed RF field strength is greater than the exposed RF field strength limit (or less than but to within a pre-determined delta thereof) for at least one of the given interferors (hereinafter referred to as a "guilty interferor" or "guilty interferors"), then the RF interference monitoring process 850 concludes that the current transmitted RF power level of the guilty interferor(s) is excessive. In general terms, it can be said that an "RF interference constraint" is violated). Thus, in response, the next step is step 1360, where the RF interference monitoring process 850 sends a message to the power control entity 630, causing it to send a message to each guilty interferor, ultimately causing the guilty interferors to reduce their transmitted RF power by a certain amount (hereinafter referred to as a step size) or to a specific level.

The process then returns to step 1310, which eventually leads to a computation of new estimates of the exposed RF field strength at the interferee due to various interferors (including the guilty interferor(s)).

Assuming for argument's sake that the guilty interferor(s) and the interferee have not moved relative to one another, the new exposed RF field strength estimates at the interferee due to the guilty interferor(s) will tend to be lower than the previous ones, and if the step size is chosen judiciously, the new estimates of the exposed RF field strength will fall below the value in the exposed RF field strength limit field 1220 for the interferee, hence not requiring a further reduction in the RF power generated by the guilty interferors.

It is noted that in some cases where the interferor is a mobile terminal, a session may be ongoing between the mobile terminal and the HIS 12 when the above steps take place. By lowering the transmitted RF power of the mobile terminal in accordance with step 1360, the mobile terminal may not be able to maintain the same data rate for the ongoing session, in the direction from the mobile terminal to the HIS 12. In other words, reducing the transmitted RF power may have the consequence of degrading the transmission capability between the mobile terminal and the nearby WLAN access point 60. This can be addressed by reducing the channel throughput and adapting the radio link to the new conditions. Standard techniques may be used for this purposes, such as those described in IEEE standard 802.11.

Accordingly, before causing the mobile terminal to lower the transmitted power, the RF interference monitoring process 850 may perform an additional step 1355, whereby a command is sent to the session management function 53, such command being instrumental in causing the session management function 53 to lower the data rate being used by the mobile terminal to transmit over the communication network 610. This may be achieved by using less dense coding constellations, resulting in lower throughput.

Returning now to step 1350, if execution of this step revealed that the estimate of the exposed RF field strength at the interferee due to each given interferor is less than the value in the exposed RF field strength limit field 1220 for the interferee, then the RF interference monitoring process 850 proceeds to step 1380, where it is determined whether those interferors who are not at full power (i.e., transmitting at a level less than the value of the "maximum transmitted RF power" field 1210 for the interferor in question), would hypothetically cause the RF interference constraint to be violated if they were to transmit at the next highest power setting.

If there is no such hypothetical violation of the RF interference constraint for a particular interferor, the controller 18/618 proceeds to step 1390 where it causes the transmitted RF power (and, correspondingly, the data rate) to be increased for the particular interferor. On the other hand, if there would be a hypothetical violation of the RF interference constraint for a particular interferor, there is no change in the transmitted power level for the particular interferor. Similarly, for those interferors already transmitting at full power, there is no change in the transmitted power level.

Thus, as a given interferor and the interferee get closer to one another, the RF interference monitoring process 850 causes the given interferor to transmit at ever lower RF power levels, and also causes the use of less dense coding constellations. Despite the reduced throughput, a session can be maintained while the interferer in question can be brought much closer to the interferee than would be possible at full power.

It should also be noted that the reduced throughput for a given interferer is not a disadvantage in most cases, since it affects the relatively low data rate in the direction from the given interferer to the HIS 12. There is typically no need to adjust the transmit power of the WLAN access points 60 (i.e., in the reverse direction), since they are strategically positioned in locations close to the ceiling and may have complex antenna patterns, such that interference with stationary sensitive medical device can be avoided by design. However, should a sensitive medical device be moved around (e.g., during surgery) to approach a WLAN access point 60, it is within the scope of the present invention to apply the principles described above to temporarily reduce the transmit power of the WLAN access point.

The communications network 10 of the first system architecture and/or the communications network 610 of the second system architecture may also comprise a plurality of chargers disposed at various locations throughout the hospital for the example purpose of replenishing the battery charge in handheld devices. The chargers are connected to the controller 18/618 by a communications link. In an embodiment, the chargers comprise charging stations for receiving mobile terminals (such as PDAs or tablet PCs) and having electrical connections for providing a recharging capability. The mobile terminals in the charger do not support any session for any clinician.

A certain level of interaction between a given clinician (hereinafter denoted 20*) and a given charger occurs where clinician 20* inserts into the charger a mobile terminal that he or she is currently using, for example, when leaving for the day or when the battery is near exhaustion. In this case, clinician 20* approaches the charger, where his or her presence will be detected by a clinician-charger proximity monitoring process executed by the controller 18 in the first system architecture and/or the controller 618 in the second system architecture. The controller 18/618 may then execute a series of steps, such as (in the case where an ongoing session exists) causing the display of a greeting message such as "Please insert this mobile terminal into a charging station and consider whether you wish to terminate or suspend your session", or any conceivable variant thereof. Before inserting the mobile terminal into the charger, clinician 20* may thus choose to explicitly terminate or suspend an ongoing session (if there is one). Explicit termination or suspension of a session has already been described herein above in the context of scenarios C- and D-, respectively. It will be recalled that termination leads to ending the session for clinician 20*, whereas suspending the session has the effect of putting the session "on-hold" until clinician 20* authenticates himself/herself when in the vicinity of another terminal.

Another level of interaction between clinician 20* and the charger may occur where clinician 20* is deemed to not be using a mobile terminal and is also deemed to be "in proximity" to the charger (i.e., has satisfied a proximity condition). For example, this may occur when clinician 20* begins his or her shift, or has just inserted his or her mobile terminal into the charger, possibly following suspension or termination of a session as described in the previous paragraph. The fact that clinician 20* is in proximity to the charger and that clinician 20* is not using a mobile terminal is detected by the aforementioned clinician-charger proximity monitoring process executed by the controller 18 in the first system architecture and/or the controller 618 in the second system architecture. In this case, the controller 18/618 executes a series of steps, as now described with reference to FIG. 14.

At step 1410, a signal is provided to clinician 20* to suggest a particular mobile terminal that he or she may use. This may be done by controlling (e.g., by way of colour or by blinking) a light located on the outside of the suggested mobile terminal or causing the display of a personalized greeting message on the suggested mobile terminal. This may also be done by controlling a visual indicator on the charger itself so as to indicate to the clinician 20* the suggested mobile terminal. The suggested mobile terminal may be selected on the basis of charge capacity or other parameter. Optionally, at step 1420, a locking mechanism which is by default engaged for all mobile terminals in the charger would be disengaged for the suggested mobile terminal while remaining engaged for all other mobile terminals presently in the charger.

(It should be noted that in the absence of a locking mechanism, removal of a mobile terminal may be possible by someone who does not have a clinician's tag, and therefore it may be appropriate to detect this fact using the process being described here. Even if this is not the case, such action would nevertheless be detected as potentially suspicious motion by the tagged equipment monitoring process 820 described above.)

Once the suggested mobile terminal is extracted by clinician 20*, the controller 18/618 proceeds to step 1430, whereby authentication data is awaited from clinician 20*, either in response to a request (such as may be issued via a greeting message) or sua sponte. This represents an opportunity for clinician 20* to authenticate himself/herself. If a suitable response is not received within a predetermined amount of time (e.g., 3 seconds), the controller 18/618 proceeds to step 1440, where it infers that the mobile terminal has been taken by someone who, although equipped with clinician 20*'s tag (resulting in unlocking of the now extracted mobile terminal), is not familiar with the need to authenticate oneself. Since this may arise in the context of theft, an action is taken at step 1450 to signal a problem. For example, an audible or visual alarm may be triggered at the charger, and security personnel may be advised.

On the other hand, authentication data may be received at step 1430, in which case the authentication process 70 previously described may be may be executed at step 1460. If the result of the authentication process is a failure, then at step 1450, similar action to the above may be taken (e.g., sounding of an alarm, etc.)

Assuming that the result of the authentication process is a success, then the controller 18/618 proceeds to step 1470, where the clinician database 22 is consulted, resulting in the acquisition of appropriate personalization or customization parameters for the purposes of initializing the extracted mobile terminal. The controller 18/618 then proceeds to step 1480, whereby if there is a suspended session for clinician 20*, the controller 18/618 causes the session to be resumed in the manner previously described in this specification. Where there is no suspended session for clinician 20*, the remaining steps as described herein above in the context of the session establishment process 82 are performed in order to establish a session for clinician 20*.

Figure 15:
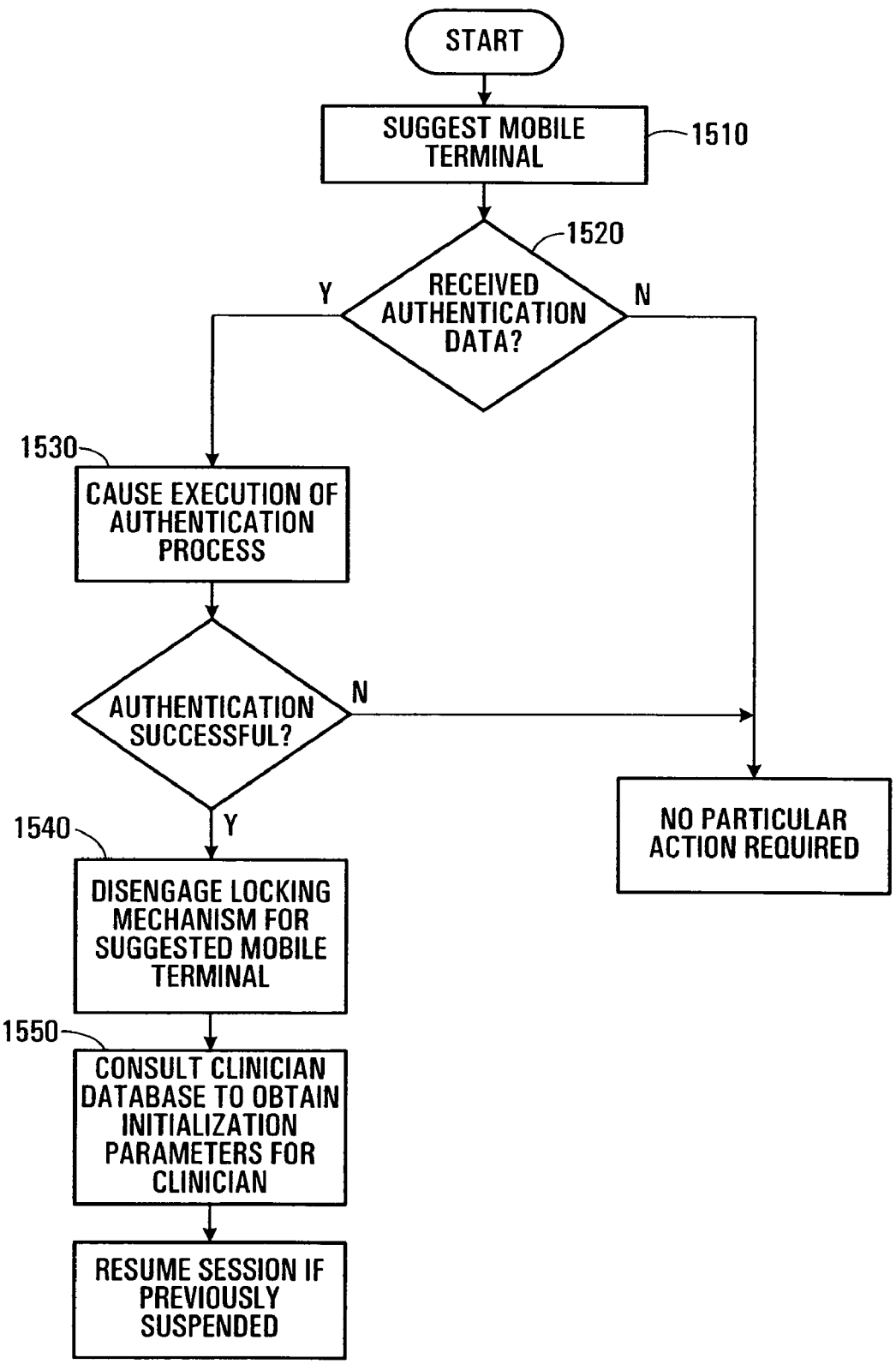

An alternative sequence of steps in the interaction between clinician 20* and the charger, following detection of the state where clinician 20* is in proximity to the charger but is not using a mobile terminal, is now described with reference to FIG. 15. In this case, a locking mechanism is by default engaged for all mobile terminals in the charger.

Figure 14:
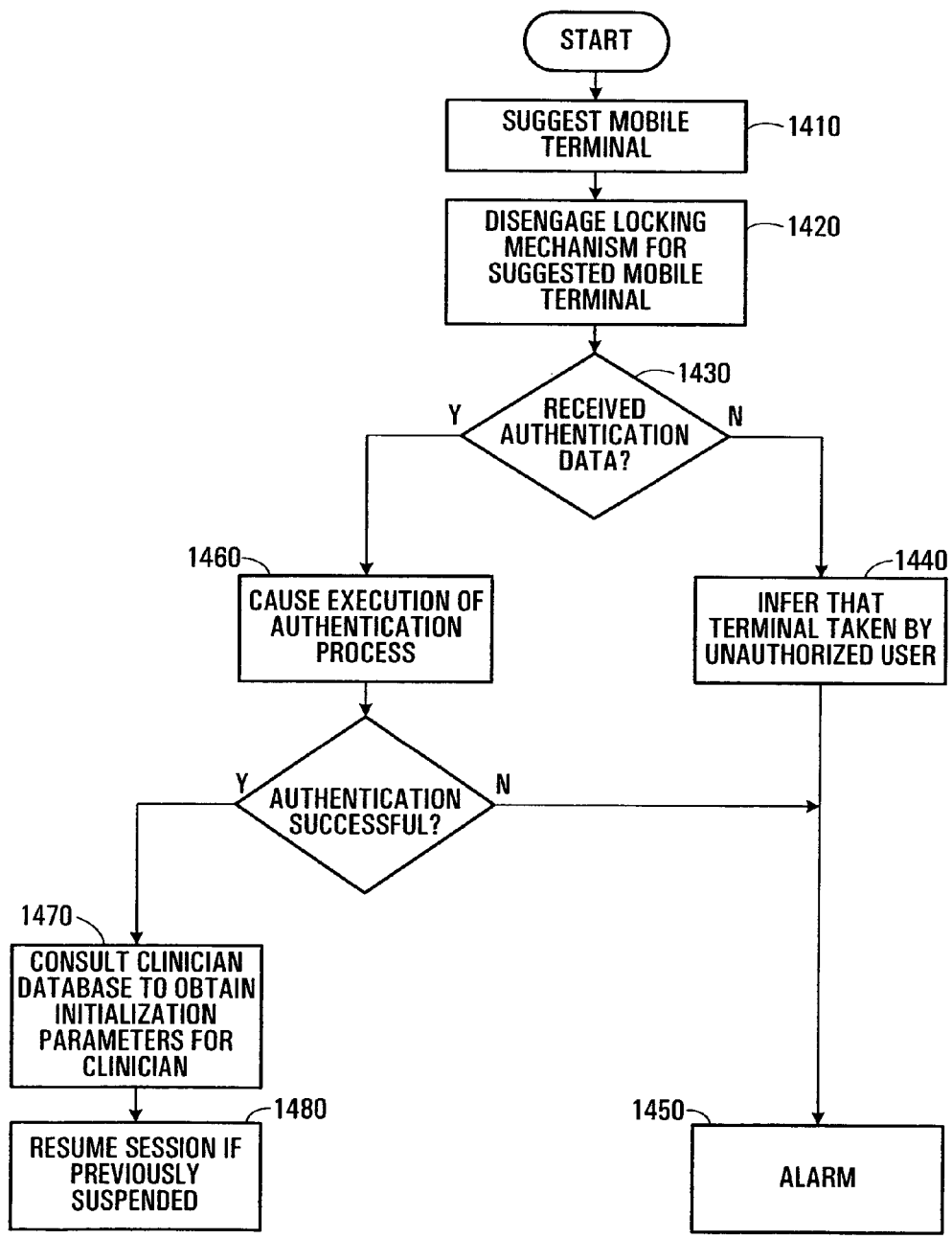
FIGS. 14 and 15 are flowcharts showing steps in two alternative versions of a process used to describe control of, and interaction with, a charger of mobile terminals, in accordance with an embodiment of the present invention.

At step 1510, which is identical to step 1410 in FIG. 14, a signal is provided to clinician 20*  to suggest a particular mobile terminal that he or she may use. This may be done by controlling (e.g., by way of colour or by blinking) a light located on the outside of the suggested mobile terminal or causing the display of a personalized greeting message on the suggested mobile terminal. The suggested mobile terminal may be selected on the basis of charge capacity or other parameter.

The controller 18/618 then proceeds to step 1520, whereby authentication data is awaited from clinician 20*, either in response to a request or sua sponte. If a suitable response is not received within a predetermined amount of time (e.g., 3 seconds), then the controller 18/618 does not need to do anything, since the locking mechanism remains engaged with respect to the mobile terminals in the charger.

On the other hand, authentication data may be received at step 1520, in which case the authentication process 70 previously described may be may be executed at step 1530. If the result of the authentication process is a failure then, again, the controller 18/618 does not need to do anything, since the locking mechanism remains engaged with respect to the mobile terminals in the charger.

However, assuming that the result of the authentication process is a success, the controller 18/618 proceeds to step 1540, where the locking mechanism is disengaged for the suggested mobile terminal, allowing the suggested terminal to be extracted. Next, the controller 18/618 executes step 1550, where the clinician database 22 is consulted, resulting in the acquisition of appropriate personalization or customization parameters for the purposes of initializing the extracted mobile terminal.

At this stage, clinician 20*  is in possession of the suggested mobile terminal and is in fact detected to be in proximity to the suggested mobile terminal, which may trigger the various session establishment and session resumption processes described above. For example, if there is a suspended session for clinician 20*, the controller 18/618 causes the session to be resumed in the manner previously described in this specification. Where there is no suspended session for clinician 20*, the controller 18/618 causes the session to be established in the manner previously described in this specification. Since both of these processes require authentication of clinician 20*, it will be seen that there are in fact two authentications that clinician 20*  needs to perform before gaining access to the HIS 12 in the embodiment of FIG. 15, as opposed to one in the embodiment of FIG. 14. However, the embodiment of FIG. 15 guarantees that a mobile terminal will not be taken by an unauthorized individual and hence obviates the step of signaling an alarm condition.

Thus, the present disclosure has shown how a healthcare information system (HIS) such as a hospital or clinical information system which allows clinicians access to various hospital databases including patients' electronic health records (EHRs) can be made more efficient, effective, safe and functional by the exploitation of location awareness.

It should be mentioned that the examples of proximity and remoteness conditions have been simplified for the benefit of the reader. Those skilled in the art will appreciate that the parameters used to define the various proximity and remoteness conditions can be tailored to suit specific operational requirements, and that additional parameters can be used. Furthermore, different parameters can be used for declaring proximity or remoteness of different types of terminals (e.g., fixed-wire vs. mobile), different professional roles, different individual clinicians, different types of medical devices, etc.

Those skilled in the art will appreciate that in some embodiments, certain functionality or functional entities of the controller 18/618, the authentication entity 28 and/or the HIS 12 may be implemented as pre-programmed hardware or firmware elements (e.g., application specific integrated circuits (ASICs), electrically erasable programmable read-only memories (EEPROMs), etc.), or other related components. In other embodiments, the controller 18/618, the authentication entity 28 and/or the HIS 12 may comprise an arithmetic and logic unit (ALU) having access to a code memory (not shown) which stores program instructions for the operation of the ALU in order to implement the functional entities and execute the various processes and functions described above. The program instructions could be stored on a medium which is fixed, tangible and readable directly by the controller 18/618, the authentication entity 28 and/or the HIS 12, (e.g., removable diskette, CD-ROM, ROM, or fixed disk), or the program instructions could be stored remotely but transmittable to the controller 18/618, the authentication entity 28 and/or the HIS 12 via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

Although various embodiments have been illustrated, this was for the purpose of describing, but not limiting, the invention. Various modifications will become apparent to those skilled in the art and are within the scope of the present invention, which is defined by the attached claims.

What is claimed is:

1. A method of requesting assistance for a medical event occurring in a healthcare establishment, said method being executed by at least one computer, the method comprising:
   in a controller, receiving data regarding a location of the medical event within the healthcare establishment;
   in the controller, receiving data regarding a type of the medical event;
   in a location calculation engine, receiving data regarding at least one wirelessly detectable tag, each one of the at least one wirelessly detectable tag being associated with a respective one of at least one clinician;
   in the location calculation engine, determining a respective location of each one of the at least one clinician within the healthcare establishment based at least in part on the data regarding the at least one wirelessly detectable tag;
   in the controller:
      determining a requisite skill set associated with the medical event based at least in part on the type of the medical event;
      obtaining a respective profile of each one of the at least one clinician, wherein the respective profile of each one of the at least one clinician indicates whether each one of the at least one clinician has the requisite skill set;
      identifying at least one potential assistance-providing clinician of the at least one clinician as being qualified to provide assistance for the medical event, based at least in part on the requisite skill set associated with the medical event and the respective profile of each one of the at least one clinician;
      identifying at least one particular clinician of the at least one potential assistance-providing clinician as being eligible to provide assistance for the medical event, based at least in part on proximity of the location of the medical event to the respective location of each one of the at least one potential assistance-providing clinician;

determining an availability of the at least one particular clinician of the at least one potential assistance-providing clinician identified as being eligible to provide assistance for the medical event based on a present location and a next likely location of the at least one particular clinician; and performing an action to cause requesting of assistance for the medical event from each one of the at least one particular clinician.

2. A method as defined in claim 1, wherein the data regarding the at least one wirelessly detectable tag comprises, for each given wirelessly detectable tag:

data indicative of an identifier of the given wirelessly detectable tag; and data indicative of a respective distance between the given wirelessly detectable tag and each one of at least three detectors spatially distributed in the healthcare establishment, each one of the at least three detectors being operative to detect a signal provided by the given wirelessly detectable tag.

3. A method as defined in claim 2, wherein the data indicative of a respective distance between the wirelessly detectable tag and each one of at least three detectors spatially distributed in the healthcare establishment comprises data indicative of a respective travel time of the signal detected by each one of the at least three detectors.

4. A method as defined in claim 2, wherein the data indicative of a respective distance between the wirelessly detectable tag and each one of at least three detectors spatially distributed in the healthcare establishment comprises data indicative of a respective intensity of the signal detected by each one of the at least three detectors.

5. A method as defined in claim 1, wherein determining the availability of the at least one particular clinician of the at least one potential assistance-providing clinician identified as being eligible to provide assistance for the medical event comprises determining the availability of the at least one particular clinician based on a relationship between the present location and a location history of the at least one particular clinician.

6. A method as defined in claim 1, wherein performing the action to cause requesting of assistance for the medical event comprises, when the availability of the at least one particular clinician indicates that the at least one particular clinician is unavailable, displaying a message indicating that the at least one particular clinician is unavailable and providing a plurality of options, wherein the plurality of options comprise attempting to reach a surrogate clinician for the at least one particular clinician, attempting to reach an alternative clinician for the at least one particular clinician, and leaving a message for the at least one particular clinician.

7. A method as defined in claim 1, wherein the next likely location of the at least one particular clinician is based on a schedule of the at least one particular clinician.

8. A method as defined in claim 1, wherein the next likely location of the at least one particular clinician is based on a previous location of the at least one particular clinician prior to the present location of the at least one particular clinician.

9. A method as defined in claim 1, wherein the at least one particular clinician identified as being eligible to provide assistance for the medical event comprises the at least one particular clinician of the at least one potential assistance-providing clinician being (1) qualified for the type of the medical event and (2) located closest to the location of the medical event.

10. A method as defined in claim 1, wherein performing an action to cause requesting of assistance for the medical event from each one of the at least one particular clinician comprises generating a respective message destined for each one of the at least one particular clinician.

11. A method as defined in claim 10, wherein the respective message destined for each one of the at least one particular clinician is indicative of the location of the medical event.

12. A method as defined in claim 11, wherein the respective message destined for each one of the at least one particular clinician is also indicative of the type of the medical event.

13. A method as defined in claim 10, wherein the respective message destined for each one of the at least one particular is automatically generated.

14. A method as defined in claim 10, wherein the respective message destined for each one of the at least one particular clinician is a paging message.

15. A method as defined in claim 10, wherein the respective message destined for each one of the at least one particular clinician is an electronic mail message.

16. A method as defined in claim 10, wherein a given one of the at least one particular clinician is associated with a communications device, said method further comprising sending the respective message destined for the given one of the at least one particular clinician to the communications device.

17. A method as defined in claim 16, wherein the communications device is a mobile communications device.

18. A method as defined in claim 17, wherein the mobile communications device is one of a pager, a wireless local area network phone, a personal digital assistance, and a cellular telephone.

19. A method as defined in claim 16, further comprising, prior to sending the respective message destined for the given one of the at least one particular clinician to the communications device, learning of the communications device associated with the given one of the at least one particular clinician based at least in part on the location of the given one of the at least one particular clinician.

20. A method as defined in claim 10, further comprising, for each given particular clinician of the at least one particular clinician:

sending the respective message destined for the given particular clinician to the given particular clinician;

being attentive to reception within a predetermined period of time of a positive acknowledgement of the respective message by the given particular clinician; and responsive to expiry of the predetermined period of time without reception of a positive acknowledgement of the respective message by the given particular clinician, performing an action to indicate that the given particular clinician has not positively acknowledged the respective message.

21. A method as defined in claim 10, further comprising, for each given particular clinician of the at least one particular clinician:

sending the respective message destined for the given particular clinician to the given particular clinician;

being attentive to reception within a predetermined period of time of a positive acknowledgement of the respective message by the given particular clinician; and responsive to expiry of the predetermined period of time without reception of a positive acknowledgement of the respective message by the given particular clinician, obtaining an indication of a surrogate clinician associated with the given particular clinician and sending a message to the surrogate clinician.

22. A method as defined in claim 21, wherein the message sent to the surrogate clinician contains a message to be communicated to the given particular clinician by the surrogate clinician.

23. A system for requesting assistance for a medical event occurring in a healthcare establishment, said system comprising:
- a location calculation engine configured to determine a location within the healthcare establishment where the medical event has occurred, and determine, based at least in part on data regarding wirelessly detectable tags associated with respective clinicians, the respective locations of the respective clinicians within the healthcare establishment;
- a controller configured to determine a requisite skill set associated with the medical event based at least in part on a type of the medical event, and obtain a respective profile of each one of the respective clinicians, wherein the respective profile of each one of the respective clinicians indicates whether each one of the respective clinicians has the requisite skill set;
- the controller configured to identify at least one potential assistance-providing clinician of the respective clinicians as being qualified to provide assistance for the medical event, based at least in part on the requisite skill set associated with the medical event and the respective profile of each one of the respective clinicians, and identify at least one particular clinician of the at least one potential assistance-providing clinician as being eligible to provide assistance for the medical event, based at least in part on proximity of the location of the medical event to the respective locations of each one of the at least one potential assistance-providing clinician;
- the controller configured to determine an availability of the at least one particular clinician of the at least one potential assistance-providing clinician identified as being eligible to provide assistance for the medical event based on a present location and a next likely location of the at least one particular clinician; and
- the controller configured to cause assistance for the medical event to be requested from each one of the at least one particular clinician.

24. A computer-readable storage medium comprising a program element for execution by a computing device to request assistance for a medical event occurring in a healthcare establishment, the program element including:
- computer-readable program code for determining a location within the healthcare establishment where the medical event has occurred;
- computer-readable program code for determining, based at least in part on data regarding wirelessly detectable tags associated with respective clinicians, the respective locations of the respective clinicians within the healthcare establishment;
- computer-readable program code for determining a requisite skill set associated with the medical event based at least in part on a type of the medical event;
- computer-readable program code for obtaining a respective profile of each one of the respective clinicians, wherein the respective profile of each one of the respective clinicians indicates whether each one of the respective clinicians has the requisite skill set;
- computer-readable program code for identifying at least one potential assistance-providing clinician of the respective clinicians as being qualified to provide assistance for the medical event, based at least in part on the requisite skill set associated with the medical event and the respective profile of each one of the respective clinicians;
- computer-readable program code for identifying at least one particular clinician of the at least one potential assistance-providing clinician as being eligible to provide assistance for the medical event, based at least in part on proximity of the location of the medical event to the respective locations of each one of the at least one potential assistance-providing clinician;
- computer-readable program code for determining an availability of the at least one particular clinician of the at least one potential assistance-providing clinician identified as being eligible to provide assistance for the medical event based on a present location and a next likely location of the at least one particular clinician; and
- computer-readable program code for causing assistance for the medical event to be requested from each one of the at least one particular clinician.

* * * * *